(12) United States Patent
Jeong et al.

(10) Patent No.: US 10,959,642 B2
(45) Date of Patent: Mar. 30, 2021

(54) METHODS AND SYSTEMS OF EVALUATING AXONAL LOSS AND DEMYELINATION

(71) Applicant: UNIVERSITY OF UTAH RESEARCH FOUNDATION, Salt Lake City, UT (US)

(72) Inventors: Eun-Kee (E. K.) Jeong, North Salt Lake City, UT (US); Nabraj Sapkota, Salt Lake City, UT (US); Kyle Jeong, Salt Lake City, UT (US); Youjung Lee, Salt Lake City, UT (US); Bijaya Thapa, Salt Lake City, UT (US); John W. Rose, Salt Lake City, UT (US); Lubdha Shah, Salt Lake City, UT (US); Erica Bisson, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 706 days.

(21) Appl. No.: 15/682,046

(22) Filed: Aug. 21, 2017

(65) Prior Publication Data

US 2018/0049665 A1    Feb. 22, 2018

Related U.S. Application Data

(60) Provisional application No. 62/377,032, filed on Aug. 19, 2016.

(51) Int. Cl.
*A61B 5/055*  (2006.01)
*G01R 33/563*  (2006.01)
*G01R 33/48*  (2006.01)
*G01R 33/44*  (2006.01)
*G01R 33/483*  (2006.01)

(52) U.S. Cl.
CPC .......... *A61B 5/055* (2013.01); *G01R 33/445* (2013.01); *G01R 33/4824* (2013.01); *G01R 33/56341* (2013.01); *A61B 2576/026* (2013.01); *G01R 33/4835* (2013.01)

(58) Field of Classification Search
None
See application file for complete search history.

(56) References Cited

U.S. PATENT DOCUMENTS

2016/0231410 A1 *  8/2016  Warfield .............. A61B 5/055

OTHER PUBLICATIONS

Nilsson et al. (2009). On the effects of a varied diffusion time in vivo: is the diffusion in white matter restricted? Magnetic Resonance Imaging. 27: 176-187 (Year: 2009).*

(Continued)

*Primary Examiner* — Bill Thomson
*Assistant Examiner* — Younhee Choi
(74) *Attorney, Agent, or Firm* — Ballard Spahr LLP

(57) ABSTRACT

Ultra-high b radial diffusion-weighted imaging signals can be obtained from a selected portion of a nervous system of a subject. At least two ultra-high b radial diffusion-weighted imaging signals for the selected portion of the nervous system of the subject can be compared. The comparison is indicative of changes in the integrity or intactness of a bundle of axons within the selected portion of the nervous system of the subject.

20 Claims, 25 Drawing Sheets

(56) References Cited

OTHER PUBLICATIONS

Rangwala et al. (2013). Diffusion restriction in the human spinal cord characterized in vivo with high b-values STEAM diffusion imaging. NeuroImage. 82:416-425 (Year: 2013).*

Hwang et al. (2003). An image-based finite difference model for simulating restricted diffusion. Magn Reson Med. 50:373-382 (Year: 2003).*

Le Bihan et al. (2013). Apparent Diffusion Coefficient and Beyond: What Diffusion MR Imaging Can Tell Us about Tissue Structure. Radiology. 268:318-322 (Year: 2013).*

Niendorf et al. (1996). Biexponential diffusion attenuation in various states of brain tissue: implications for diffusion-weighted imaging. Magn Reson Med. 36(6):847-57. doi: 10.1002/mrm.1910360607 (Year: 1996).*

Jeong E.K, et al., High-resolution DTI with 2D interleaved multi slice reduced FOV single-shot diffusion-weighted EPI (2D ss-rFOV-DWEPI). Magn. Reson. Med., 54:1575-9 (2005).

Kim, T.H., et al., Diffusion tensor imaging of ex vivo cervical spinal cord specimens: the immediate and long-term effects of fixation on diffusivity, Anat. Rec. (Hoboken). 292: 234-41 (2009).

Klawiter, E.C., et al., Radial diffusivity predicts demyelination in ex vivo multiple sclerosis spinal cords, Neuroimage. 55:1454-60 (2011).

Neuman, C.H., Spin echo of spins diffusing in a bounded medium, J. Chem. Phys. 60: 4508. (1974).

Nilsson, M. , et al., On the effects of a varied diffusion time in vivo: is the diffusion in white matter restricted?, Magnetic Resonance Imaging 27:176-87 (2009).

Rangwala NA, et al., Diffusion restriction in the human spinal cord characterized in vivo with high b-value STEAM diffusion imaging. Neuroimage, 82:416-25 (2013).

Ropele S, et al., Method for quantitative imaging of the macromolecular 1H fraction in tissues. Magnetic Resonance in Medicine 49:864-871 (2003).

Sehy, J.V., et al., Importance of Intracellular Water Apparent Diffusion to the Measurement of Membrane Permeability., Biophysical Journal 83: 2856-2863 (2002).

Soellinger, M, et al., Fast bound pool fraction mapping using stimulated echoes. Magn. Reson. Med., 66:717-24 (2011).

Stanisz, G.J., et al., An analytical model of restricted diffusion in bovine optic nerve, Magn. Reson. Med. 37:103-11 (1997).

Stejskal, E.O. ,et al., Spin Diffusion Measurements: Spin Echoes in the Presence of a Time-Dependent Field Gradient, J. Chem. Phys. 42:288-292 (1965).

U.S. Appl. No. 62/377,032, filed Aug. 19, 2016, Eun Kee (E.K.) Jeong, et al.

* cited by examiner

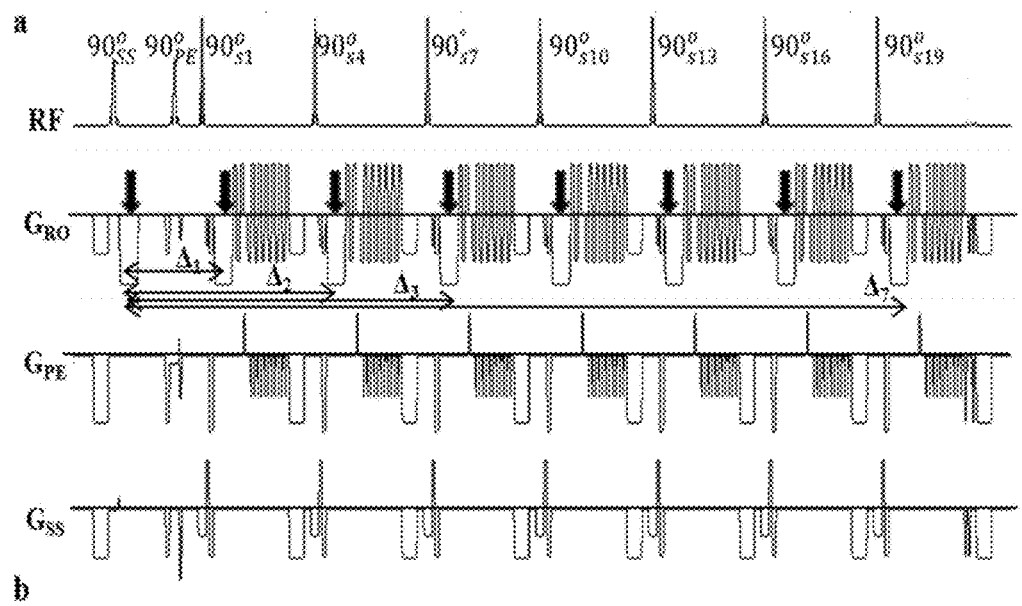
Fig. 1A
Fig. 1B
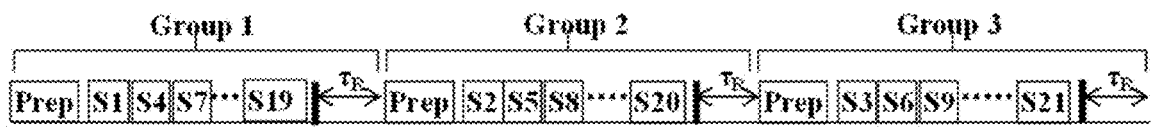
Fig. 2A

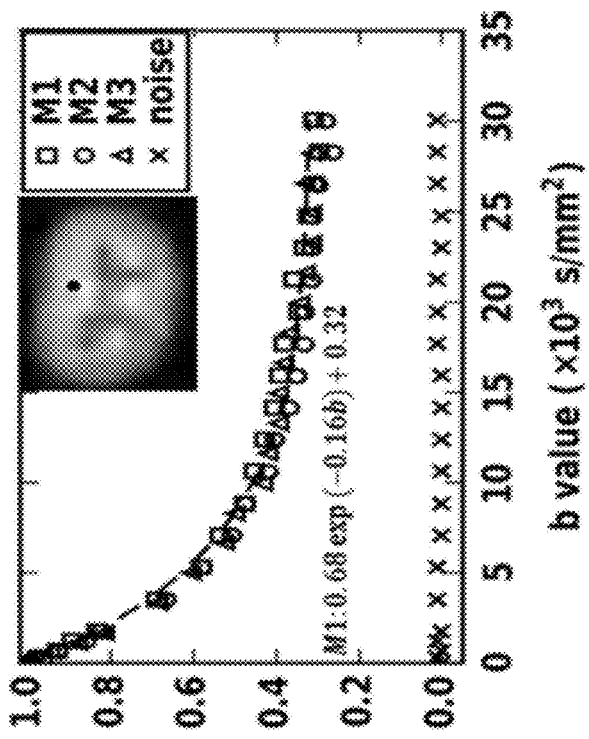
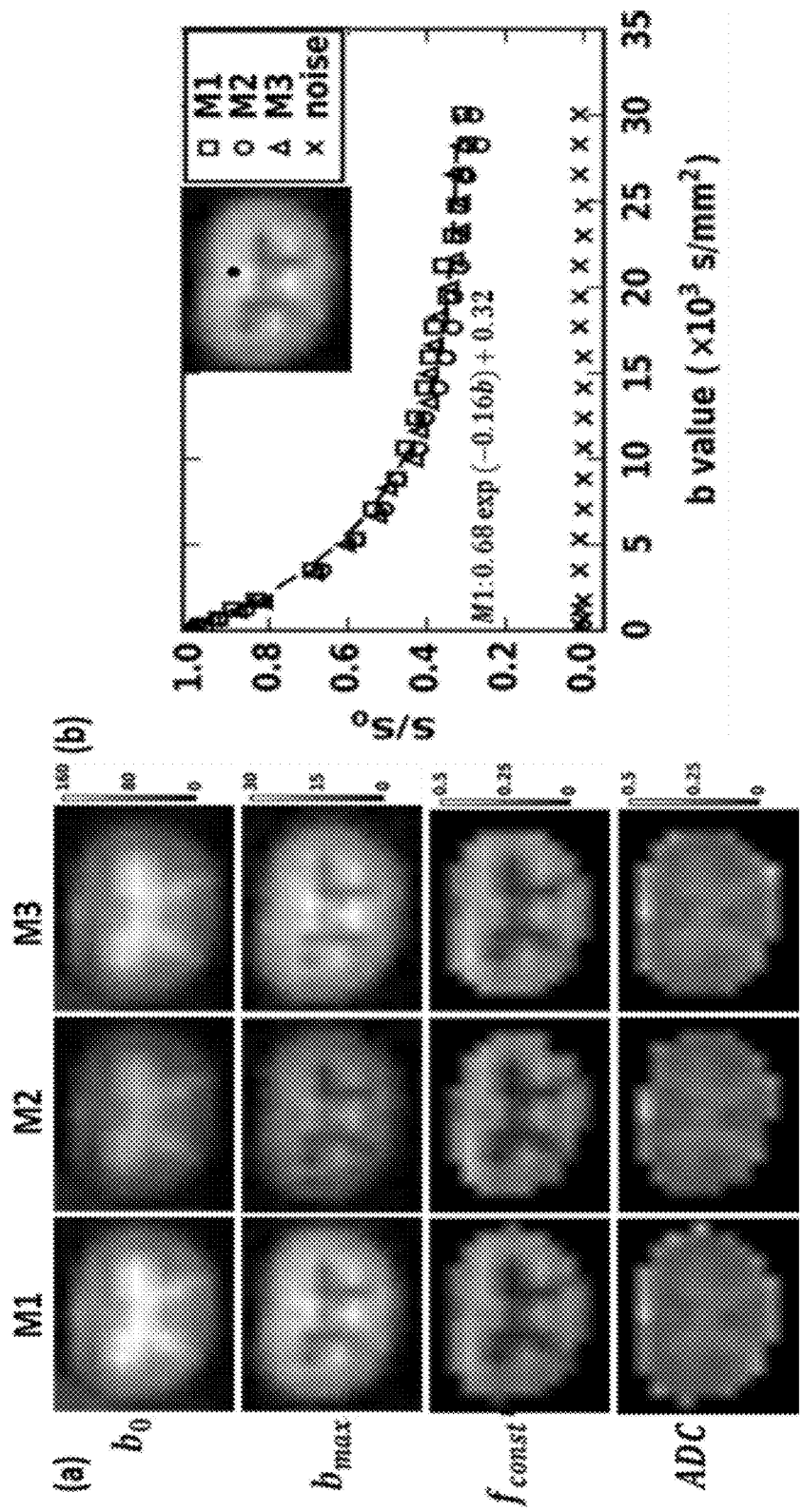
Fig. 8A
Fig. 8B

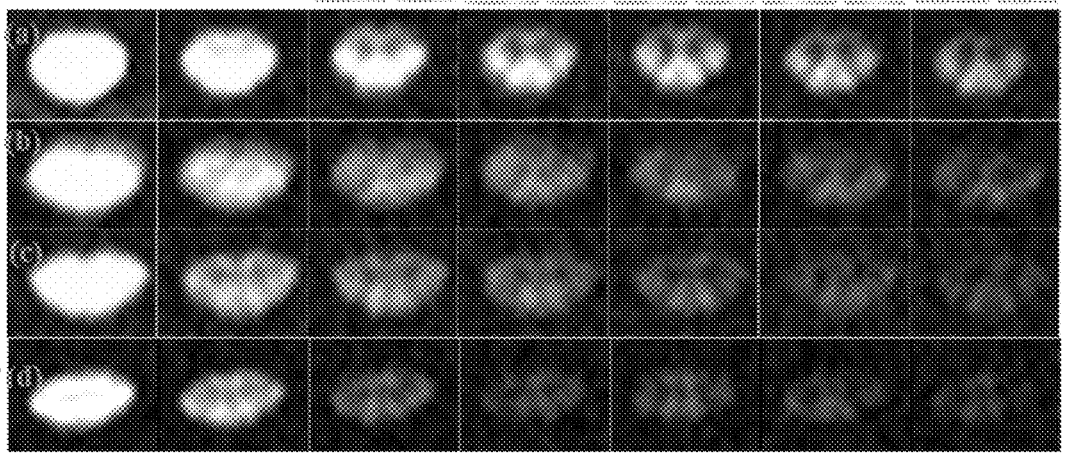

 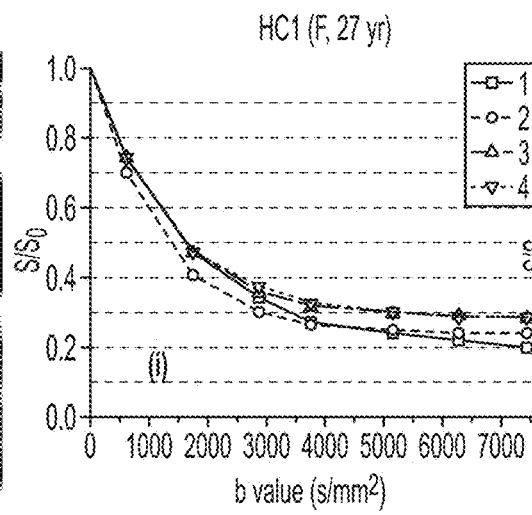 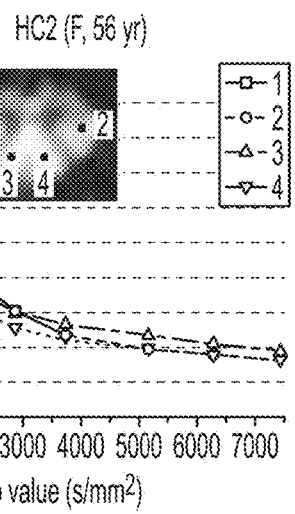
Fig. 18I   Fig. 18J
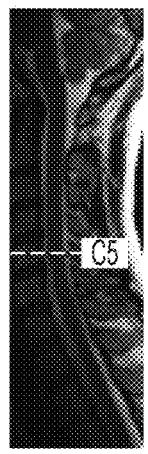 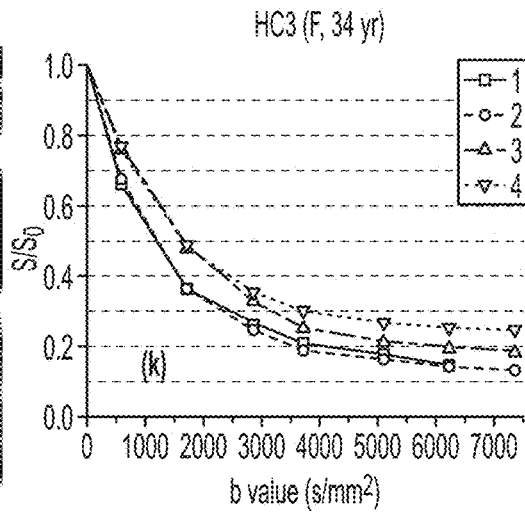 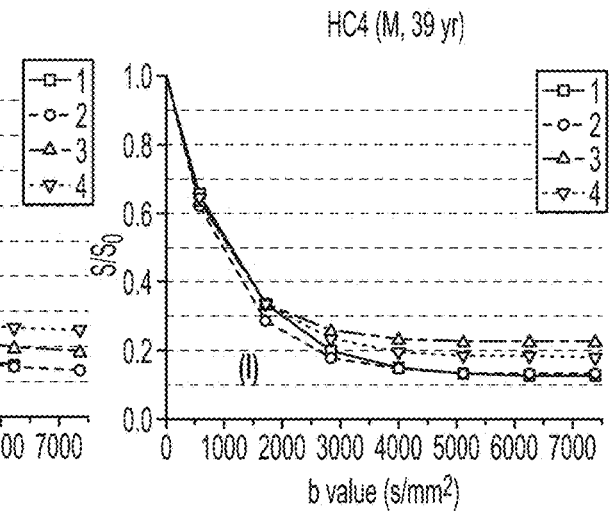
Fig. 18K   Fig. 18L

METHODS AND SYSTEMS OF EVALUATING AXONAL LOSS AND DEMYELINATION

CROSS-REFERENCE TO RELATED APPLICATIONS

This application claims priority to and the benefit of the filing date of U.S. Provisional Patent Application No. 62/377,032, filed Aug. 19, 2016, which application is incorporated herein by reference in its entirety.

BACKGROUND

Quantitative evaluation of spinal cord or optic nerve is important for patient care, particularly for early detection of pathologic change, monitoring the drug treatment in patients, for example in Multiple Sclerosis patients, and prognostic evaluations in patients, for example, in cervical spondylotic myelopathy patients. Currently, however, there is no non-invasive biomarker(s), such as using magnetic resonance imaging, for these purposes.

SUMMARY

Disclosed herein are methods that comprise using an MRI system to obtain ultra-high b radial diffusion-weighted imaging signals from a selected portion of a nervous system of a subject. The selected portion of the nervous system can comprise a bundle of axons and have a restricted region comprising an intra-axonal space positioned within myelinated axons of the bundle of axons and a hindered region comprising an extra-axonal space positioned outside the bundle of axons. The restricted region can be depicted within an imaging pixel obtained by the MRI system. The MRI system can apply a high b-value diffusion-weighting gradient perpendicular to an axonal fiber direction of the bundle of axons. The ultra-high b value diffusion-weighting gradient is sufficient to suppress signals from the hindered region such that the obtained radial diffusion-weighted signals are indicative of the signal from the restricted region. The method can also include using at least one processing unit in communication with the MRI system to compare at least two ultra-high b radial diffusion-weighted imaging signals for the selected portion of the nervous system of the subject. The comparison is indicative of changes in the integrity or intactness of the bundle of axons within the selected portion of the nervous system of the subject.

Also disclosed are systems that comprise at least one processing unit. The at least one processing unit can be configured to (a) apply a high b-value diffusion-weighting gradient during acquisition of ultra-high b radial diffusion-weighted imaging signals from a selected portion of a nervous system of a subject; (b) receive the radial ultra-high b diffusion-weighted imaging signals from the selected portion of the nervous system of the subject, wherein the b-value diffusion-weighting gradient is sufficient to suppress signals from the hindered region such that the obtained radial diffusion-weighted signals are indicative of the signal from the restricted region; and (c) compare at least two ultra-high b radial diffusion-weighted imaging signals for the selected portion of the nervous system of the subject, wherein the comparison is indicative of changes in the integrity or intactness of the bundle of axons within the selected portion of the nervous system of the subject.

Other features and advantages of the present compositions and methods are illustrated in the description below, the drawings, and the claims.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 1A-B are schematic diagrams of 2D ss-DWSTEPI-rFOV. FIG. 1A is a pulse-sequence diagram of 2D ss-DWSTEPI-rFOV. FIG. 1B shows the evolution of magnetization after each RF pulse. In (A), down-pointing arrows represent diffusion gradients $G_D$ and $\Delta_1, \Delta_2, \ldots, \Delta_7$ represent seven diffusion times available for the slice permutation. The length of the arrow in (B) is arbitrary and does not represent the magnitude of magnetization. Imaging schemes for a group of seven slices among 21 total slices are shown.

FIG. 2A is a timing diagram for the slice ordering in 2D ss-DWSTEPI-rFoV imaging with 21 total slices. The prep block ($90°_{SS}$-$G_D$-$90°_{PE}$) prepares magnetization from the total phase and slice FOVs. Images of the slices belonging to group 1 (slices 1, 4, 7, 11, 15, and 19) were acquired subsequently with different $T_M$s. The $\tau_R$(~2 ms) represents recovery time before the magnetization from the same phase, and slice FOVs are prepared to acquire the images of the slices belonging to group 2 and so on.

In FIG. 3C, the dashed lines passing through square symbols and triangle symbols in the plot represent the mono-exponentially fitted curve of $T'_1$-curve and diffusion-curve, respectively. The $T'_1$-curve in (C) is plotted against $T_M$s=9, 85, 161, 237, 313, 389, and 465 ms, but $T_M$s are not displayed in the horizontal axis.

FIGS. 8A-B show the results of the ex vivo UHB-rDWI experiments. FIG. 8A shows DW images with b$_0$ (first row), b$_{max}$ (second row), f$_{const}$ map (third row), and ADC map (fourth row) for three different measurements M1 (first column), M2 (second column), and M3 (third column). FIG. 8B shows the typical signal-b curves from a pixel of WM for the different sets of the imaging parameters given in Table 2. The dashed line in (B) is the MCF of the set M1.

FIGS. 11A-11E show images of a MS patient after an acute attack. (A) Axial gadolinium-enhanced T1WI at day 1 demonstrates an enhancing lesion in the right lateral corticospinal tract. T2WI at day 11 (B) and at day 60 (C) reveal corresponding T2 hyperintense lesions in the right lateral corticospinal tract. The lesion is smaller and more well-defined at day 60 as compared to day 11. (B) A second non-enhancing T2 hyperintense lesion in the left posterior column indicates an old lesion (L2). Fractional anisotropy (FA) fibermaps at day 60 (D,E) show reduced FA values in the right corticospinal lesion within the circle as compared to the contralateral region.

FIGS. 17A-17D show series of b-value images at C3-C4 vertebral level slice in volunteers: (A) HC1, (B) HC2, (C) HC3 and (D) HC4. Clear contrast between white and gray matter is observed at high-b value images.

FIGS. 18A-18L show rDWI signal-b plots of volunteers: (A, E, I) HC1, (B, F, J) HC2, (C, G, K) HC3, and (D, H, L) HC4 at C2-C3, C4, and C5 levels, respectively. The red dotted line on the sagittal image at the left show these levels. Four point ROIs were chosen: two on corticospinal tract (1, 2) and two on posterior columns (3, 4). The plots on the left and right side of the cord within the same section are almost identical.

DETAILED DESCRIPTION

Figure 2B:
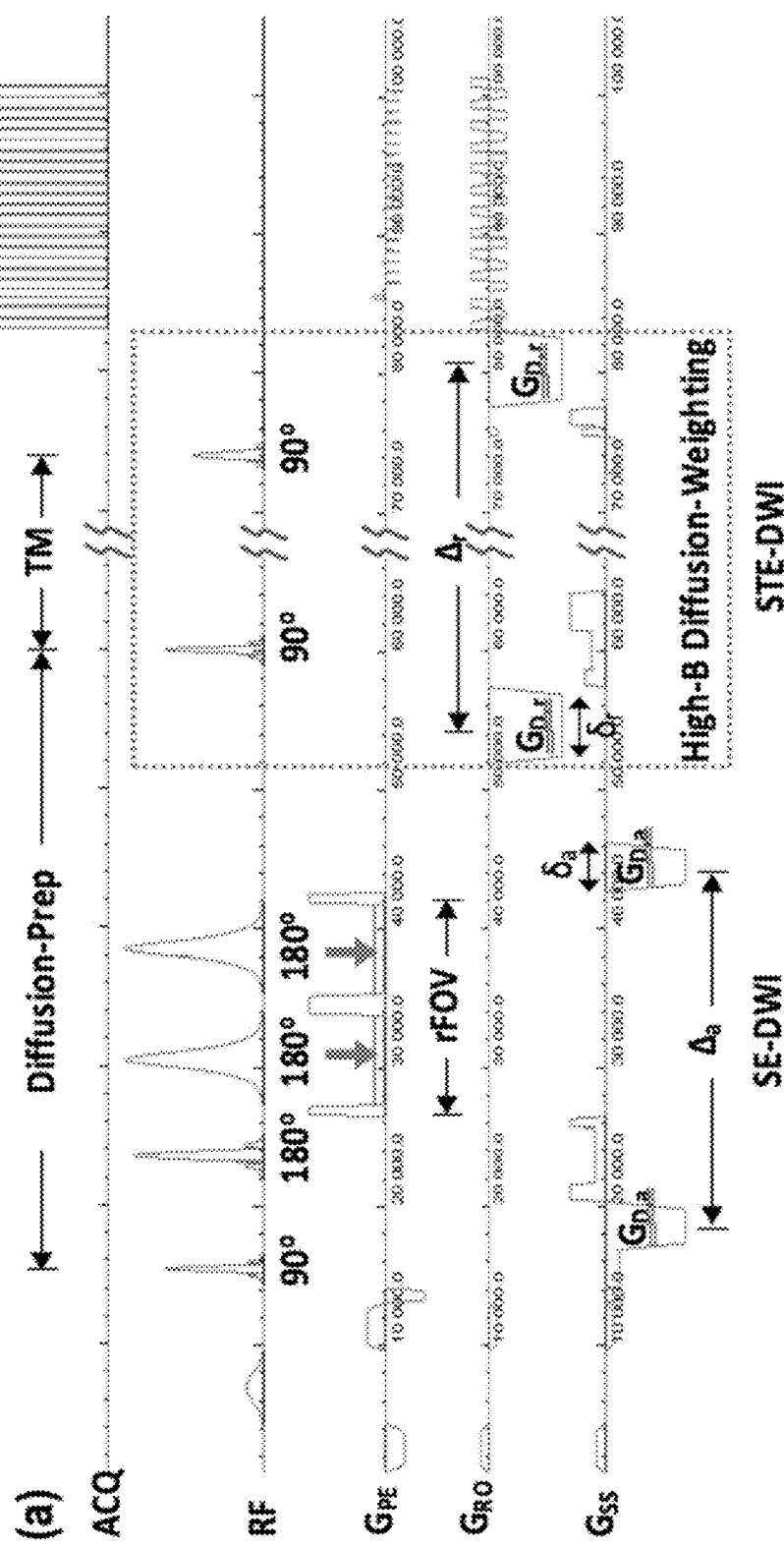
FIGS. 2B-2C show results from an UHB-DWI experiment. 2D ss-DWSTEPI-rFOV consists of spin-echo (SE-DW) for low-b and stimulated-echo DWI (STE-DW) for high-b DWI. The UHb-DWI along the radial direction is accomplished by STE-DW with a pair of diffusion gradients $G_{D,r}$ in radial direction, separated by a long mixing time TM, of which the de-phased longitudinal magnetization undergoes large diffusion-weighting as $M_{z,D_r} \sim e^{-TM/T_1} e^{-b_{se}D_a} e^{-b_{ste}D_r}$ with $b_{se} = (\gamma G_{D,a} \delta_a)^2 (\Delta_a - \delta_a)$ and $b_{ste} = (\gamma G_{D,r} \delta_r)^2 (\Delta_r - \delta_r)$. The long diffusion time sensitizes the water exchange between the IA and EA spaces, based on Monte-Carlo simulation. Reduced-FOV in the phase-encoding direction can be accomplished using either double-inversion/refocusing adiabatic 180° pulses (FIG. 2B) in a system with single Tx channel or 2D excitation RF pulse (FIG. 2C) in system with multiple Tx channels. To measure radial UHB-DWI, only STE-DW was used with SE-DW disabled. For measuring the axial DWI of IA water, SE-DW was measured with varying $G_{D,a}$, while STE-DW was set to a large b to suppress EA water signal. A MRI protocol was set up for IAF and $D_H$ measurements on phantom, the protocol was tested on 5 normal volunteers, and the performance between $D_H$ measurements with constant diffusion time while varying $G_d$ and constant $G_D$ while varying diffusion time was compared.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects.

As used herein, the term "comprising" can include the aspects "consisting of" and "consisting essentially of" "Comprising can also mean "including but not limited to."

Disclosed herein, in various aspects, are systems and methods for quantitative evaluation of the spinal cord and other portions of the nervous system of a subject. Optionally, the disclosed systems and methods can be used to evaluate and monitor the progression of Multiple Sclerosis and other diseases or conditions of a patient.

In exemplary aspects, the disclosed methods include using an MRI system to obtain ultra-high b radial diffusion-weighted imaging (UHb-rDWI) signals from a selected portion of a nervous system of a subject. It is contemplated that the disclosed methods can be applied to subjects having any disease related to an injury of the spinal cord. In one exemplary aspect, the subject can be a patient having multiple sclerosis. In another exemplary aspect, the subject can be a patient having a condition selected from the group consisting of: cervical spondylotic myelopathy (CSM), motor-neuron diseases including amyotrophic lateral sclerosis (ALS), metabolic vitamin B12 deficiency affecting spinal cord, transverse myelitis, transverse myelopathy, neuro myelitis optica, and combinations thereof. In these exemplary aspects, the selected portion of the nervous system comprises a bundle of axons and has a restricted region comprising an intra-axonal space positioned within myelinated axons of the bundle of axons and a hindered region comprising an extra-axonal space positioned outside the myelinated axons of the bundle of axons. In these aspects, the restricted region can be depicted within an imaging pixel obtained by the MRI system. In further exemplary aspects, it is contemplated that the selected portion of the nervous system of the subject can comprise a selected portion of a spinal cord of the subject. Optionally, the selected portion of the nervous system of the subject can comprise a selected portion of a brain of the subject. In another optional aspect, the selected portion of the nervous system of the subject can comprise an optic nerve of the subject.

The MRI system disclosed herein can comprise the components that are conventionally found in MRI systems that are known in the art. Optionally, it is contemplated that the MRI system can be a clinical whole body MRI system, as known in the art. In exemplary aspects, the MRI system can comprise a scanner that is configured to form a strong magnetic field around an area to be imaged as further disclosed herein. In further aspects, the MRI system can comprise at least one receiving coil, which can measure a signal emitted by excited atoms (protons) within the imaged area in response to energy from an oscillating magnetic field. In further aspects, the MRI system can comprise one or more gradient coils that are configured to vary the main magnetic field. It is contemplated that the receiving coils and gradient coils of the MRI system can be selected or optimized for a particular application; however, it is contemplated that any conventional receiving coil or gradient coil can be used, provided it is provided in conjunction with other MRI system components that are capable of performing the methods disclosed herein. Optionally, the MRI system can further comprise at least one processing unit. Additionally, or alternatively, as further disclosed herein, at least one processing unit can be communicatively coupled to (or otherwise positioned in communication with) the MRI system.

In these exemplary aspects, the MRI system can apply a high b-value diffusion-weighting gradient perpendicular to an axonal fiber direction of the bundle of axons. The ultra-high b value diffusion-weighting gradient can be sufficient to suppress signals from the hindered region such that the obtained radial diffusion-weighted signals are indicative of the signal from the restricted region. It is contemplated that the b-value diffusion-weighting can be greater than 4,000 s/mm$^2$ (optionally, greater than 10,000 s/mm$^2$) to suppress water signals from the extra-axonal space.

In further exemplary aspects, the methods also can include using at least one processing unit in communication with the MRI system to compare at least two ultra-high b radial diffusion-weighted imaging signals for the selected portion of the nervous system of the subject. In these aspects, the comparison is indicative of changes in the integrity or intactness of the bundle of axons within the selected portion of the nervous system of the subject. Using the at least one processing unit to compare the at least two ultra-high b radial diffusion-weighted imaging signals can include determining a fraction of restricted water for each radial diffusion-weighted imaging signal and comparing the determined fractions of restricted water for the at least two ultra-high b radial diffusion-weighted signals. The determined fraction of restricted water can decrease between a first radial diffusion-weighted imaging signal and a second, subsequent diffusion-weighted imaging signal. The decrease in the determined fraction of restricted water can be indicative of an exchange of water between the restricted region and the hindered region of the selected portion of the nervous system.

Optionally, using the at least one processing unit, the method can further include determining an intensity of the signal for each radial diffusion-weighted imaging signal and comparing the determined intensities for the at least two radial ultra-high b diffusion-weighted signals. The determined intensities of the at least two ultra-high b radial diffusion-weighted imaging signals can decrease between a first radial diffusion-weighted imaging signal and a second, subsequent diffusion-weighted imaging signal. The decrease in the determined signal intensities can be indicative of an exchange of water between the restricted region and the hindered region of the selected portion of the nervous system.

In further exemplary aspects, using the at least one processing unit to compare the at least two ultra-high b radial diffusion-weighted imaging signals can further comprise calculating a signal decay rate based upon the determined intensities of the at least two ultra-high b radial diffusion-weighted imaging signals. In these exemplary aspects, the method can further include using the at least one processing unit to determine whether the signal decay rate exceeds a threshold value. It is contemplated that a signal decay rate above the threshold value can be indicative of an exchange of water between the restricted region and the hindered region of the selected portion of the nervous system.

In further exemplary aspects, using the at least one processing unit, the method can further include performing a Monte Carlo simulation of water diffusion within the selected portion of the nervous system before obtaining the ultra-high b radial diffusion-weighted imaging (UHb-rDWI) signals from the selected portion of the nervous system of the subject. A model of the simulated water diffusion can be generated, and one or more diffusion parameters of the model of the simulated water diffusion can be determined. The one or more diffusion parameters of the model of the simulated water diffusion can be used to determine the ultra-high b value diffusion-weighting gradient that is applied to the bundle of axons of the selected portion of the nervous system.

Also disclosed herein is a system that comprises at least one processing unit. As further described herein, the at least one processing unit can be configured to apply a high b-value diffusion-weighting gradient during acquisition of ultra-high b radial diffusion-weighted imaging (UHb-rDWI) signals from a selected portion of a nervous system of a subject. It is contemplated that the b-value diffusion-weighting gradient can be greater than 4,000 s/mm$^2$ to suppress water signals from the extra-axonal space. It is further contemplated that the b-value diffusion-weighting gradient can optionally be greater than 10,000 s/mm$^2$. As described above, the selected portion of the nervous system can comprise a bundle of axons and have (i) a restricted region comprising an intra-axonal space positioned within myelinated axons of the bundle of axons—the restricted region can depicted within an imaging pixel obtained by the MRI system; and (ii) a hindered region comprising an extra-axonal space positioned outside the bundle of axons. It is contemplated that the MRI system can apply the b-value diffusion-weighting gradient perpendicular to an axonal fiber direction of the bundle of axons. In further exemplary aspects, the at least one processing unit can be configured to receive the ultra-high b radial diffusion-weighted imaging signals from the selected portion of the nervous system of the subject. The b-value diffusion-weighting gradient can be sufficient to suppress signals from the hindered region such that the obtained radial diffusion-weighted imaging signals are indicative of the signal from the restricted region. In further exemplary aspects, the at least one processing unit can be configured to compare at least two ultra-high b radial diffusion-weighted imaging signals for the selected portion of the nervous system of the subject. In these aspects, the comparison can be indicative of changes in the integrity or intactness of the bundle of axons within the selected portion of the nervous system of the subject.

Optionally, the at least one processing unit can be configured to determine, for each radial diffusion-weighted imaging signal, a fraction of restricted water within the restricted region and compare the determined fractions of restricted water for the at least ultra-high b two radial diffusion-weighted imaging signals. In another aspect, the at least one processing unit can be configured to determine, for each radial diffusion-weighted imaging signal, an intensity of the signal and compare the determined intensities for the at least two ultra-high b radial diffusion-weighted imaging signals. It is contemplated that the at least one processing unit can be further configured to calculate a signal decay rate based upon the determined intensities of the at least two ultra-high b radial diffusion-weighted imaging signals. The at least one processing unit can be further configured to determine whether the signal decay rate exceeds a threshold value, wherein a signal decay rate above the threshold value is indicative of an exchange of water between the restricted region and the hindered region of the selected portion of the nervous system.

As further disclosed herein, a colored parametric map of decay constant (i.e., $D_H$ (b>4,000 s/mm$^2$)) can be used for comprehensive analysis of the change in spinal cord cross section for white-matter and gray-matter.

In further aspects, a colored parametric map of intra-axonal fraction can be used for comprehensive analysis of the change in spinal cord cross section for white-matter.

In further aspects, Monte-Carlo Simulation of water diffusion can be used for planning and simulating measurement and interpreting of measured ultra-high b diffusion-MRI data as disclosed herein.

In still further aspects, a longitudinal measurement of decay constant ($D_H$) can be used to evaluate the disease evolution in white-matter and gray-matter, including demyelination, remyelination, and axonal injury.

As further disclosed herein, in still further aspects, UHb-DW images with constant b-value and variable diffusion time (up to 400 ms) and after T1 decay correction can directly measure the exchange rate at the intra-axonal space and outside, with the exchange rate effectively being the direct measure of demyelination at the axonal wall.

Ultra-High-B radial diffusion-weighted MRI (UHB-rDWI) can probe axonal loss and demyelination in the human spinal cord, particularly in patients with multiple sclerosis (MS) and cervical spondylotic myelopathy (CSM). It is not, however, suitable to measure UHB-rDWI using the conventional 2D ss-DWEPI, which is most widely used DWI technique, because of severe geometric distortion, and excessive signal loss by T2 due to the long echo time (TE). Described herein is a time-efficient data acquisition technique (2D ss-SWSTEPI-rFOV), which solves both problems with increased time efficiency. Also described herein are methods to analyze the UHB-rDWI data with b>4,000 s/mm$^2$, of which signal at ~b=4,000 indicates the axonal density and the signal decay for b>4,000 s/mm$^2$ indicates degree of demyelination.

Quantitative evaluation of spinal cord or optic nerve is important for early detection of pathologic changes, monitoring the drug treatment, and prognostic evaluation in patients. Presently, no non-invasive biomarker is available. Although there is hindered water diffusion due to the membranes inside specific organelles, such as nucleus of which is surrounded by two lipid-bilayers, there is no other structure like myelinated axons with tens of lipid-bilayers. Therefore, no matter how heterogeneous the physical environment is inside the spinal cord white-matter, for the "radial diffusion MRI", white-matter can be compartmentalized into, "restricted" water molecules in intra-axonal space where water cannot move more than diameter of the axon, and "mobile" water in other spaces which water can move over the hindered boundaries including the membranes. At sufficiently high diffusion-weighting, for example, b>~4,000 s/mm$^2$ using a clinical MRI system, diffusion-weighted MRI (DWT) signal from "mobile" water protons in EA and myelin space can be completely suppressed down to background noise level, which leaves the signal contributed from TA water. As described herein, this effect on the behavior of UHB-rDWl has been observed in all in vivo human CSC tested. Although there may be other structures in which the water molecule are also restricted as seen for radial diffusive motion in the axon, this signal in clinical UHB-rDWT won't be resolved in-vivo human CSC because of insufficient signal-to-noise ratio (SNR). The methods disclosed herein can be used to quantitatively evaluate spinal cord injury, such as, in multiple sclerosis and cervical spondylotic myelopathy. As also described herein, are imaging methodologies that take advantage of restricted diffusion of the water molecules in intra-axonal (IA) space to detect fractions of intra- and extra-axonal spaces, and a decay rate constant of the ultra-high-8 radial DWI (UHB-rDWI) signal intensity that can represent the degree of demyelination. Described herein are data acquisition methods: 2D single shot diffusion-weighted stimulated-EPI with reduced field of view (2D ss-DWSTEPI-rFOV); CSC dedicated RF coil, which has optimum signal-to-noise ratio at specific depths (~6 cm) where the typical spinal cord is positioned; data processing software to analyze the high-B DWI; and transmit-receive switch to image a specimen using a clinical MRI system. This method has been validated using a developed specimen MRI RF coil with a transmit-receive switch, that includes a printed-circuit-board (PCB). This TR switch can be used for MRI of small animal or specimen using a whole body clinical MRI system.

Diffusion MRI is considered as the best quantitative imaging technique that can probe pathology in the spinal cord. Its output, however, is not objective for white-matter nerve because of the different contribution in the measured signal intensity from waters in the intra- (IA) and extra-axonal spaces. Using the ultra-high-b DWI, the IA signal (IAF) can be separated from the total signal, and its decay rate constant (DH) can be measured. These IAF and DH can be used as biomarkers to evaluate the axonal damage and demyelination, respectively. The conventional spin-echo based diffusion-weighted MRI technique is not suitable for spinal cord DWI because of too much distortion and too much signal decay. The time efficiency is also poor when measuring DH using conventional diffusion-weighted stimulated MRI. The methods disclosed herein, 2D ss-DWSTEPI-rFOV (2D single shot Diffusion-Weighted STimulated-EPI with reduced Field of View), can solve these problems and generate ultra-high-b DWT with reduced geometric distortion, free of motion artifact, and improved time-efficiency. Because the diffusion-weighting (b-factor) can be varied by varying the minting time (TM) in 2D ss-DWSTEPI-rFOV, the T1 decay effect can be removed using an extra measurement with b=0. For the application of UHB-DWl for cervical spinal cord, a dedicated CSC rF coil can be used, of which the signal-to-noise ratio (SNR) can be optimized at the depth of ~6 cm. Further, a numerical simulation algorithm was developed using Python language.

These methods described herein can be used for the quantitative evaluation of injury in spinal cord of patients with multiple sclerosis or cervical spondylotic myelopathy, or optic nerve in patients with optic neuritis. The measured value can also be used for early detection of pathologic change, monitoring of drug treatment, and prognostic evaluation of surgery in CSM patients.

EXEMPLARY SYSTEMS AND METHODS

It is contemplated that any content described in the following examples can be used to form an aspect of the disclosed systems and methods. Although described as separate examples, it is contemplated that particular parameters or steps of one example can be combined with parameters and steps of any other examples disclosed herein to produce additional aspects of the disclosed systems and methods. Thus, except as otherwise indicated, it is contemplated that steps or features of Example 1 can be combined with steps or features of one or more of Examples 2-4. Similarly, except as otherwise indicated, it is contemplated that steps or features of Example 2 can be combined with steps and features of one or more of Examples 1 and 3-4. Further, except as otherwise indicated, it is contemplated that steps or features of Example 3 can be combined with steps and features of one or more of Examples 1-2 and 4. Still further, except as otherwise indicated, it is contemplated that steps or features of Example 4 can be combined with steps and features of one or more of Examples 1-3.

Example 1: Two-Dimensional Single-Shot Diffusion-Weighted Stimulated EPI with Reduced FOV for Ultra-High-b Radial Diffusion-Weighted Imaging of Spinal Cord High-resolution diffusion-weighted imaging (DWI) of the spinal cord (SC) is problematic because of its small cross-section and the large field inhomogeneity. Obtaining the ultra-high-b DWI poses a further challenge. The purpose of this study was to design and validate 2D single-shot diffusion-weighted stimulated echo planar imaging with reduced field of view (2D ss-DWSTEPI-rFOV) for ultra-high-b radial DWI (UHB-rDWI) of the SC.

A time-efficient 2D ss-DWSTEPI-rFOV sequence was developed based on the stimulated echo sequence. Reduced-phase field of view was obtained by using two slice-selective 90° radiofrequency pulses in the presence of the orthogonal slice selection gradients. The sequence was validated on the phantom and demonstrated on the SC imaging.

The results show that Ultra-high-b radial diffusion-weighted ($b_{max}$=7,300 s/mm$^2$) images of the SC with greatly reduced distortion were obtained. The exponential plus constant fitting of the diffusion-decay curve estimated the constant fraction (restricted water fraction) as 0.36±0.05 in the SC white matter. Thus, the 2D ss-DWSTEPI-rFOV sequence has been designed and demonstrated for high-resolution UHB-rDWI of localized anatomic structures with significantly reduced distortion in comparison with conventional 2D ss-DWSTEPI.

A. Introduction

Magnetic resonance imaging (MRI) is commonly used for spinal cord (SC) imaging because of its high soft-tissue contrast and non-invasiveness; however, the conventional MRI techniques such as $T_1$- and $T_2$-weighted imaging are generally unable to detect lesions in early stages. An advanced imaging technique, diffusion tensor imaging (DTI), has emerged and expanded as a robust technique for the evaluation of a variety of SC diseases such as multiple sclerosis and SC injury. The axial and radial diffusivities obtained from the DTI have been increasingly utilized as potential surrogate measures of axon and myelin injuries. Unfortunately, the diffusivity measures derived from the DTI are sometimes not consistent and successful at detecting abnormalities. Use of another advanced MRI technique, high-B diffusion-weighted imaging (DWI), has been evolving for neural tissues imaging because it provides enhanced contrast between white matter (WM) and gray matter (GM) and detects additional subtle WM lesions. Ultra-high-b radial DWI (UHB-rDWI), i.e., DWI with the ultra-high-b diffusion-weighting in the direction perpendicular to the fibers, can be used to estimate the restricted compartment in WM, which may be considered as a biomarker for the characterization of the WM. A previous report (Rangwala N A, Hackney D B, Dai W, Alsop D C; Diffusion restriction in the human spinal cord characterized in vivo with high b-value STEAM diffusion imaging. Neuroimage 2013; 82:416-25), which was based on Monte-Carlo simulation and UHB-rDWI experiments in ex-vivo SC WM, demonstrated that the signal from restricted space (axonal) remains almost constant while signal from hindered space (outside of axons) decays with increasing b-value. The Monte Carlo simulation indicated that the total signal (sum of the signals from the restricted and hindered spaces) remains constant for b values greater than 5,000 s/mm$^2$ as the signal from the hindered space dies out completely at about b=5,000 s/mm$^2$. The constant signal measured in the ultra-high-b region (b>5,000 s/mm$^2$) may be used to characterize the WM.

Although ultra-high-b DWI of the SC can provide valuable information to evaluate WM, obtaining ultra-high-b DWI with b-value greater than 5,000 s/mm$^2$ can be challenging using the conventional diffusion-weighted spin echo (DWSE) acquisition technique. Because of the limited gradient strength in most clinical MRI systems, ultra-high-b DWI requires long echo-time, $T_E$. For instance, $T_E$ of 133 ms is required to achieve b=4,000 s/mm$^2$ with gradient strength 40 mT/m using diffusion-weighted (DW) TRSE (twice-refocused spin-echo) in a current whole-body MRI system. Therefore, DWSE imaging is not suitable for UHB-rDWI. To overcome the problem of the signal loss due to long $T_E$ in DWSE imaging, diffusion-weighted stimulated echo (DWSTE) imaging has been used for UHB-rDWI. DWSTE imaging is suited for tissues with $T_1$>>$T_2$ and short $T_2$ compared with $T_E$, such as muscle and cartilage. DWSTE imaging becomes beneficial over DWSE imaging at high field (>3T), because the $T_2$ of water protons decreases and $T_1$ increases as the field increases. Fixation of tissues further lowers the value of $T_2$ and decreases the diffusivity. Therefore, DWSTE may also be beneficial in ultra-high-b DWI of ex-vivo tissue. DWSTE imaging is also important where the validation of short gradient pulse (SGP) approximation, i.e., short diffusion pulse and long diffusion time, is required, such as q-space and AxCaliber imaging.

High-resolution DWI of the SC can be problematic because of its small cross-section and the large field inhomogeneity in the static field ($B_0$) created by the magnetic susceptibility change at the tissue-bone interfaces. The field inhomogeneity induces distortion in the conventional 2D single-shot diffusion-weighted EPI (2D ss-DWEPI) images, and the distortion increases with increased spatial resolution. The distortion can be reduced by effectively reducing the field of view (FOV) in the phase-encoding direction, thereby reducing the off-resonance induced artifacts. However, reducing phase FOV smaller than object size in the phase-encoding direction induces a wraparound artifact in the image. To overcome this problem of a wraparound artifact caused by reduced-phase FOV, several methods such as 2D radiofrequency (RF) excitation along with 180° refocusing, zoom-EPI, outer volume suppression, and double 180° refocusing along the phase-encoding direction have been proposed for the DWSE imaging. However, no reduced-phase FOV technique has been implemented in DWSTE imaging. For reliable DWI of SC, the source DW images must also be free from motion-induced artifact, which requires a single-shot acquisition such as ss-DWEPI.

Disclosed herein is a time-efficient acquisition single-shot DW stimulated EPI with reduced-phase FOV (2D ss-DW-STEPI-rFOV) based on the STE sequence proposed by Soellinger et al. (Soellinger M, Langkammer C, Seifert-Held T, Fazekas F, Ropele S. Fast bound pool fraction mapping using stimulated echoes. Magn. Reson. Med. 2011; 66:717-24.). Further improvement on the previous design was made by grouping the slices into three interleaved groups. The variation in b-value is obtained by varying the mixing time (~diffusion time). The new sequence was validated on the phantom and demonstrated on human cervical spinal cord (CSC) imaging.

B. Methods

Pulse Sequence Description.

The schematic diagram of 2D ss-DWSTEPI-rFOV is shown in FIG. 1A, which was previously described (Jeong E-K, Kim S-E, Guo J, Kholmovski E G, Parker D L. High-resolution DTI with 2D interleaved multislice reduced FOV single-shot diffusion-weighted EPI (2D ss-rFOV-DWEPI). Magn. Reson. Med. 2005; 54:1575-9). In brief, the reduced FOV in the phase-encoding direction was obtained by using two slice-selective 90° RF pulses in the presence of the orthogonal slice selection gradients ($G_{SS}$). The evolution of magnetization in the 2D ss-DWSTEPI-rFOV is depicted in FIG. 1B. First, the $90°_{SS}$ RF pulse with the $G_{SS}$ in the slice direction flips the longitudinal magnetization within the entire imaging volume to the transverse plane, and then the $90°_{PE}$ RF pulse with the $G_{SS}$ in the phase-encoding direction prepares the magnetization from the entire slice but limited phase FOVs (light gray region in FIG. 1B). After the $90°_{PE}$ RF pulse, $90°_{S1}$, $90°_{S4}$, ..., $90°_{S19}$ RF pulses with the $G_{SS}$ in the slice direction were applied at the different mixing times, respectively, to the slices 1, 4, ..., 19 (dark gray region in FIG. 1B) to flip the prepared magnetization down to the transverse plane.

The slice ordering scheme is based on a technique for measuring bound-pool water fraction. The entire slices are divided into three interleaved groups as shown in FIG. 2A. The experiment is repeated n times (number of slices per group) permuting the slice orders such that all $T_M$s are measured for each slice. Generally, RF pulses ($90°_{S1}$, $90°_{S4}$, ..., $90°_{S19}$, ...) are not perfectly rectangular in the frequency domain, and the RF pulse applied for a particular slice may also affect magnetization of the neighboring slices, which causes an unnecessary signal drop in the measurement and hence introduces error in the quantification. Therefore, the multi-slice group is important to avoid the RF leaking into the adjacent slices. The multi-slice group is also important in the imaging of more than 10 slices to keep the values of $T_M$ in the range of 0-500 ms; otherwise, $T_M$ would be significantly long. For instance, the values of $T_M$ without multi-slice grouping ranges from 0 to 700 ms for 10 slices, 0 to 1,000 ms for 15 slices, and 0 to 1,500 ms for 21 slices, and hence the signal mostly decays due to $T_1$ decay. Three nonselective 90° pulses may also be applied at the end of each slice group (not shown in figure) to saturate all longitudinal magnetization to remove error caused by different $T_1$ recovery for different slices at different $T_M$s.

Correction for $T_1$ Decay.

The longitudinal magnetization, which is prepared and restored by the first two 90° RF pulses as shown in FIG. 1, undergoes an exponential decay of $1/T_1$ during the mixing time $T_M$ even without diffusion weighting. The exchange between the free- and bound-pool water molecules further increases the decay with additional rate η. Therefore, the apparent decay rate becomes $$\frac{1}{T_1'} = \frac{1}{T_1} + \eta.$$

The multiple b-value DW images were acquired by increasing mixing time ($T_M$). As the b-value is increased by increasing $T_M$, the signal decays due to $T'_1$ decay as well as diffusion decay ($T'_1$-diffusion decay) as given by equation $$S_{T'_1-diff} = S_o \exp(-bD)\exp\left(-\frac{T_M}{T'_1}\right) \quad [1]$$

where $S_o$ is the signal measured without $T'_1$ and diffusion decay, $$b = \gamma^2 G_D^2 \delta^2 \left(\Delta - \frac{\delta}{3}\right);$$

γ is a gyromagnetic ratio, and $G_D$, δ, and Δ are the amplitude, duration, and separation of the diffusion-weighting gradient pair. $T_2$ decay is included in $S_o$ and is constant for all b-values because $T_E$ is fixed for all b-values.

In the absence of diffusion weighting, the signal decays due to only the $T'_1$ decay and is given by the equation $$S_{T'_1} = S_o \exp\left(-\frac{T_M}{T'_1}\right) \quad [2]$$

The effect of $T'_1$ decay from the $T'_1$-diffusion decay can be removed by dividing the signal measured with diffusion weighting by the signal measured without diffusion weighting at the same $T_M$. The signal decays due to only the diffusion decay can be obtained by dividing Eq. [1] by Eq. [2] and is given by the equation $$S_{diff} = \exp(-bD) \quad [3]$$

where $S_{diff}=S_{T'_1-diff}/S_{T'_1}$ is the signal measured at a particular b-value under pure diffusion decay.

The signal decay curves measured with and without diffusion weighting are, respectively, termed as $T'_1$-diffusion-curve and $T'_1$-curve. The $T'_1$-diffusion-curve undergoes $T'_1$ decay as well as diffusion decay whereas the $T'_1$-curve undergoes only $T'_1$ decay. When the $T'_1$-diffusion-curve is divided by the $T'_1$-curve measured for the same values of $T_M$, the new curve termed as diffusion-curve is obtained, which undergoes the diffusion decay. Dividing the $T'_1$-diffusion-curve by the $T'_1$-curve often introduces fluctuations into the diffusion-curve, particularly at the ultra-high-b signal, where the signal-to-noise ratio is low. Therefore, to get a smooth diffusion-curve, the $T'_1$-curve is first fitted with an appropriate fitting function, for instance, a mono-exponential function in phantom imaging, where the water molecules have a single $T_1$ value with η=0, and bi-exponential function in human SC in-vivo imaging, and the $T'_1$-diffusion curve is divided by the fitted $T'_1$-curve.

MRI Experiments.

Imaging studies of the 2D ss-DWSTEPI-rFOV pulse sequence were performed on a 3T clinical MRI system (Trio, Siemens Medical Solutions, Erlangen, Germany) equipped with maximum gradient strength of 40 mT/m and gradient slew rate of 200 mT/m/s. The pulse sequence was developed using the Integrated Development Environment for Applications (IDEA) pulse sequence development environment.

Phantom Experiment.

Axial images of a cylindrical phantom filled with saline, doped with 0.1 mM $MnCl_2$, were acquired using 2D ss-DWSTEPI-rFOV at room temperature. The following imaging parameters were used: $T_E$=64 ms, $T_R$=3.0 s, read FOV=256 mm, phase FOV=88 mm, slice thickness=4 mm, number of slices=21, acquisition matrix=128×44. Seven different b-values ($b_{max}$=591 s/mm$^2$) were obtained by applying the constant diffusion gradient (duration–δ=12 ms and strength–$G_D$=11 mT/m) along the read-out direction for the seven different $T_M$s ranging from 9 to 465 ms. The $b_0$ (b=0 s/mm$^2$) images were also obtained without diffusion weighting for the corresponding $T_M$s. Total imaging time for both $b_0$ and DW images was 10 minutes, 30 seconds.

In-Vivo Experiment.

After approval was obtained from the Institutional Review Board, in-vivo imaging of a volunteer (e.g., a subject) who provided informed consent was performed. The 2D ss-DWSTEPI-rFOV technique was used to acquire axial DW images of the CSC using a home-built eight-channel, receive-only CSC array. The imaging parameters used were the same as those for the phantom studies except read FOV=128 mm, phase FOV=44 mm, and b values in the range of 0-7300 s/mm$^2$ were used. Seven different b-values ($b_{max}$=7,300 s/mm$^2$) were obtained by applying the constant diffusion gradient (δ=12 ms and $G_D$=38 mT/m) along the read-out direction (radial DWI) for seven different $T_M$s ranging from 9 to 465 ms. The $b_0$ images were also obtained without diffusion weighting for the corresponding $T_M$s.

Figure 2C:
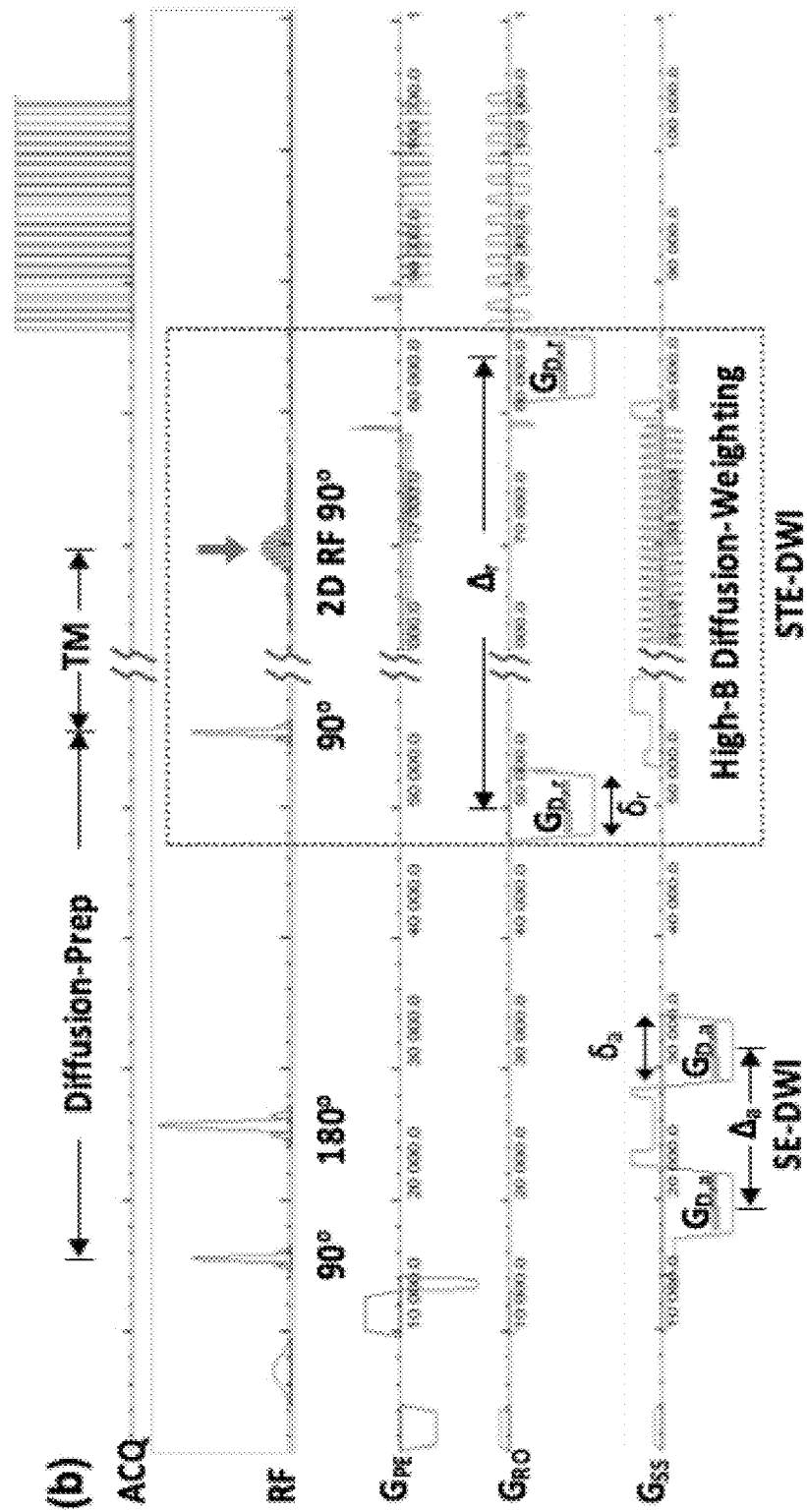

2D ss-DWSTEPI-rFOV to Measure Water Exchange Rate Between Two Compartments:

UHB-DWI was developed and tested, as shown in FIGS. 2B-2C. 2D ss-DWSTEPI-rFOV consists of spin-echo (SE-DW) for low-b and stimulated-echo DWI (STE-DW) for high-b DWI. The UHb-DWI along the radial direction was accomplished by STE-DW with a pair of diffusion gradients $G_{D,r}$ in radial direction, separated by a long mixing time TM, of which the dephased longitudinal magnetization undergoes large diffusion-weighting as $M_{z,D_r}=\sim e^{-TM/T_1}e^{-b_{se}D_a}e^{-b_{ste}D_r}$ with $b_{se}=(\gamma G_{D,a}\delta_a)^2(\Delta_a-\delta_a)$ and $b_{ste}=(\gamma G_{D,r}\delta_r)^2$ $(\Delta_r-\delta_r)$. The long diffusion time sensitized the water exchange between the IA and EA spaces, based on Monte-Carlo simulation. Reduced-FOV in the phase-encoding direction, which reduces the geometric distortion, was accomplished using either double-inversion/refocusing adiabatic 180° pulses (FIG. 2B) in system with single Tx channel or 2D excitation RF pulse (FIG. 2C) in system with multiple Tx channels. To measure radial only STE-DW was used with SE-DW disabled. For measuring the axial DWI of IA water, SE DW was measured with varying $G_{D,a}$, while STE-DW was set to a large b to suppress EA water signal. A MRI protocol was set up for IAF and $D_H$ measurements on phantom, the protocol was tested on 5 normal volunteers, and the performance between $D_H$ measurements with constant diffusion time while varying $G_d$ and constant $G_D$ while varying diffusion time was compared.

C. Results

Phantom Experiment.

Figures 3A, 3B, 3C:
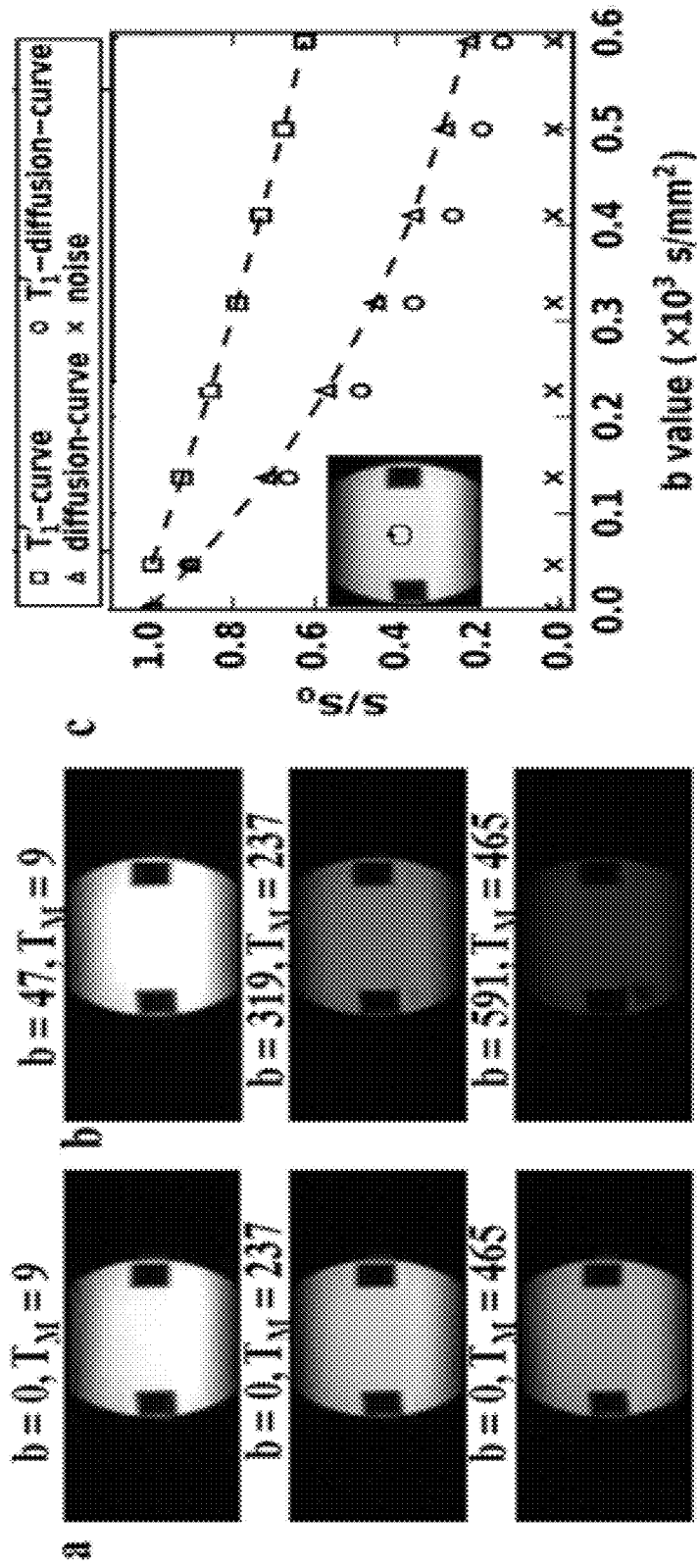
FIGS. 3A-C shows phantom imaging: (A) $b_0$ images; (B) DW images; and (C) typical signal decay curves ($T'_1$-curve, $T'_1$-diffusion-curve, and diffusion-curve) obtained from a ROI.

The $b_0$ and DW images obtained from the phantom using the DWSTEPI-rFOV technique for different $T_M$s (i.e., 9, 237, and 465 ms) are shown in FIGS. 3A and 3B, respectively. A typical $T'_1$-curve obtained from a region of interest (ROI) of the $b_0$ images is shown in FIG. 3c. The $T'_1$-curve was fitted with the mono-exponential function (Eq. [2]). The mono-exponential fitting of the $T'_1$-curve estimated the value of $T'_1$ as 976±2 ms. A typical $T'_1$-diffusion-curve obtained from a ROI of the DW images is also shown in FIG. 3C. The diffusion-curve, which undergoes the diffusion decay, was obtained by dividing the $T'_1$-diffusion-curve by the fitted $T'_1$-curve and is also shown in FIG. 3C. The diffusion of the water molecules in the phantom is free diffusion, and hence the signal decay due to diffusion of molecules are mono-exponential (Eq. [3]). The diffusion-curve was fitted with the mono-exponential function. The mono-exponential fitting of the diffusion-curve estimated the diffusivity of the water molecules as $(2.51±0.03)×10^{-3}$ mm$^2$/s.

In-Vivo Experiment.

Figure 4A:
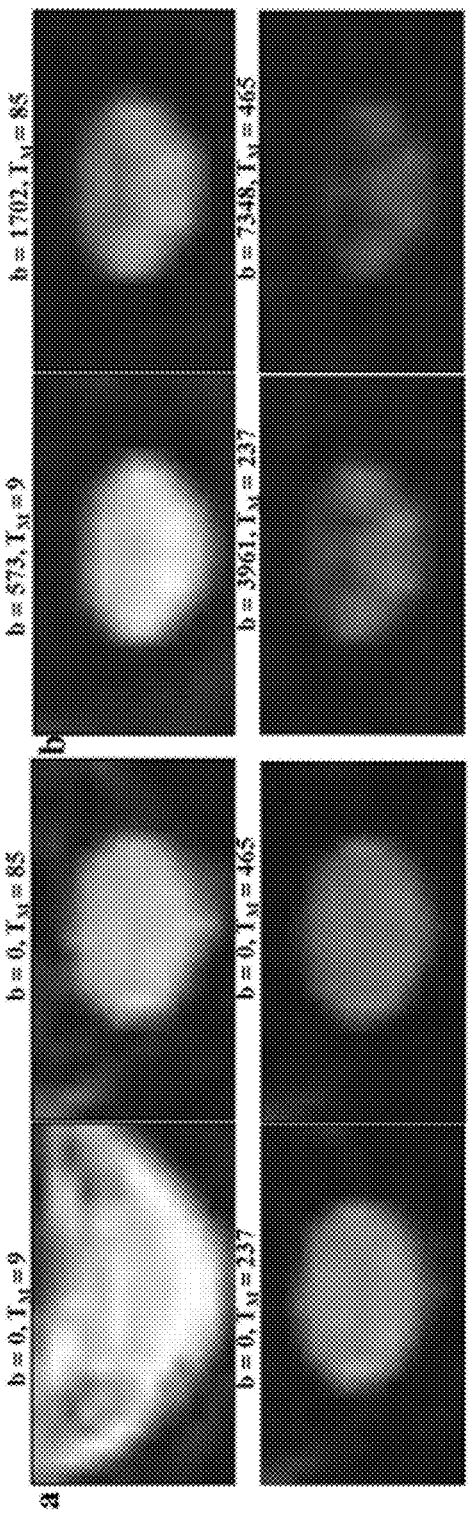
FIGS. 4A-D show In-vivo imaging: (A) $b_0$ images, (B) DW images, and (C-D) typical signal decay curves ($T'_1$ decay, $T'_1$ diffusion decay, and diffusion decay) from WM and GM pixels of the CSC at C3 vertebra level, respectively. Dashed lines in (C-D) represent the bi-exponential fitting of the $T'_1$-curve (dashed line passing through the square symbols) and exponential plus constant fitting of the diffusion-decay curve (dashed line passing through the triangle symbols). T'$_1$-curves in (C-D) are plotted against T$_M$s=9, 85, 161, 237, 313, 389, and 465 ms, but T$_M$s are not displayed in the horizontal axis.
Figure 4B:
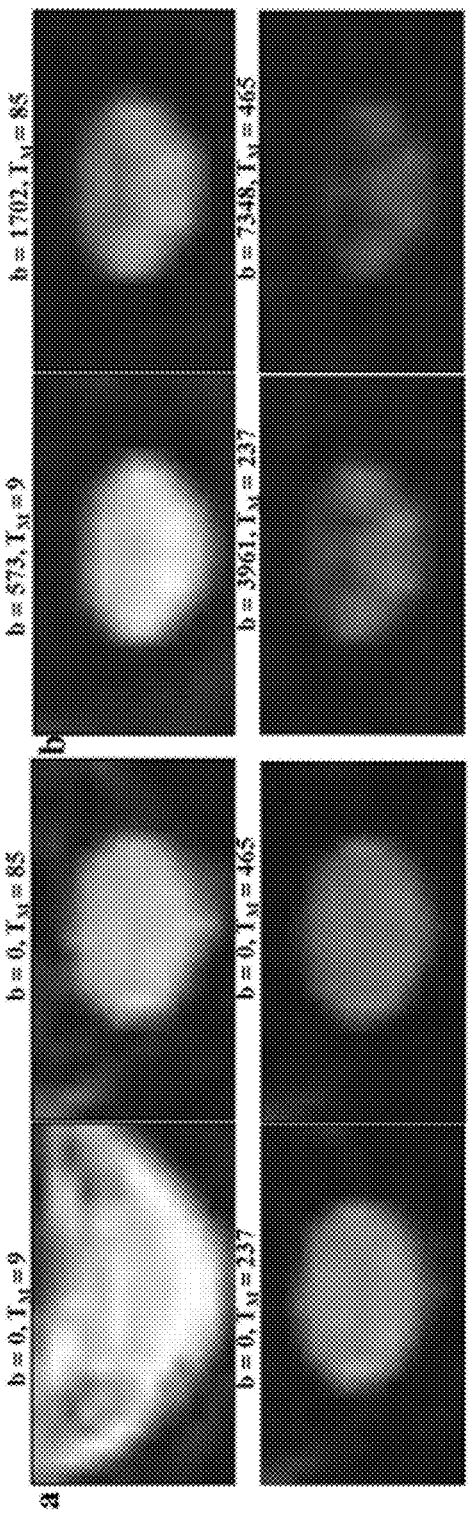
Figure 4C:
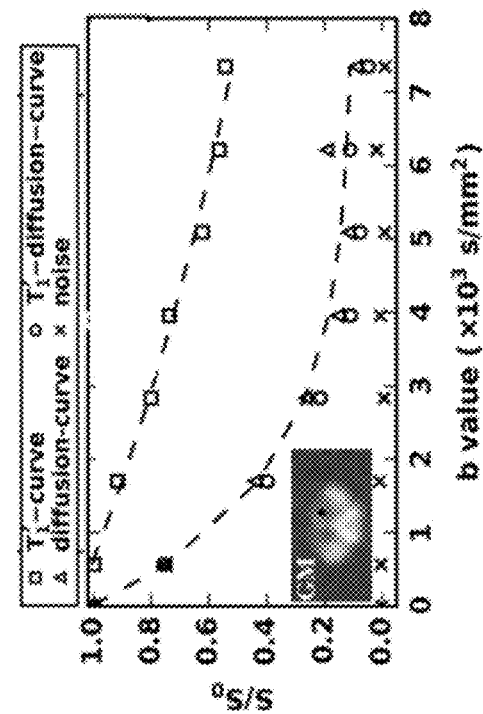
Figure 4D:
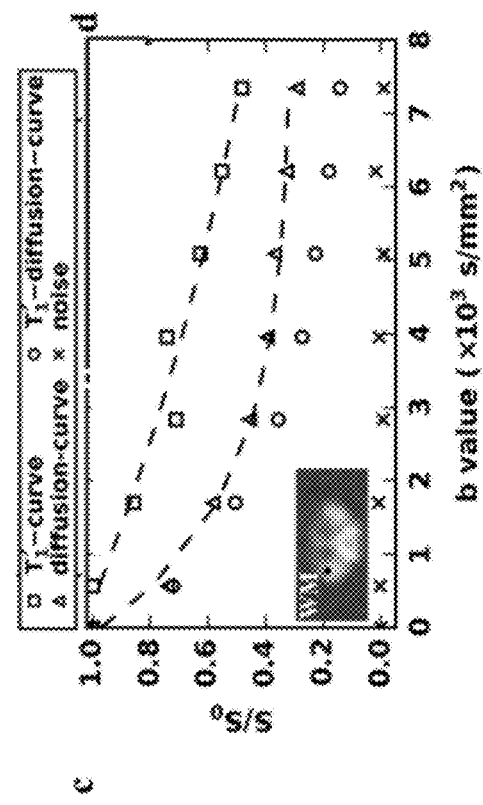
Figure 5:
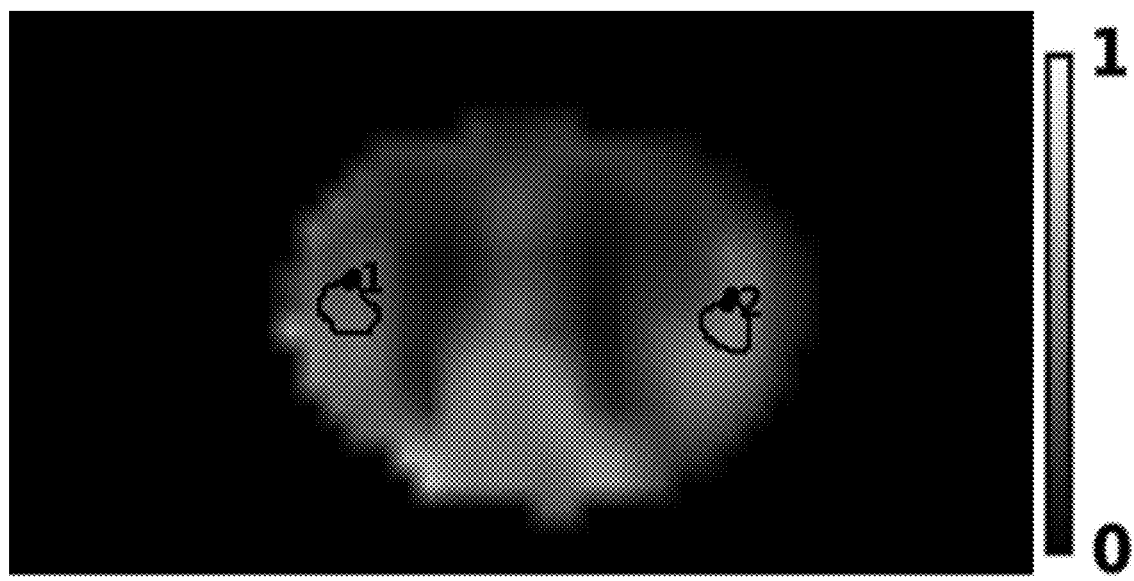
FIG. 5 shows the restricted water fraction map for an axial slice of the CSC at the level of the C3 vertebra.

The in-vivo b0 images and DW images of the human CSC obtained using the DWSTEPI-rFOV sequence for different values of TMs are shown in FIGS. 4A and 4B, respectively. Typical $T'_1$-curves obtained from WM and GM pixels (1×1×4 mm3) of the CSC at the C3 vertebra level are shown in FIGS. 4C and 4D, respectively. The $T'_1$-curves were fitted with the bi-exponential function (Soellinger M, Langkammer C, Seifert-Held T, Fazekas F, Ropele S. Fast bound pool fraction mapping using stimulated echoes. Magn. Reson. Med. 2011; 66:717-24). Typical $T'_1$-diffusion-curves obtained from a WM and GM pixels (1×1×4 mm3) of the CSC at the level of C3 vertebra are also shown in FIGS. 4C and 4D, respectively. The diffusion-curve for each WM and GM pixel, which undergoes the diffusion decay, was obtained dividing the corresponding $T'_1$-diffusion-curve by the fitted $T'_1$-curve and are also shown in FIGS. 4C and 4D. The radial DW signal measured in WM is mainly the sum of the constant signal from the restricted space (axonal) and approximately mono-exponentially decaying signal from hindered space; therefore, the radial diffusion-curve may be fitted with exponential plus constant fitting function. The exponential plus constant fitting of the diffusion-curve estimated the constant fraction as 0.32±0.03 in a WM pixel with the decaying fraction and diffusivity, respectively, as 0.68±0.02 and (0.55±0.08)×10−3 mm2/s. The constant fraction in the exponential plus constant fitting may represent fraction of restricted water (axonal fraction) in the WM. The map of the restricted water fraction obtained from a 4-mm-thick slice (C3) is shown in FIG. 5. The average values of the fraction measured in ROIs shown in FIG. 5 were 0.36±0.05 (ROI1) and 0.37±0.08 (ROI2) in lateral WM columns.

D. Discussion

The diffusivity of the water molecules in the phantom was estimated as $(2.51\pm0.03)\times10^{-3}$ mm$^2$/s, which is slightly higher than the reported value of the self-diffusion coefficient of water molecules, which is noted as $2.30\times10^{-3}$ mm$^2$/s at 25° C. The higher values of diffusivity estimated may be due to additional translational motion of water molecules associated with the table vibration during the application of diffusion-weighting gradient.

The $T'_1$-curve in neural tissues (WM and GM) is complex and deviates from the mono-exponential decays. The $T'_1$-curve was fitted with a bi-exponential function as previously described (Soellinger M, Langkammer C, Seifert-Held T, Fazekas F, Ropele S. Fast bound pool fraction mapping using stimulated echoes. Magn. Reson. Med. 2011; 66:717-24; and Ropele S, Seifert T, Enzinger C, Fazekas F. Method for quantitative imaging of the macromolecular 1H fraction in tissues. Magn. Reson. Med. 2003; 49:864-71). The diffusion of the water molecules in biological tissue is also intricate and difficult to interpret. However, the Monte Carlo simulation of water diffusion in WM and ultra-high-b study of the ex-vivo CSC demonstrated almost constant signal from the axonal and approximately mono-exponentially decaying signal from the outside of axonal spaces when the diffusion gradient was applied perpendicular to the CSC. The signal remaining in the ultra-high-b (>5,000 s/mm$^2$) region may represent restricted water in axons, and the decay rate, if any exists, may indicate the degree of demyelination. Signal from the myelin space is considered as negligible because of the very short $T_2$ of water molecules in myelin space compare with $T_E$. Therefore, the diffusion-decay curve was fitted with the exponential plus constant function and a constant component was assigned to axonal space as previously described (Sapkota N, Rose J, Miller S, Bowman B, Shah L, Bisson E, Yoon S, Jeong E K. Estimation of Intra-Axonal Fraction in Spinal Cord White Matter by using Monte Carlo Simulation of Water Diffusion and High b-value Diffusion Sensitized MRI. In: Proc. Intl. Soc. Mag. Reson. Med. Vol. 23. Toronto; 2015. p. 3044). In this study, the mean value of the restricted water fraction at the C3 vertebra level was estimated as 0.36±0.05 in the lateral WM columns (ROIs shown in FIG. 5), which agreed well with the previously reported average value of 0.34±0.08 (10) from anterior, posterior, and lateral WM columns using 10 in-vivo studies of the human CSC at the C4-05 vertebra level ($T_M$=500 ms, $b_{max}$=7,350 s/mm$^2$).

Unlike conventional DWSTE, the 2D ss-DWSTEPI-rFOV sequence does not waste the long $T_M$ (>250 ms) to acquire images from a single slice, but rather acquires images from all slices of a specific slice group within the $T_M$. Therefore, the time efficiency using the new sequence was greatly improved, which results in improving the signal-to-noise ratio of the measurement for a fixed acquisition time. Furthermore, implementation of the reduced FOV scheme described in this work is more beneficial in the new sequence as the first 90° RF pulse flips the magnetization from total slice FOV and the second 90° RF pulse with $G_{SS}$ in the phase-encoding direction prepared magnetization from total slice and phase FOV. The magnetization of the slice and phase FOV is prepared once while imaging a group of slices. In conventional DWSTE, the three slice-selective 90° RF pulses are applied on each slice while imaging the slice. The second 90° RF pulse is applied with the $G_{SS}$ in the phase-encoding direction for the reduced-phase FOV imaging, which flips the magnetization to the transverse plane in and out of the imaging slice. The repeated application of the second 90° RF pulse for the imaging of each slice continuously decreases the initial longitudinal magnetization.

In this study, variation in b-values is achieved by varying the mixing time and hence diffusion time. The 2D ss-DWSTEPI-rFOV sequence is beneficial only if the DW images with multiple b-values are needed. In 2D ss-DW-STEPI-rFOV images, the signal decays because of the combined effect of the $T'_1$ decay as well as diffusion decay. To remove the effect of the $T'_1$ decay from the experimentally measured $T'_1$-diffusion-decay curve, a set of $b_0$ images for all $T_M$s should be acquired, which adds an extra effort in data acquisition and post-processing. However, the $b_0$ images may also be used to calculate bound-pool water fraction to evaluate the myelination in WM. Some applications such as q-space imaging require the variation in b-value by increasing diffusion gradient strength rather than the diffusion time as demonstrated here. The variation in b-value achieved by increasing gradient strength is also possible in the 2D ss-DWSTEPI-rFOV imaging; however, different slices would have different $T_M$s and hence different sets of b-values. The slices should not be permuted between measurements to keep the mixing time (diffusion time) constant.

At present, a limited number of clinical whole-body MRI systems are equipped with increased gradient strength, such as 80 mT/m. High-b DWI (b=~4,000 s/mm$^2$) can be measured with moderate $T_2$ signal loss using DWSE; however, DWSTE can still offer a benefit by acquiring even higher b-values for rDWI to assure complete suppression of the signal from the hindered water such as extra-axonal water. The benefit of DWSTE for UHB-rDWI using this increased gradient strength needs to be analyzed.

E. Conclusions

A 2D ss-DWSTEPI-rFOV sequence for the ultra-high-b DW imaging with reduced FOV scheme was successfully designed and demonstrated in the phantom as well as in CSC in-vivo imaging. The new sequence can be used to acquire high-resolution ultra-high-b DW images with higher signal-to-noise ratio from localized anatomic structures such as the SC and the optic nerve with significantly reduced distortion induced by nonlinear static field inhomogeneity when compared with the conventional 2D ss-DWSTEPI.

Example 2: Characterization of Spinal Cord White Matter by Suppressing Signal from Hindered Space: A Monte Carlo Simulation and an Ex Vivo Ultrahigh-b Diffusion-Weighted Imaging Study Signal measured from white matter in diffusion-weighted imaging is difficult to interpret because of the heterogeneous structure of white matter. Characterization of the white matter will be straightforward if the signal contributed from the hindered space is suppressed and restricted signal is analyzed. In this study, a Monte Carlo simulation (MCS) of water diffusion in white matter was performed to understand the behavior of the diffusion-weighted signal in the white matter. The signal originating from the hindered space of an excised pig cervical spinal cord white matter was suppressed using the ultrahigh-b radial diffusion-weighted imaging. A light microscopy image of a section of white matter was obtained from the excised pig cervical spinal cord for the MCS. The radial diffusion-weighted signals originating from each of the intra-axonal, extra-axonal, and total spaces were studied using the MCS. The MCS predicted that the radial diffusion-weighted signal remains constant in the intra-axonal space and decreases gradually to about 2% of its initial value in the extra-axonal space when the b-value is increased to 30,000 s/mm². The MCS also revealed that the diffusion-weighted signal for a b-value greater than 20,000 s/mm² is mostly from the intra-axonal space. The decaying behavior of the signal-b curve obtained from ultrahigh-b diffusion-weighted imaging ($b_{max}$~30,000 s/mm²) of the excised pig cord was very similar to decaying behavior of the total signal-b curve synthesized in the MCS. A mono-exponential plus constant fitting of the signal-b curve obtained from a white matter pixel estimated the values of constant fraction and apparent diffusion coefficient of decaying fraction as 0.32±0.05 and (0.16±0.01)×10⁻³ mm²/s, respectively, which agreed well with the results of the MCS. The signal measured in the ultrahigh-b region (b>20,000 s/mm²) is mostly from the restricted (intra-axonal) space. Integrity and intactness of the axons in white matter can be evaluated by assessing the signal in the ultrahigh-b region.

A. Introduction

An advanced magnetic resonance imaging (MRI) technique, high-b diffusion-weighted imaging (DWI), has been evolving for neural tissues imaging because it provides enhanced contrast between white matter (WM) and gray matter (GM) and higher sensitivity in gliomas grading. High-b DWI may also be beneficial in detecting additional subtle WM lesions. Restricted compartment in WM can be estimated using ultrahigh-b radial DWI (UHB-rDWI, the DWI with the applied field gradient perpendicular to the fibers), which can be a biomarker for the characterization of the WM. An understanding of the relationship between the behavior of diffusion-weighted (DW) signal with respect to b-value and fiber microstructure may elucidate the physiologic processes underlying both the loss and recovery of neural function in disease states and with therapy.

Recently, various DWI methods such as q-space imaging, AxCaliber, and NODDI have been proposed to characterize the neural tissues. However, q-space and Axcaliber methods require strong gradient strength, which cannot be directly implemented in current human MRI systems. Furthermore, the AxCaliber and NODDI models assume no exchange between intra- and extra-axonal compartments, which may not be valid in the case of demyelination disease. Fitting of the signal vs. b (signal-b) curve obtained from UHB-rDWI is the conventional DWI method that has been considered as a potential technique to characterize neural tissues; however, because of the complex structure of the WM, its characterization is not straightforward.

In DWI of the WM, signals from the intra-axonal (IA) and extra-axonal (EA) spaces dominate the total DW signal in WM. The contribution of myelin water to the DW signal is negligible because the water molecules in myelin have short T2 (~10 ms) for a relatively long echo-time (TE~100 ms). The diffusion motion perpendicular to the fibers is restricted in the IA space and hindered in the EA space. Because axons are almost cylindrical in structure, the restricted diffusion inside the axons may be modeled with the diffusion inside an impermeable cylinder. The analytical expressions for the DW signal attenuation in an impermeable cylinder have previously been reported; however, because of the complicated structure of the WM, including a restricted space formed by the heterogeneous distribution of axons and a hindered space with indefinite hindrance provided by the axons and other micro-organelles, an analytical solution of a diffusion equation in WM is not possible.

In DWI, the signal attenuation can be expressed using the cumulant expansion, which is a Taylor expansion of the logarithm of the signal in power of b in the vicinity of b=0:

$$\ln(S_b/S_0) = -b \cdot ADC + \frac{1}{6} K_{app}(b \cdot ADC)^2 + \ldots \quad [4]$$

where $S_b$ and $S_0$ are the signal intensities with and without diffusion-weighting, respectively. ADC is the apparent diffusion coefficient and $K_{app}$ is the apparent excess diffusional kurtosis. The parameter b is defined by the expression $b=(\gamma \delta G_D)^2 \times (\Delta - \delta/3)$, where $\gamma$ is the gyromagnetic ratio, and $\delta$, $\Delta$, and $G_D$ are, respectively, the duration, separation of leading edge, and amplitude of the DW gradient. For free diffusion, the distribution of the molecular displacement is Gaussian. Therefore, the second and other higher terms of the Eq. [4] become zero. The signal decays mono-exponentially with the b-value as described in the Stejskal-Tanner equation (E. O. Stejskal, J. E. Tanner, Spin Diffusion Measurements: Spin Echoes in the Presence of a Time-Dependent Field Gradient, J. Chem. Phys. 42 (1965) 288. doi: 10.1063/1.1695690). For the restricted diffusion, such as the diffusion in WM, the signal decays non-monoexponetially with the b-value. A bi-exponential signal decay has been reported in rat brain ex vivo, rat brain in vivo, and human brain in vivo. A mono-exponential with a constant baseline model has been used to fit the signal-b curve in human brain in vivo and spinal cord in vivo. A tri-exponential model has been used as a better fitting model than bi-exponential in rat brain in vitro and bovine optic nerve ex vivo. A multi-exponential decay has been reported in rat brain in vivo and rat brain and bovine optic nerve in vitro. To characterize a signal behavior in the restricted diffusion, the higher order terms of the cumulant expansion (Eq. [4]) should be considered; however, the cumulant expansion has a finite radius of convergence at b=0, therefore, it is useful only at intermediate and low b-values.

As described herein, Monte-Carlo simulation (MCS) was performed for the intensive study of the water diffusion in WM. The MCS provides the detailed behavior of the signal-b curve in the IA and EA spaces separately. Previous MCS studies of water diffusion in WM with different WM models did not clearly explain the behavior of the signal-b curve in the ultrahigh-b (UHB) region and the potential application of the UHB-rDWI to characterize the WM. The focus of this study was to evaluate the DW signal originating from each of the IA, EA, and total spaces of WM using the MCS and to suppress the DW signal originating from the hindered space of the excised pig cervical spinal cord (CSC) WM using the diffusion parameters (diffusion duration, gradient amplitude, and diffusion time) guided by the MCS.

B. Methods

Light Microscopy Image of a Section of Pig Cervical Spinal Cord White Matter.

Figures 6A, 6B, 6C:
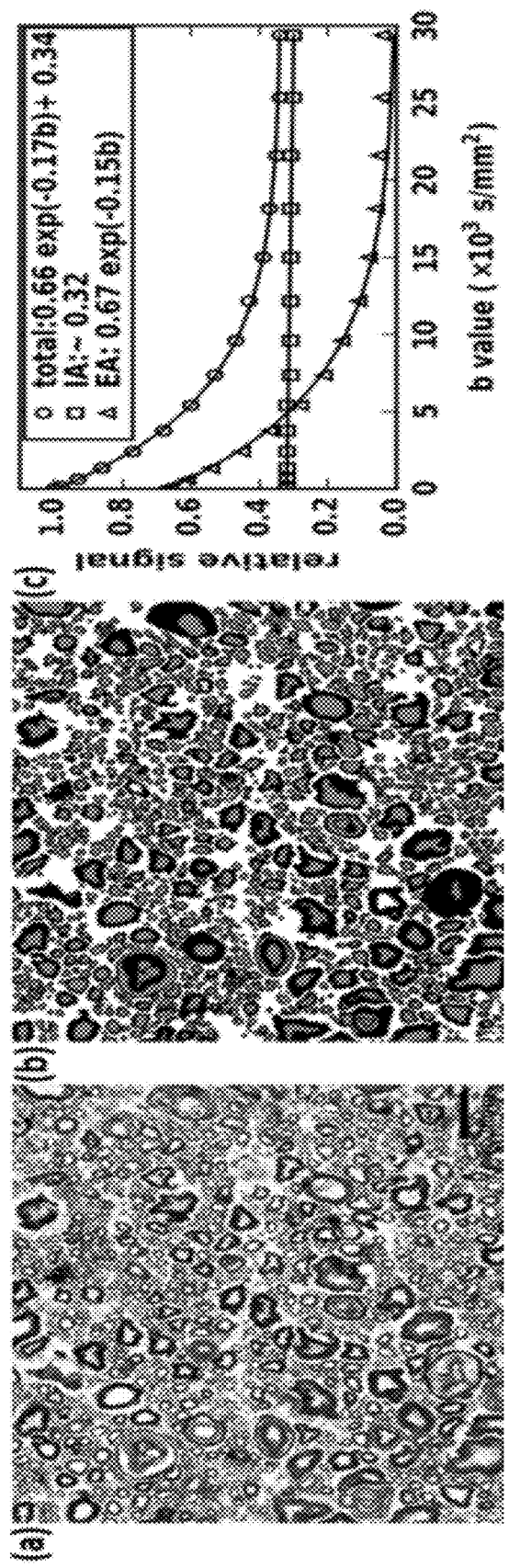
FIGS. 6A-C show the results of the Monte-Carlo simulation (MCS). MCS: (A) LMI (2D cross-section view) of a section of pig CSC-WM (187×140 µm$^2$), (B) segmentation of the LMI shown in (A) into IA, EA, and myelin spaces, and (C) signal-b curves obtained from the MCS of water diffusion in the WM section (B). Scale bar in (A) is equal to 20 µm. In (B), the gray is IA space, white is EA space, and black is myelin space. In (C), solid lines are the MCF of the total signal and mono-exponential fitting of the IA and EA signals. S4 set (δ=30 ms, Δ=450 ms, and G$_D$=0-40 mT/m) was chosen for the simulation.

The excised healthy pig cord (C2-C6) was fixed for 2 days in buffered formalin and then stored at 4° C. in phosphate-buffered saline (PBS) for 8 months. Sections of the pig cord (C2-C3) that had been fixed for 2 days in buffered formalin were post-fixed in osmium tetroxide, dehydrated in ascending concentrations of ethanol, and embedded in epoxy resin. Cross-sections of the cord were cut to 1 μm in thickness, mounted on glass slides, and stained with toluidine blue prior to observation by light microscopy. A light microscopy image (LMI) of a section of cervical spinal cord WM (CSC-WM) obtained with a light microscope (magnification×60) is shown in FIG. 6A. The image was digitally segmented into three spaces: intra-axonal, extra-axonal, and myelin as shown in FIG. 6B, using the ImageJ program available in the NIH public domain.

MCS of Water Diffusion in Cervical Spinal Cord White Matter.

Figures 9A, 9B:
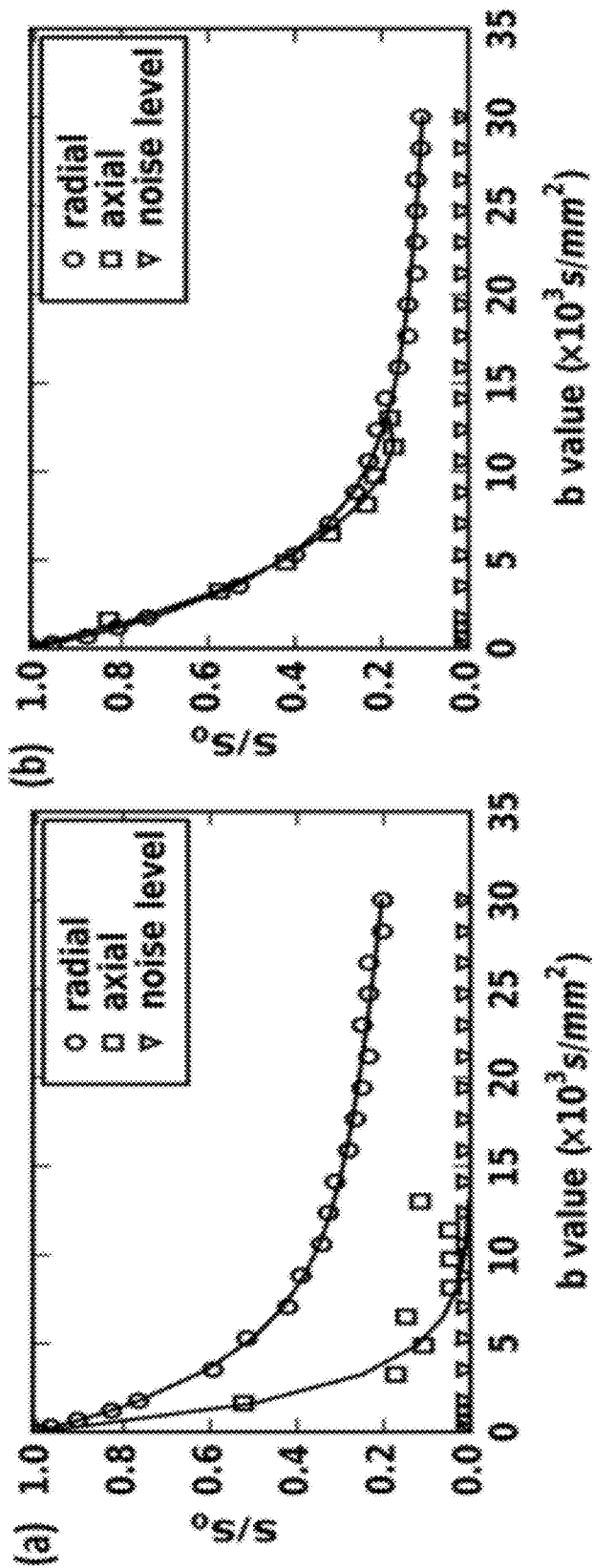
FIGS. 9A-B shows the experimental signal-b curves for axial and radial DWI in WM (A) and GM (B). The axial DW signal in WM quickly decays to noise level, indicating almost no barrier, but in the GM, slow-decaying axial signal indicates the existence of some restrictions even along the axial direction.

The MCS of water diffusion proceeds with uniform distribution of N water molecules into the IA and EA spaces of the LMI obtained from the excised pig CSC-WM (FIG. 6B). No water molecules are assigned into the myelin space because the short $T_2$ (~10 ms) water protons in myelin space do not contribute to the total signal in the DWI with long TE~100 ms. A three-dimensional diffusive motion is incorporated by updating the position of each molecule in every $\delta t$ during a diffusion time $T_{diff}$. The new position is calculated by adding a constant length, $(6D\delta t)^{1/2}$, and a random direction step vector to the current position. D is an intrinsic diffusion coefficient of a water molecule, and a random uniform direction is given by the spherical polar coordinates $\phi=2\pi u$ and $\theta=\cos^{-1}(2v-1)$, where u and v are uniformly distributed random number in the range [0, 1]. The value of D is chosen based on the value of axial diffusivity, i.e., the diffusivity calculated with the DW gradient parallel to the fibers, measured as $0.50\times10^{-3}$ mm$^2$/s in our specimen (see, FIG. 9A). Previously reported values of axial diffusivity, such as $0.47\times10^{-3}$ mm$^2$/s from the five excised CSC of normal control subjects (E. C. Klawiter, R. E. Schmidt, K. Trinkaus, H.-F. Liang, M. D. Budde, R. T. Naismith, et al., Radial diffusivity predicts demyelination in ex vivo multiple sclerosis spinal cords, Neuroimage. 55 (2011) 1454-60. doi:10.1016/j.neuroimage.2011.01.007) and $0.62\times10^{-3}$ mm$^2$/s from the three sections of a post-fixed excised pig CSC (T. H. Kim, L. Zollinger, X. F. Shi, J. Rose, E.-K. Jeong, Diffusion tensor imaging of ex vivo cervical spinal cord specimens: the immediate and long-term effects of fixation on diffusivity, Anat. Rec. (Hoboken). 292 (2009) 234-41. doi:10.1002/ar.20823), also support the value of D chosen in the present study. Because the axial DW signal decays mono-exponentially with b-value in our specimen (see, FIG. 9A), it does not violate common sense to choose the same value of D for both the IA and EA spaces as in (M. Nilsson, J. Latt, E. Nordh, R. Wirestam, F. Stahlberg, S. Brockstedt, On the effects of a varied diffusion time in vivo: is the diffusion in white matter restricted?, Magn. Reson. Imaging. 27 (2009) 176-87. doi:10.1016/j.mri.2008.06.003). The details of the simulation parameters for the different sets of the simulations (S1, S2, S3, S4, and S5) are given in Table 1.

TABLE 1

The MCS parameters (units: $D_{IA}$, $D_{EA}$ = mm$^2$/s; $\delta t$-$\mu s$; $\delta$, $\Delta$, $T_{diff}$-ms; $b_{max}$-s/mm$^2$).

| | |
|---|---|
| $D_{IA} = 0.5 \times 10^{-3}$, $D_{EC} = 0.5 \times 10^{-3}$ | - Diffusivities in IA and EA spaces |
| $\delta t = 0.1$, $T_{diff} = 600$ | - Update time and diffusion motion time |
| N = 18,000 (IA-32%, EA-68%) | - Total molecules distributed into IA and EA spaces |
| S1: $\delta = 25$, $\Delta = 100$, $b_{max} = 7,232$ | |
| S2: $\delta = 45$, $\Delta = 75$, $b_{max} = 10,650$ | |
| S3: $\delta = 50$, $\Delta = 100$, $b_{max} = 18,261$ | |
| S4: $\delta = 30$, $\Delta = 450$, $b_{max} = 29,380$ | |
| S5: $\delta = 45$, $\Delta = 225$, $b_{max} = 31,550$ | |

In this simulation, axons are considered as non-permeable unless otherwise stated. When a molecule crosses a local barrier (IA or EA space to myelin space), the last position is abandoned and a new position is generated in a random direction until it finds a position belonging to the same space. A molecule is either transmitted or reflected at the boundary with a probability that is determined by the permeability, P, when the axons are considered as permeable. The P=5 $\mu$m/s is chosen (FIG. 7B) based on the previously reported value of permeability 2.7 $\mu$m/s in *Xenopus oocytes* (J. V Sehy, A. A. Banks, J. J. H. Ackerman, J. J. Neil, Importance of intracellular water apparent diffusion to the measurement of membrane permeability, Biophys. J. 83 (2002) 2856-63. doi:10.1016/S0006-3495(02)75294-6) and 7.0-9.0 $\mu$m/s in bovine optic nerve (G. J. Stanisz, A. Szafer, G. A. Wright, R. M. Henkelman, An analytical model of restricted diffusion in bovine optic nerve, Magn. Reson. Med. 37 (1997) 103-11. http://www.ncbi.nlm.nih.gov/pubmed/8978638). The successful positions of all molecules are recorded in every 100 $\mu$s. The DW signal is then obtained by computing phase accumulated by each molecule during the position-recording steps and summing the contributions from all water molecules as $S=\Sigma_k \exp(-i\gamma\Sigma_j r_{jk} \cdot G_D{}^j)$, where $r_{jk}$ is the position vector of $k^{th}$ molecule in $j^{th}$ time step, $G_D{}^j$ is the applied gradient in $j^{th}$ time step. Variation in the b-value is achieved by varying the gradient amplitude. The signals for IA, EA, and total (IA plus EA) spaces are calculated using the molecules distributed only in the IA, EA, and total spaces, respectively. The signal-b curve obtained with the DW gradient applied perpendicular to the fibers can be much more informative than that applied parallel to the fibers for the characterization of the WM. Therefore, the MCS is performed with radial DW gradient unless otherwise stated. The $T_2$ values for the water molecules in IA and EA spaces are assumed to be the same, and the effect of $T_2$ is ignored in the signal calculation.

The MCS software was programmed using Message Passing Interface (MPI) C++ to utilize parallel processors available at the Center for High Performance Computing (CHPC) of the University of Utah. The computation time was 20-25 minutes for $T_{diff}$=600 ms with 24 processing elements.

MRI Experiment.

The axial DW images were obtained using three-dimensional multi-shot DW stimulated echo acquisition mode echo-planar imaging (ms-DW-STEAM-EPI) with echo train length 9 on a Siemens 3T MRI system (Trio, Siemens Medical Solutions, Erlangen, Germany). The system was equipped with the maximum gradient strength and gradient slew rate as 40 mT/m and 200 mT/m/s, respectively. A homebuilt birdcage coil (1.27 cm inner diameter, 2.54 cm in length) was used as the transmit-receive coil. The specimen was immersed into a tube filled with a thick gel of corn starch to remove the susceptibility artefact at the surface of the tissues. The details of imaging parameters for the different sets of measurements (M1, M2, and M3) are given in Table 2. The repetition times (TRs) were chosen in such a way that each measurement would have similar recovery time for the longitudinal magnetization. The DW gradient was applied in the left-right direction while the spinal cord was parallel to the $B_0$ (static field) direction. The post-processing of the DICOM images was performed using processing software written in Python. A variation in the b-value in DWI was obtained by varying the gradient amplitude.

TABLE 2

The MRI parameters (units: $\delta$, $\Delta$, TE, TR, TM-ms and $b_{max}$-s/mm$^2$).

| | |
|---|---|
| FOV = 96 × 24 mm$^2$ | In-planner resolution = 0.75 × 0.75 mm$^2$ |
| Acquisition matrix = 128 × 32 × 16 | Slice thickness = 2 mm |
| Bandwidth = 500 Hz/pxl | Scan time = 30-60 minutes for 2 averages |
| M1: $\delta$ = 30, TE = 90, TR = 1050, TM = 450, $b_{max}$ = 30,082 | |
| M2: $\delta$ = 30, TE = 120, TR = 1050, TM = 450, $b_{max}$ = 30,017 | |
| M3: $\delta$ = 45, TE = 120, TR = 825, TM = 225, $b_{max}$ = 28,226 | |

Curve Fitting.

The total signal-b curve was fitted to a mono-exponential plus constant fitting (MCF) model $S_b/S_0 = f_{decay} \exp(-b \cdot ADC) + f_{const}$ using non-linear curve-fitting sub-routine included in SciPy (Python), where $S_b$ and $S_0$ are signals at a given b-value and $b_0$ (b=0 s/mm$^2$), respectively. $f_{decay}$ and $f_{const}$ are the fractions of decaying and constant signals, respectively, and ADC is the apparent diffusion coefficient of the decaying signal.

C. Results

Monte-Carlo Simulation.

The MCS of water diffusion with LMI (FIG. 6B) obtained from a section of CSC-WM as an input geometry predicted that the signal-b curve remains almost constant (decay rate 0.22×10$^{-5}$ mm$^2$/s) for the IA space; however, the signal-b curve for the EA space decays approximately mono-exponentially (decay rate 0.15×10$^{-3}$ mm$^2$/s) to about 2% of its initial value when the b-value is increased to 30,000 s/mm$^2$ as shown in FIG. 6C, under the condition that the maximum gradient strength is in the range of gradient strength available in most clinical scanners (<40 mT/m). The total WM signal synthesized in the simulation decreases in the low-b region and remains constant in the UHB region as the total signal is the sum of decaying signal from EA space and constant signal from IA space. Therefore, the total signal-b curve in the MCS can be fitted with the mono-exponential plus constant function. A MCF of the total signal-b curve estimated the values of $f_{const}$ and ADC as 0.34±0.03 and (0.17±0.03)×10$^{-3}$ mm$^2$/s, respectively.

Figures 7A, 7B, 7C:
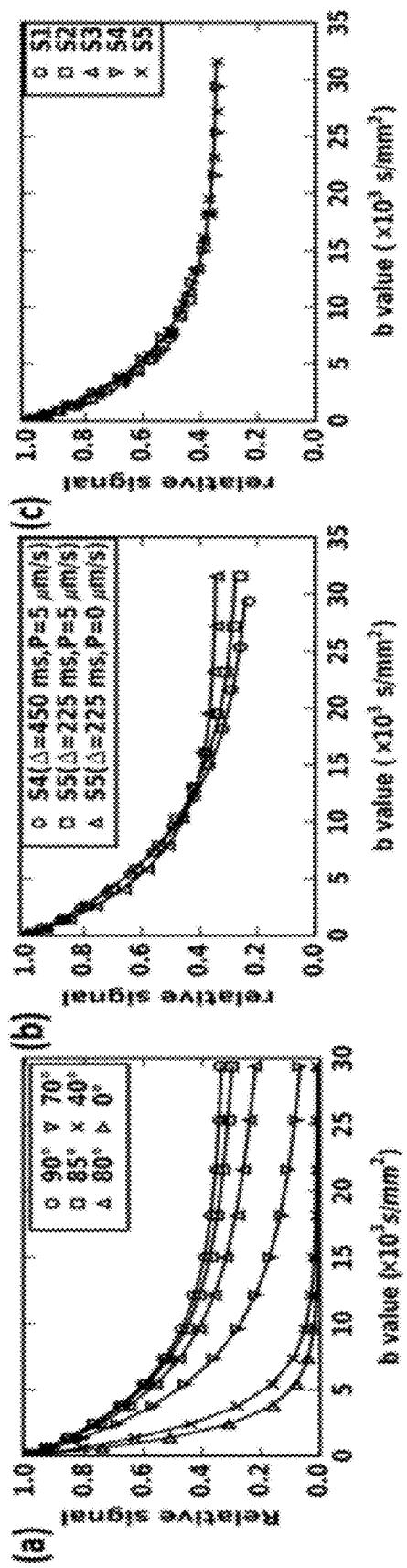
FIGS. 7A-C shows the signal-b curve. MCS: Signal-b curves for (A) the various angles between DW gradient and fiber directions, (B) the different diffusion times with the exchange of molecules between IA and EA spaces, and (C) the different sets of diffusion parameters given in Table 1. The solid lines are the MCF of the total signal-b curve.

Based on the MCS, the behavior of the signal-b curve is affected by the various factors such as the deviation of the direction of DW gradient from the actual radial direction of fibers and exchange of the water molecules (permeability) between IA and EA spaces. It can be seen from FIG. 7 that the total signal no longer remains constant in the UHB region when the DW gradient is not perfectly perpendicular to the fibers (FIG. 7A) or the exchange occurs between the molecules in the IA and EA spaces (FIG. 7B). On the other hand, the signal-b curve does not depend on the imaging parameters chosen (FIG. 7C).

Ex Vivo UHB-rDWI Experiments.

The presence of noise in the measurements degrades the accuracy of fitting parameters obtained from the MCF of the signal-b curve. In this study, the signal-to-noise ratio (SNR)>100 was measured in $b_0$ images. The signal-b curve for each WM pixel was fitted with the MCF function, and $f_{const}$ and ADC maps were obtained from a 2-mm-thick slice at the level of the C3-C4 vertebrae. The DW images ($b_0$ and $b_{max}$) and MCF parameter maps ($f_{const}$ and ADC) obtained in UHB-rDWI are shown in FIG. 8A. Typical signal-b curves obtained from a pixel of WM for three sets measurements are shown in FIG. 8B. The MCF of the signal-b curves obtained from the WM pixel (FIG. 8B) estimated the values of the $f_{const}$ as 0.32±0.05, 0.29±0.05, and 0.32±0.06 and the values of ADC as (0.16±0.01)×10$^{-3}$ mm$^2$/s, (0.16±0.01)× 10$^{-3}$ mm$^2$/s, and (0.17±0.01)×10$^{-3}$ mm$^2$/s for the M1, M2, and M3 measurements, respectively.

C. Discussion

The MCS predicted that the radial DW signal decays mono-exponentially at a rate of 0.22×10$^{-5}$ mm$^2$/s in the IA space, which is negligible compared to the decay rate 0.15×10$^{-3}$ mm$^2$/s of the signal in the EA space. Therefore, the signal from the IA space has been considered as almost constant with respect to b-value. In a region with the b-value greater than 20,000 s/mm$^2$ (the UHB region), the total signal is mainly from the IA space and is almost constant. The maximum radial displacement of molecules in the IA space is limited by the diameters of the axons, no matter how long the diffusion time is allowed. As a result, the applied radial DW gradient (strength<40 mT/m) does not create enough phased dispersion between spins confined inside a smaller axon (diameter<4 μm), which is required for the signal loss in DWI. For the limit of a long time ($\delta D \gg R$), and $G_D$=40 mT/m, $\delta$=30 ms, and D=0.5×10$^{-3}$ mm$^2$/s, an approximately 2% radial DW signal loss has been calculated for an impermeable cylinder of diameter (2R=4 μm) using the Neuman's formula (C. H. Neuman, Spin echo of spins diffusing in a bounded medium, J. Chem. Phys. 60 (1974) 4508. doi:10.1063/1.1680931): $\ln(S/S_0) \cong 7(\gamma G_D)^2 R^4 \times 2\delta/96D$. Approximately 7% signal loss in the IA space is mostly from the bigger axons presented in the LMI (FIG. 6B). Note that the diameter of the axon along the DW field gradient direction (left-right) represents the size of the restriction.

The signal from the IA space may decay with b-value when a very high DW gradient strength (~1000 mT/m) is used. This is because even a small molecular displacement will be sufficient to create enough phase dispersion in the presence of very high DW gradient strength. Use of the very high DW gradient strength (1000-1400 mT/m) can be found in a bovine optic nerve experiment and in a simulation of water diffusion inside a cylinder. Therefore, higher b-value with lower gradient strength and shorter $\delta$ (longer $\Delta$) is preferred to get constant signal from IA space. The MCF of the signal-b curve obtained in the MCS estimated the values of $f_{const}$ and ADC as 0.33±0.03 and (0.17±0.03)× 10$^{-3}$ mm$^2$/s, respectively. The estimated constant fraction agreed well with the fraction of IA space (0.32) measured in the LMI (FIG. 6B) when the myelin space is neglected.

In UHB-rDWI measurements, a MCF of the signal-b curve obtained from a WM pixel estimated the values of $f_{const}$ and ADC of decaying fraction as 0.32±0.05 and (0.16±0.01)×10$^{-3}$ mm$^2$/s, respectively, for the set M1, which agreed well with the results of the MCS. Almost similar decaying patterns of the signal-b curves were observed in all three measurements (M1, M2, and M3, FIG. 8B), which agreed well with the findings of the MCS (FIG. 7C).

The physical environment within a biological sample is heterogeneous, and a two-compartment model is too simplified; however, it does not violate common sense if the WM space is divided into two compartments for the radial diffusion: (i) 'restricted space' mainly composed of the IA space and (ii) 'hindered space' composed of EA space, astrocytes, oligodendrocytes, and immune cells in pathologic cord. The validity of this model is that axon is surrounded by several tens of lipid bilayers (myelin), of which one side of this bilayer is hydrophobic. The lipid bilayers completely block the exchange of water molecules between the IA space and myelin/EA space. The majority of the hindered space is covered by EA space, and the diffusion in the hindered spaces is assumed to be same as in the EA space. If there were a restricted space other than IA space, for instance, a restricted space formed by astrocytes and oligodendrocytes, the signal measured in the UHB region should have similar values for both the radial and axial DWI as the restricted space formed by the astrocytes and oligodendrocytes provides equal restriction in both radial and axial diffusive motion. No isotropic diffusion was observed in WM in the UHB region as shown in FIG. 9, whereas isotropic diffusion was observed in GM even in the low-b region. Therefore, the signal measured in the UHB region may be solely due to the water molecules presented in IA space in the healthy WM.

Since the hindered space, which is composed of EA space, astrocytes and oligodendrocytes, is too complicated to be modeled by a simple geometry, the signal is interpreted after suppressing the signal from the hindered space by applying a sufficiently high diffusion-weighting. After the suppression of the signal from the hindered space, the remaining signal is from the restricted space (IA space). The integrity and intactness of the axons may be characterized by assessing the signal purely from the IA space. The fraction of the restricted signal ($f_{const}$) may represent the intra-axonal fraction (IAF); however, the value of $f_{const}$ may be deviated from the actual IAF if different values of $T_2$ exist in two different spaces: restricted and hindered spaces.

The signal behavior in UHB may be affected by the application of imperfect radial DW gradient with respect to fibers, the existence of the orientational (angular) fiber dispersion within a voxel, and the existence of exchange of water molecules between IA, EA, and myelin spaces. The effect of an imperfect radial DW gradient may be corrected by measuring the angle between fibers and the applied gradient field using conventional diffusion tensor imaging (DTI). To our knowledge, the value of angular fiber dispersion in the CSC-WM has not been reported in literature; however, the value of orientation dispersion index (ODI) has been reported as 0.03 using NODDI model, which is much smaller than the value of the ODI 0.14 reported for a corpus callosum-body. The angular fiber dispersion in the corpus callosum-body has been report as 18.1°. Since the ODI of CSC-WM is nealy one fifth of the ODI of corpus callosum-body, the angular fiber dispersion of the CSC-WM may be estimated as 3-4°, one-fifth of the angular dispersion of the corpus callosum. The effect of such a smaller angular dispersion may not be significant in the UHB region. The exchange effect may also be evaluated by assessing the remaining signal in the UHB region for different diffusion times (~TMs). These previous studies applied the "diffusion filter" to attenuate the signal from the fast-diffusing compartment (EA space), which is not required in the present study as the signal from the EA space is almost suppressed in the UHB region.

In the present study, the angle between fibers and applied DW gradient was measured using conventional DTI. The DW gradient was found to be perpendicular to the fibers within the range of 5°, which does not significantly change the value of restricted fraction and decaying pattern of the signal-b curve in the UHB region. If there were an exchange of water molecules between IA and EA spaces, the lower value of $f_{const}$ would be anticipated in M2 (TM=450 ms) compared with M3 (TM=225 ms), as predicted by the MCS. The UHB-rDWI estimated 9% smaller value of $f_{const}$ in M2 than in M3. The minor effect of exchange may be observed because of the exchange of molecules via the nodes of Ranvier. The fitting parameters of the signal-b curves were not significantly different for different values of TM (TM=27-219 ms and $b_{max}$=28,000 s/mm$^2$) in the DWI study of human brain in vivo, the finding also supports the fact that the exchange of molecules between IA and EA spaces in WM is not significantly high.

In vivo application of this technique is feasible but not as easy as ex vivo application because the DW images suffer from low SNR due to the deeper location of the CSC from the skin and short scan time. The diffusion coefficient is generally three times faster in the in vivo tissues than in the ex vivo, which greatly reduced the high b-value to 10,000 s/mm$^2$ needed to suppress the signal from hindered space. In vivo human spinal cord imaging with the maximum b-value of 14,000 s/mm$^2$ and 7,300 s/mm$^2$ have already been reported, which demonstrates the possibility of the in vivo application of this technique.

E. Conclusions

Based on the MCS, the radial DW signal from the hindered space can be suppressed when b-value is sufficiently high (~20,000 s/mm$^2$ in our specimen) and the radial DW signal from the IA space does not decay with increase in b-value as long as the water molecules do not exchange between IA, myelin, and EA spaces. Axial and radial DWI of the ex vivo spinal cord excluded the possibility of the restricted space in WM other than IA space. The signal measured in the UHB region is mostly from the restricted space, i.e., IA space. Integrity and intactness of the axons in WM can be evaluated by assessing the signal in the UHB region. The fraction of restricted water and the decay rate of the signal-b curve in the UHB region are the two essential biomarkers for the characterization of the WM. Both biomarkers can be affected by the application of a non-perfect radial diffusion gradient and the existence of the exchange of molecules between the IA and EA spaces.

Example 3: Ultra-High-b Diffusion MRI (UHb-DWI) of Cervical Spinal Cord in Patient with Multiple Sclerosis As described in further detail below, this study sought to improve imaging of the cervical spinal cord (CSC) with quantitation of spinal cord injury using novel diffusion MRI ultrahigh-b radial diffusion weighted imaging (UHb-rDWI) techniques in control subjects and in Multiple Sclerosis (MS) patients with new CSC lesions. Serial imaging was used to demonstrate quantitation of combined demyelination and axonal injury in evolving MS lesions. UHb-rDWI experiments were performed twice on one healthy control and three times on two relapsing-remitting MS patients in an interval of 7 months on a Siemens 3T MRI system (Trio, Siemens Medical Solutions, Erlangen, Germany). Using T2-weighted imaging (T2WI) for planning, axial high-b diffusion images were acquired using 2D Single Shot Diffusion-Weighted Stimulated EPI with Reduced FOV (2D ss-DWSTEPI-rFOV) sequence and a dedicated 8 channel array coil. The imaging parameters were TR/TE=3 s/64 ms, FOV read/phase=128/44 mm, 6 min 19 sec scan time, 6 averages, 21 slices, 1×1×4 mm voxel dimension, and linearly spaced 7 b-values (12 ms gradient duration δ and 38 mT/m amplitude $G_D$) ranging from about 573 s/mm to about 7348 s/mm along the left-right direction corresponding to the 7 mixing times, TMs (time interval between two 90° RF pulses) ranging from about 9 ms to about 465 ms. An additional b image without diffusion gradient was obtained for each TM for correcting T1 decay during TM. UHb-rDWI findings in the white matter (WM) in the normal human CSC were consistent in two separate studies. In one MS patient, the right lateral corticospinal tract affected by the active lesion revealed a marked decrease in signal intensities over the range of b values up to 6,500 s/mm. The signal intensities in the contralateral unaffected corticospinal tract were similar to those in the normal control. The UHb-rDWI values increased on serial observations, approaching increased myelination curves, concordant with improvement in the patient's clinical status. In the second MS patient, a new lesion involved bilateral posterior columns with UHb-rDWI characteristics suggesting demyelination. The UHB-rDWI values in this MS patient also increased towards normal on serial observations, corresponding to the patient's return to clinical baseline. UHB-rDWI of the normal control was consistent in bilateral corticospinal tracts on two successive scans, demonstrating the reproducibility of this technique. The abnormality of the quantitative diffusion values in the MS patients relative to the normal subjects reflects demyelination. Comparison of the UHb-rDWI signal-b plots of lesions in the MS patients at three time points illustrates this technique's ability to detect the evolution of demyelinating lesions with axonal sparing and remyelination.

A. Introduction

Spinal cord injury in multiple sclerosis (MS) is due to varying degrees of demyelination and/or axonal damage and can cause disability in patients. Magnetic resonance imaging (MRI) provides contrast and spatial resolution of the spinal cord and, therefore, can be used in the evaluation and monitoring of MS. It is known that cord atrophy is associated with physical disability. Lesion load on conventional T2-weighted imaging (T2WI) independently correlates with physical disability and is seen more often in progressive forms of MS as compared to relapsing-remitting multiple sclerosis (RRMS). However, conventional MRI sequences (T1-weighted imaging (T1WI) and T2-weighted imaging (T2WI), short tau inversion recovery, proton density) are limited in their ability to detect the early stages of disease. Although several imaging biomarkers can be used to demonstrate demyelination in the brain (e.g., decreased magnetization transfer ratio, increased T2 and T1 relaxation times, and decreased myelin water fraction), such biomarkers are still unverified in the cervical spinal cord (CSC). Furthermore, these imaging biomarkers cannot specifically delineate demyelination or the degree of axonal loss—the latter being associated with persistent patient disability. As such, there is limited correlation of imaging findings by these MRI techniques with short- and long-term functional outcomes due to spinal cord injury in MS. The lack of strong clinical and imaging prognostic indicators contributes to poorly defined treatment pathways with outcomes that are not readily predictable. Non-invasively determining injury type, observing evolution of MS lesions, and assessing areas of active remyelination and axonal sparing can provide significant advancements in understanding the pathophysiological underpinnings of MS and early disease detection and monitoring. Disclosed herein are methods for identifying imaging biomarkers for earlier disease detection and monitoring in the follow-up and treatment stages.

Diffusion weighted imaging (DWI) can demonstrate microscopic impediments to water movement, such as membranes, which can be used to characterize tissue structure. Diffusion tensor imaging (DTI) can analyze the three-dimensional shape of water diffusion. Conventional DTI relies on the signal changes induced by the coupling between the applied diffusion gradient and the random motion of the tissue water in the background structure at specific diffusion-weighting (b-value and diffusion gradient direction). Diffusion techniques using ranges of diffusion times and strengths show that non-mono-exponential decay reflects diffusion restriction and may provide quantification of white matter structure, including axonal diameters and density. The parallel orientation of the spinal cord fibers lends itself to diffusion imaging better than the brain because of a lesser degree of multiple orientations and overlapping crossing fibers, which complicate not only data acquisition but also data interpretation. Spinal cord diffusion weighted imaging (DWI) can be post-processed to extract diffusivities such as axial ($\lambda_a$) and radial ($\lambda_r$) diffusivities and the principal axes of corresponding local symmetry system. However, conventional DTI metrics correlate poorly with axonal pathology and are not always consistent in detecting axonal dysfunction.

For Example 3, an ultrahigh-b radial DWI (UHb-rDWI) technique was used in which increasing diffusion weighting gradients from low b to UHb were applied in the direction perpendicular to the spinal cord to give greater diffusion weighted and less T2 weighted effect. The geometric distortion due to susceptibility difference between the spinal cord and vertebrae can be reduced by implementing a reduced field of view (rFOV) in the phase encoding direction and the motion induced artifact (respiratory and cardiac) using single shot acquisition. This advanced high-b DWI technique can yield better contrast between white matter and gray matter. The disclosed technique can also provide more insight into CSC pathology by analyzing the signal-b curve in the UHb (b>4,000 s/mm$^2$) region and distinguishing demyelination, inflammation, and axonal damage. The method selectively suppresses the signal contribution from the extra-axonal (EA) water in order to isolate the signal of the intra-axonal (IA) water. Monte Carlo simulation (MCS) demonstrated that in the ultrahigh-b (UHb) region, the radial DWI (rDWI) signal from EA space of the healthy CSC, where the water molecule can diffuse across many axons, decays to noise level while that from the IA space, where the motion is restricted within the axonal diameter by myelin sheath, remains constant. In the case of a demyelinated axon, which permits water to exchange between IA and EA spaces, the rDWI signal from IA space decays.

The signal behavior of the UHb-rDWI signal in different tracts of the CSC were studied, and the reproducibility of the technique in the healthy CSC and also in relapsing-remitting multiple sclerosis patients (RRMS) with new CSC lesions were validated. In addition, cross-sectional color maps of the high-b decay constant ($D_H$) were used to illustrate the extent, intensity and distribution of the lesions in the MS CSC.

B. Materials and Methods

The method was performed on human subjects. One healthy volunteer and two multiple sclerosis patients underwent UHB-rDWI experiments on a Siemens 3T MRI system (Trio, Siemens Medical Solutions, Erlangen, Germany). A specialized coil for CSC imaging was utilized for the imaging. The healthy volunteer was a 27-year-old female, who was imaged at two separate times in 60 days. Two RRMS patients were imaged at the time of an acute relapse, clinically localizing to the CSC, and then sequentially over several months.

Patient 1 was a 48-year-old male with RRMS of 14-years duration but not on immunotherapy for the past 5 years, who developed new onset of right lower extremity paresthesias and right leg weakness associated with unsteady ambulation. On the clinical T2WI, an intramedullary lesion was detected at the C3-C4 level. Serial research imaging was performed on days 11, 60, and 200 with UHB-DWI. The patient was given methylprednisolone 1000 mg IV each day for 3 days after the first research UHB-rDWI study (after day 11), and the symptoms were resolving with improved strength and ambulation at the time of the day 60 MRI exam. At day 200, the patient had returned to baseline clinical status.

Patient 2 was a 22-year-old female with RRMS of 4-years duration, who was also not on immunotherapy. She presented with an acute relapse manifested by impaired balance and sensory complaints. The initial clinical MRI of the CSC revealed a new contrast-enhancing lesion in the posterior spinal cord at the C2-C3 level. She underwent treatment with 1000 mg of methylprednisolone every day for three days. Serial research imaging was performed on days 32, 75 and 210. The patient recovered to baseline over a 4-month time period. Conventional T2WI revealed decrease in the lesion size over the course of 8 months.

Detailed MRI Methodology: The imaging was performed in two parts. First, T2WI were acquired for planning the UHb-rDWI experiment. T2WI were acquired in the axial plane (TR/TE–4 s/95 ms and acquisition resolution 0.68× 0.55×4.0 mm$^3$) and the sagittal plane (TR/TE–4 s/112 ms and acquisition resolution 0.92×0.69×3.0 mm$^3$) using a turbo spin-echo (TSE) for planning the UHb-rDWI experiment. Following this, axial (diffusion gradient perpendicular to the spinal cord) high-b diffusion images were acquired using home-developed a 2D singleshot Diffusion-Weighted Stimulated EPI with reduced FOV (2D ss-DWSTEPI-rFOV) technique and a 8 channel CSC dedicated array coil. The imaging parameters were 3 s/64 ms TR/TE, 128×44 mm$^2$ imaging FOV, 6 min 19 sec scan time, 6 averages, 21 slices with 1.0×1.0×4.0 mm$^3$ voxel dimension, and linearly spaced 7 b-values: 573, 1702, 2832, 3691, 5090, 6219, and 7348 s/m$^2$ along the left-right direction corresponding to the 7 mixing times, TMs (time interval between $2^{nd}$ and $3^{rd}$ 90° RF pulses) 9, 85, 161, 237, 313, 389, 465 ms, respectively. A constant diffusion gradient duration of value 12 ms and diffusion amplitude 38 mT/m was used for each b-value. An additional $b_o$ image without diffusion weighting gradient was obtained corresponding to each TM for correcting $T_1$ decay during TM. The b-value images undergo both T1 and diffusion decay while $b_o$-images undergo only T1 decay. The UHb-rDWI data was processed to extract the high-b decay constant, $D_H$ (b>4000 s/mm$^2$), using home-developed processing software in Python.

$T_1$ correction: The signal equation for b-value images ($S_b$) and $b_0$ images ($S_{bo}$) incorporating the diffusion and $T_1$ decay effects are:

$$S_b = (S_0^{EA} e^{-bD_L} + S_o^{IA} e^{-bD_H}) e^{-TM/T_1} \quad [5]$$

$$S_{b0} = S_o e^{-TM/T_1}, S_o = (S_o^{IA} + S_o^{EA}) \quad [6]$$

where $S_o$ is the signal measured without $T_1$ and diffusion decay, and D is an apparent diffusion coefficient. The diffusion-prepared longitudinal magnetization undergoes both diffusion and $T_1$ decay, while $b_o$ signal undergoes only $T_1$ decay. The pure diffusion signal is obtained by dividing equation [5] by equation [6].

Curve fitting: All DICOM images were post-processed using homemade processing software written in Python language (Anaconda Python, Continuum Analytics, Austin, Tex.). The signal-b curves reflect the bi-exponential decay behavior: exponential decay at the lower-b values and plateau at higher-b values. The signals from each pixel of $b_0$ image were fitted to a single-exponential function as in equation [6] and the resultant fitted curve was used to remove the $T_1$ decay, then finally fitted to either a bi-exponential or mono-exponential plus constant function depending on a signal that best fits with either of these functions. The curve was normalized to the $S_o$, the signal intensity at b=0 and minimum TM (=4 ms). The signal-b curve was first fit to a bi-exponential function like equation [5]. If $S_o^{IA}/S_o$ was less than 0.1, such as in the demyelination pixel, the signal-b curve was fit to a single-exponential function plus a constant.

C. Results

Figure 10A:
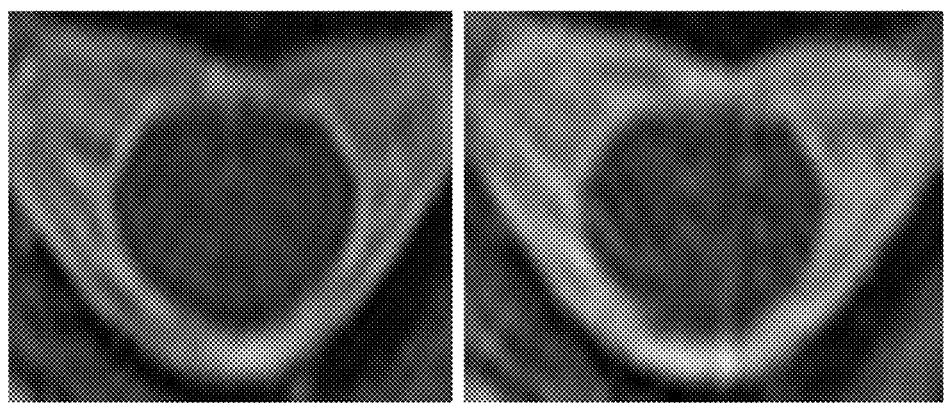
FIGS. 10A-10C show the results of two healthy CSC imaged at two separate time points 60 days apart. (A) Axial T2WI demonstrate exquisite spatial and contrast resolution due improved signal-to-noise ratio utilizing the proprietary CSC coil. (B,C) The typical signal-b curves of UHB-DWI at different fiber tracts (1—right corticospinal tract, 2—left corticospinal tract, 3—right posterior column, 4—left posterior column) in a healthy human CSC at the C3-C4 level 60 days apart. The signal intensities at the C3-C4 level are plotted for single WM pixels (red) in different white tracts with maximum bmax=7,400 s/mm2. Comparing (B) to (C) at the C3-C4 level in the different white matter tracts at the two different time points indicates the high reproducibility of the UHB-DWI technique. Note that the signal-b curves are slightly different for different WM tracts. This may reflect the different leakage effects due to differences in myelination and fractions of the gaps between two adjacent myelin sheaths.
Figures 10B, 10C:
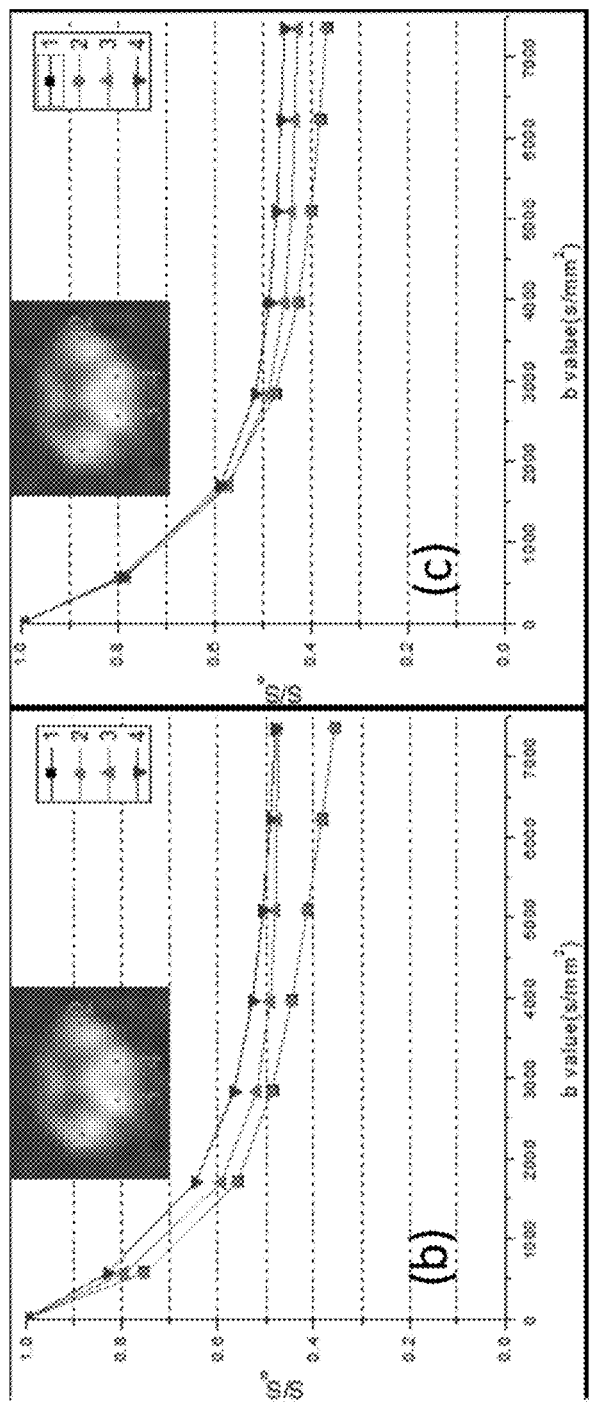

The images of the normal volunteer in FIGS. 10A-10C illustrate the typical signal-b curves of single pixel (1×1×4 mm$^3$) in UHb-rDWI data at different fiber tracts in the healthy human CSC. The UHb-rDWI results reveal that the signal measured in the UHb region (b>4,000 s/mm2) is predominantly from the restricted IA space, and the curves generated by UHb-rDWI are consistent with those predicted from investigations in the ex vivo cord and the numerical simulation using MCS. These results also demonstrate the consistency of UHb-rDWI between the contralateral tracts in the CSC, including the corticospinal tracts and the posterior columns. The signal intensity graphs showed that UHb-rDWI was consistent for the spinal cord tracts from the C1 to the C4 levels (not shown). Furthermore, the UHb-rDWI did not vary between images in the interval of 60 days.

The first MS patient (MS1) was imaged four times within 200 days after an acute attack. Day 1 was a clinical gadolinium-enhanced MRI and subsequent days 11, 60, and 200 were the research MRIs with UHb-DWI. The baseline clinical MRI of the CSC demonstrated a new enhancing, T2 hyperintense lesion in the right lateral corticospinal tract at the C3-C4 level as well as an old T2 hyperintense, non-enhancing lesion in the left posterior column (FIGS. 11A-11E).

Figures 12A, 12B, 12C, 12D:
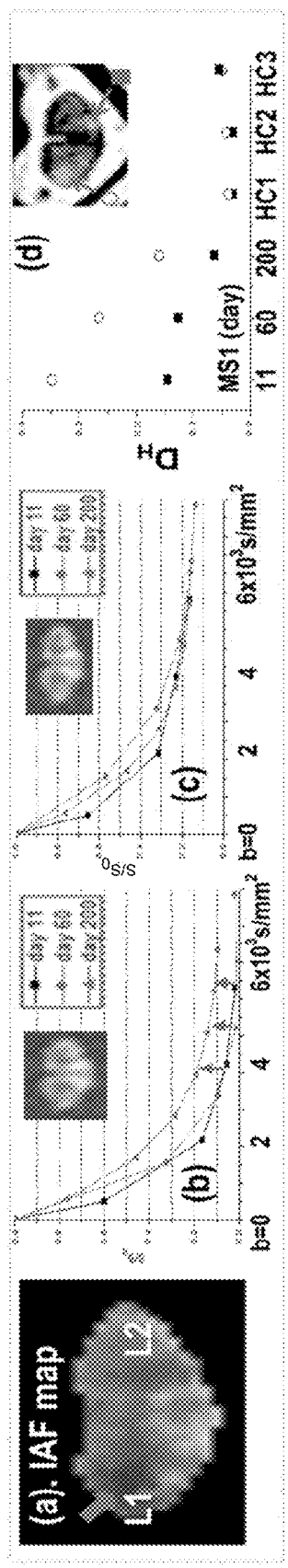
FIGS. 12A-12D show the evolution of the right lateral corticospinal tract lesion on the T2WI and UHb-rDWI. (A) IAF and (B,C) rDWI signal-b curves for two contralateral WM pixels in lesion (L1) and normal appearing WM (L2). The signal-b curves of two single pixel ROIs of MS1 at the (B) lesion region and the (C) normal region of the corticospinal tract evolve over days 11, 60 and 200 after an acute attack. (B) The curve in the lesion increases toward that of normal. (D) At b values greater than 4000 mm$^2$/s, the D$_H$ values measured in lesion L1 approach those of the healthy CSC (HCx) over 200 days.
Figure 13B:
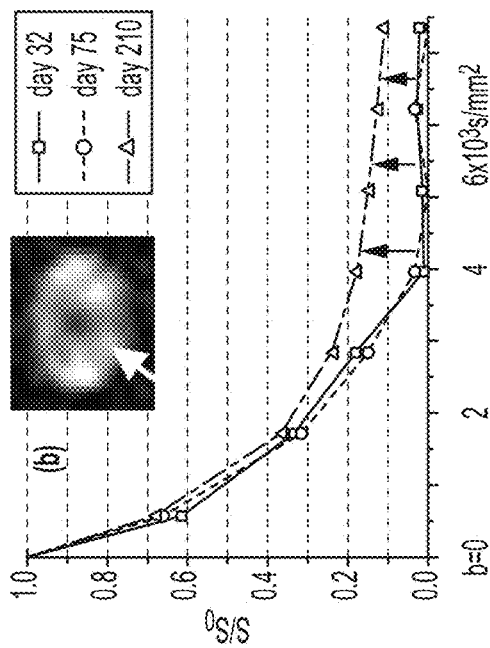
Figure 13C:
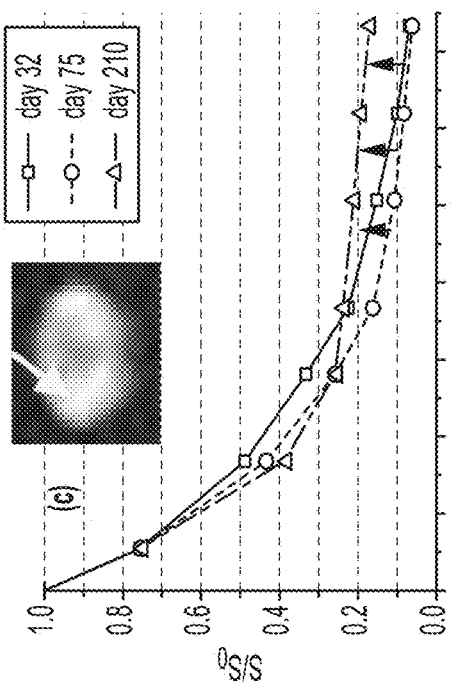
Figures 14A, 14B, 14C:
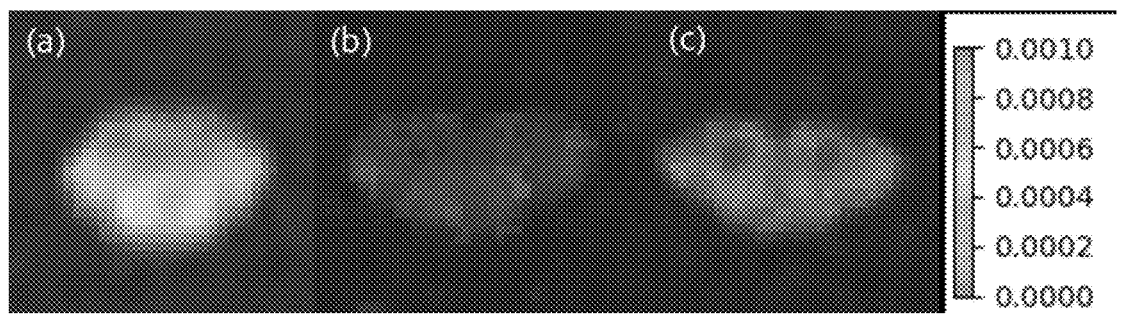
FIGS. 14A-14C show D$_H$ maps at the C3-C4 level of a healthy control (A) and MS1 patient at day 60 (B) and at day 200 (C). The color scale denotes the degree of high b decay constant D$_H$ (mm$^2$/s). The color map at day 60 (B) exhibits the greatest extent and intensity of the signal abnormalities in the right lateral corticospinal tract but also reveals other regions of change in the CSC. (B) The high D$_H$ in/near gray matter may be due to the demyelination of the anastomosing white matter tracts. (C) The color map at day 200 shows decrease in the intensity of signal abnormalities, particularly in the right lateral corticospinal tract.

FIGS. 12A-12D reveal evolution of the right lateral corticospinal tract lesion on the T2WI and UHb-rDWI. As shown in FIG. 12A, the intra-axonal fractional (IAF) map, constructed from UHb-rDWI data, shows markedly reduced IAF values in right lateral enhancing, T2 hyperintense lesion (L1). The plots in FIG. 13B-C from UHb-rDWI (inserts) indicate the time evolutions of signal-b curves of two selected contralateral pixels (red), including a pixel within L1. The UHb-rDWI signal in the selected pixel in FIG. 12B shows a prominent decaying pattern compared to that for the contralateral pixel in FIG. 12C. This pattern of signal decay is similar to the MCS findings of a demyelinating lesion. The abnormal corticospinal tract UHb-rDWI was observed multiple levels (C2-C4). In FIG. 12B, the blue signal-b curve of the lesion (L1) at day 200 approaches that of the normal region, which is concordant with the patient's return to clinical baseline. UHb-rDWI of the relatively unaffected contralateral corticospinal tract exhibited signal intensity curves similar to that of the normal volunteer. FIG. 12D demonstrates that, at b values greater than 4000 s/mm$^2$, the acute right corticospinal tract lesion and the older left posterior column lesion show rapid decay constant $D_H$ as compared to the healthy CSC. Over 200 days, the $D_H$ values approached that of the healthy CSC. The color maps reveal not only the most prominent extent and intensity of the abnormalities in the right corticospinal tract and other regions of change in the CSC but also show the evolution of the signal abnormalities (FIGS. 14A-14C).

Figure 13A:
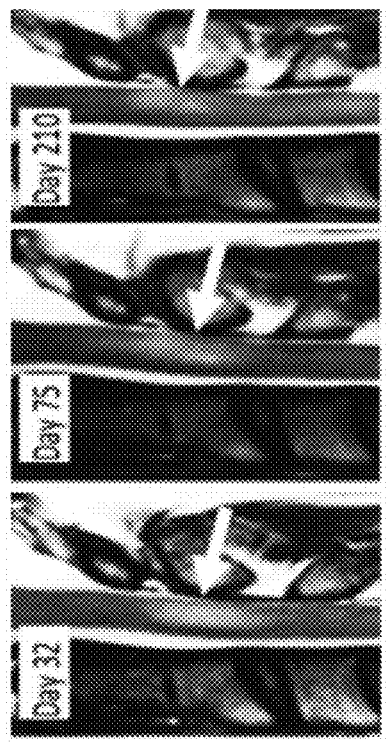
FIGS. 13A-13D show data obtained from imaging of a RRMS patient. (A) Sagittal T2WI images at days 32, 75, 210. The posterior column T2 hyperintense lesion (yellow arrow) is decreased in size. Signal-b curves of two single pixels, (B) one in posterior column lesion and (C) one in the right corticospinal tract over same time period. (B,C) The curves at day 210 increased toward that of normal. (D) At b values greater than 4000 mm$^2$/s, the D$_H$ values measured in the acute posterior column lesion and lateral corticospinal tracts are comparable to that of healthy CSC (HCx) over 200 days.
Figure 13D:
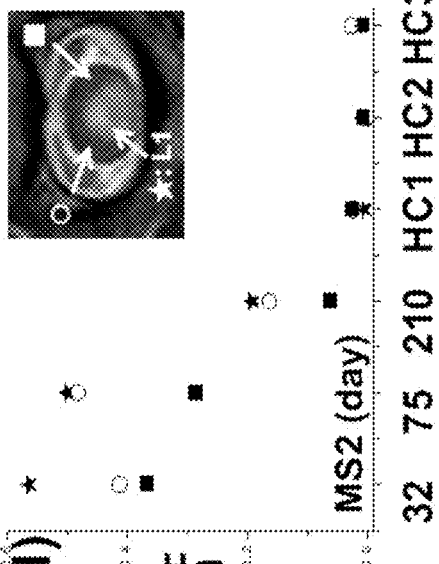
Figures 15A, 15B, 15C:
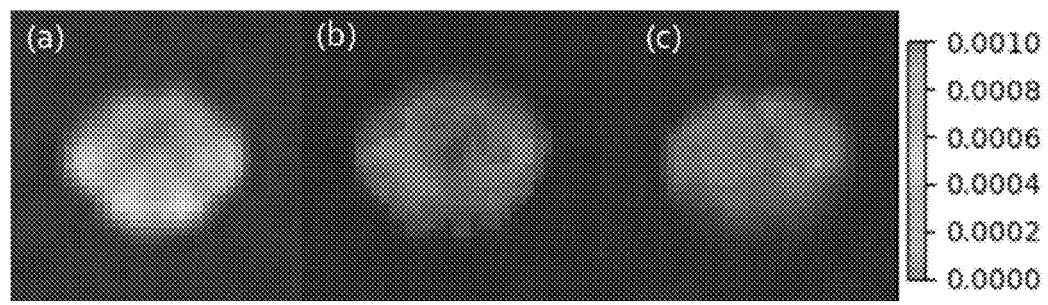
FIGS. 15A-15C shows D$_H$ map at the C2 level of a healthy control (A) and MS2 patient at day 75 (B) and at day 210 (C). The color scale denotes the degree of high b decay constant D$_H$ (mm$^2$/s). (B) The color map at day 75 demonstrates that the extent and intensity of the abnormalities are most pronounced in bilateral posterior columns and reveals substantial regions of change throughout the CSC cross-section. (B) The high D$_H$ in/near gray matter may be due to the demyelination of the anastomosing white matter tracts. (C) The color map at day 210 shows decrease in the intensity of signal abnormalities, particularly in bilateral posterior columns.
Figure 16A:
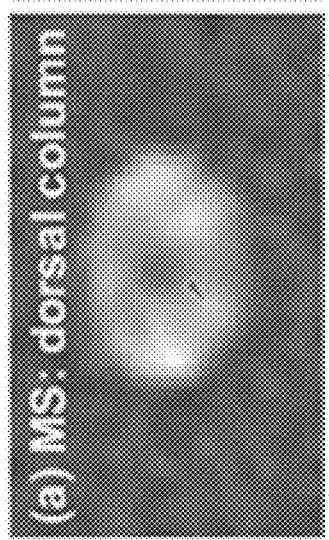
FIGS. 16A-16F show the signal-b plot of a pixel in the right posterior column (c) of the MS2 patient on day 32 illustrates continuous decay and lower signal at high-b values as compared to a similar region in the healthy CSC. This indicates increased exchange between IA and EA spaces due to the demyelination. The signal-b behavior in the right corticospinal tract (f) also shows similar behavior with continuous decay and lower values at high-b as compared to a similar region in the healthy CSC.
Figure 16B:
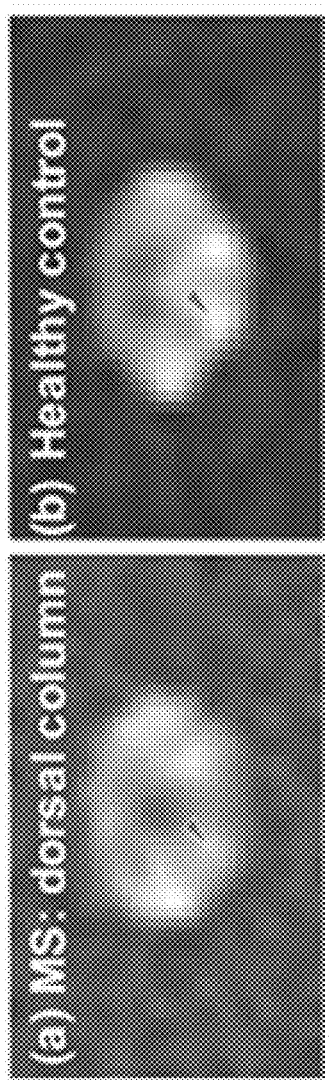
Figure 16C:
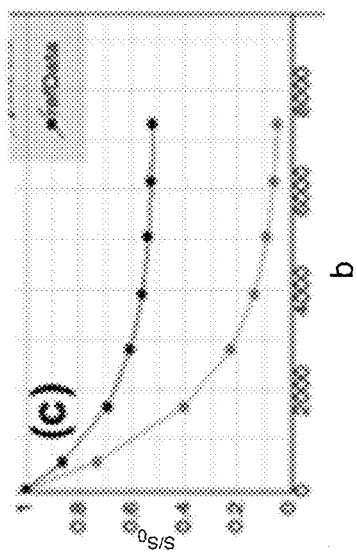
Figures 16D, 16E, 16F:
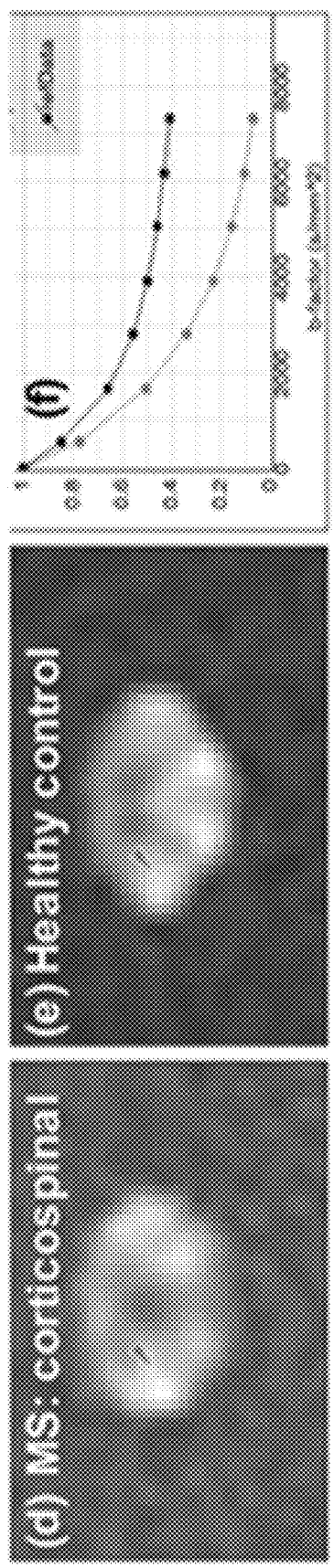
Figures 18A, 18B:
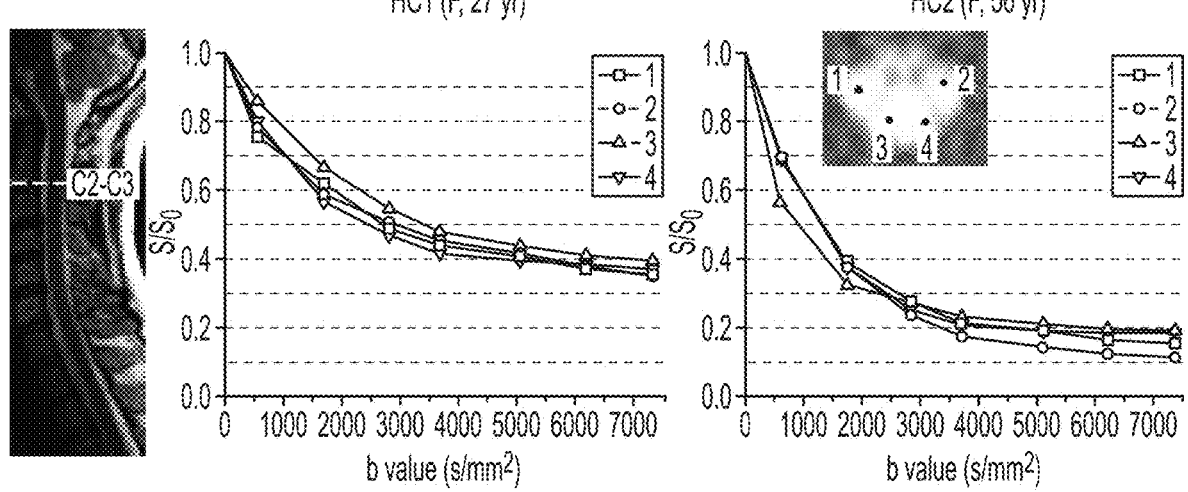
Figures 18C, 18D:
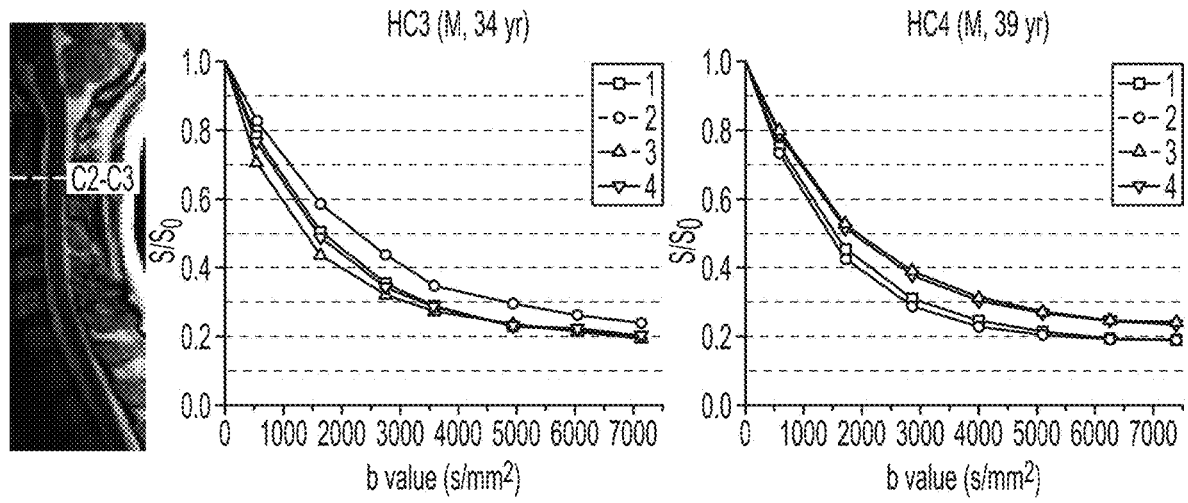
Figure 18E:
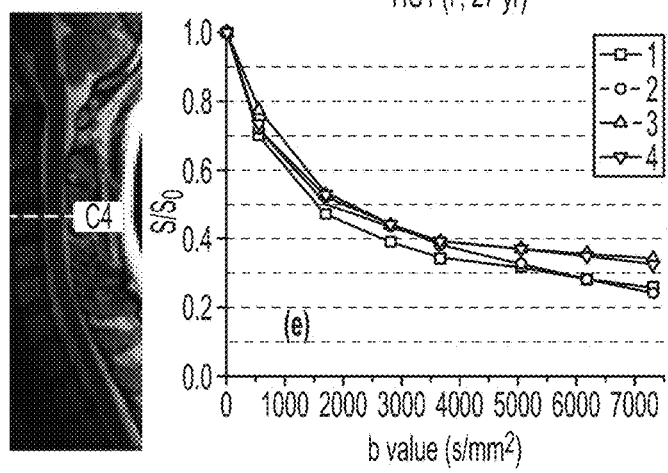
Figure 18F:
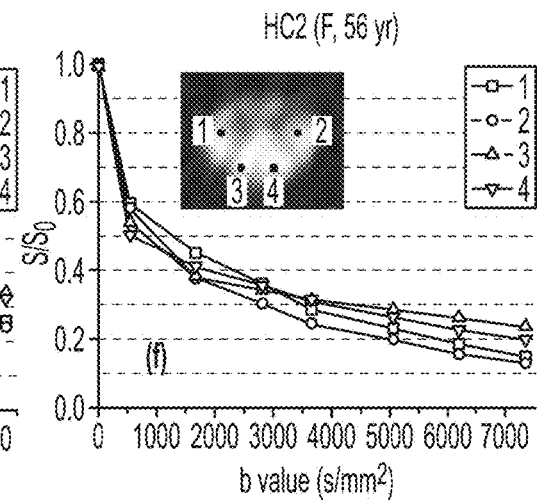
Figure 18G:
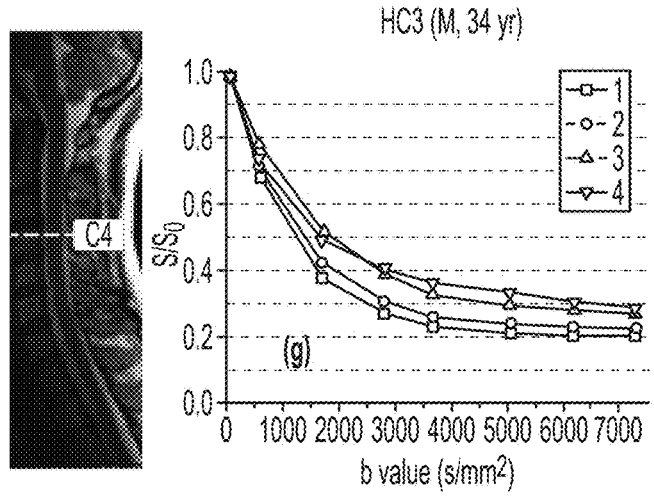
Figure 18H:
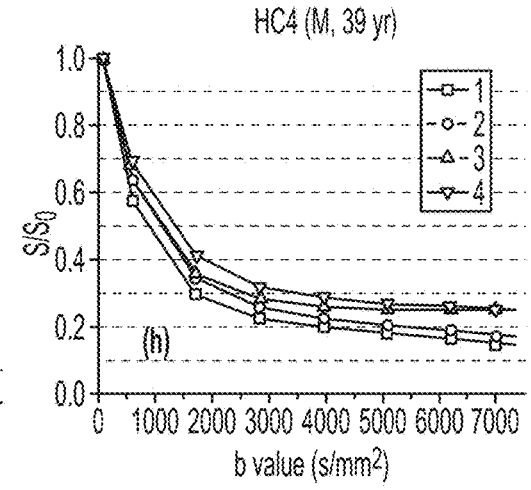

The second RRMS patient (MS2) was imaged four times, including day 1 after the initial attack then subsequently on days 32, 75, 210. On the initial clinical MRI, the sagittal T2WI showed an ovoid hyperintense lesion in the posterior spinal cord at the C2 level when she presented after an acute attack (FIG. 13A). The craniocaudal extent and conspicuity of the lesion decreased over the serial scans. The T2 hyperintensity indicates increased parenchymal water content only. FIG. 13B illustrates evolution of the signal-b curves in the posterior column lesion over time, while FIG. 13C shows evolution of the signal-b curves in the right corticospinal tract during the same time period. The curves for days 32 and 75 in FIG. 13B mimic rDWI with increased water exchange between IA and EA spaces, as is seen with a demyelinated nerve. The signal-b curve at day 210 approached normal values. The right corticospinal tract also demonstrated abnormal UHb-rDWI extending over multiple levels (C1-C3), although this area did not reveal abnormal T2 signal intensity. FIG. 13D shows that, at b values greater than 4000 s/mm$^2$, the acute posterior column lesion and lateral corticospinal tracts demonstrate rapid high-b decay constant $D_H$ as compared to the healthy CSC. On day 210, the $D_H$ values approached those of the healthy CSC. The color maps reveal not only pronounced signal abnormalities in bilateral posterior columns and substantial regions of change throughout the CSC cross-section but also show the decrease in intensity with time due to remyelination (FIG. 15A-15C).

D. Discussion

Conventional MRI is used for diagnosing MS and monitoring its evolution as well as treatment effects. MRI of the spinal cord is important for the differential diagnosis and prognosis of the disease. The upper CSC is most frequently affected, although lesions can be seen at any level. Gadolinium-enhanced lesions are most often seen in the CSC. Most lesions involve the lateral and posterior columns and, less commonly, the gray matter. The presence of spinal cord lesions is predictive of conversion to clinically definitive MS in radiologically isolated syndrome and in patients with clinically isolated syndrome. However, the correlation between clinical manifestations and conventional MRI findings is often weak to moderate. The disclosed MRI techniques provide higher specificity toward the heterogeneous pathological substrates of the disease and greater understanding of MRI features that determine irreversible disability. Such techniques can be used to identify imaging biomarkers for monitoring disease progression and treatment efficacy.

Diffusion weighted imaging, a quantitative technique that exploits the diffusion of water molecules within biological tissue, can be used to assess microstructural architecture of the spinal cord. Various structures (cell bodies, membranes, glia, inclusions, macromolecules, etc.) affect the free movement of water molecules. In diffusion tensor imaging, axial diffusivity along the principal axis and radial diffusivity along the minor axes characterize water diffusion in terms of a tensor. The magnitude of diffusion is indicated by the mean diffusivity, and the degree of anisotropy as measured by the fractional anisotropy (FA) reflects tissue organization. For the one-dimensional morphology of the spinal cord, the principal direction of DW signal is along the nerves.

With UHb-rDWI, DW signals are measured perpendicular and parallel to the nerve fiber in the same or less time than measuring the DW images along many directions in the three-dimensional space. UHb-rDWI can be measured using multiple b-values with the gradient (GD) perpendicular to the cord direction (b radial=0~10000 s/mm$^2$) and with the GD parallel to the cord direction (b axial=0~2500 s/mm$^2$). The non-mono-exponential signal decay in the WM yields increased GM-WM contrast at higher b values. From this UHb-rDWI data, conventional DTI metrics ($\lambda_r$, $\lambda_a$, FA) can be also calculated using b=0 and a low b images. The signal behavior of rDWI with respect to b-value can be used to measure the IAF and water exchange rate between the IA and EA spaces. IAF, however, was misrepresented at the lesion where the water exchange is high. In addition, the signal-b curve of axial DWI, after high-B radial diffusion filtering, provides information about the axonal damage.

The measured data for UHb-rDWI, including the high-b decay constant $D_H$, provides much deeper insight about the microscopic environment in the WM in addition to $\lambda_r$, $\lambda_a$, FA.

At the microstructural level, the movement of IA water molecules is highly restricted by the myelin sheath. The hydrophobicity of the myelin sheath, consisting of many lipid-bilayers, confines charged ion particles within the IA space, except at the nodes of Ranvier. The maximum distance IA water molecules can travel perpendicular to the nerve direction is the mean diameter of the axons (~1.2 µm). Although water diffusion is somewhat hindered by organelle membranes with a fewer lipid layers, water molecules are still able to travel through those boundaries. Therefore, for the UHb-rDWI, the CSC WM can be compartmentalized into (1) "restricted" IA space where water cannot move more than the diameter of the axon; and (2) all other "mobile" space where water can move through the hindered boundaries, including the membranes. At sufficiently high DW (b>~4000 s/mm$^2$ in a clinical MRI system) and with echo-time greater than ~50 ms (>5*T$_2$), DWI signal from "mobile" water protons in EA and myelin space completely suppressed to background noise level, leaving only the signal contributed from IA water. This behavior was observed on radial UHb-rDWI in both the in-vivo and ex-vivo CSC. In pathologic processes of the CSC WM, particularly in the acute stage, there can be local infiltration of immune cells. As the molecular diffusivities of these cells differ from other spaces, this can influence the signal behavior of the low-B and axial DWI, but UHb-rDWI is not affected. Water molecules are still able cross the boundary of these cells fairly easily, compared with those confined within the IA space in healthy CSC. The water molecules within these additional environments act as "mobile" water for radial UHb-rDWI.

In MS, the permeability and geometry of the structural barriers to water movement in the brain and spinal cord can be altered. In addition to demyelination and varying degrees of remyelination, there is the histopathology of axonal damage, which includes decreased axonal density, increased residual axonal diameter, and increased distance between axons. Based on experiments using high-resolution DTI with immunohistochemistry on human ex-vivo CSC of a multiple sclerosis patient, each of these findings can affect the characteristics of water diffusivity within the CSC. Higher mean diffusivity was shown in spinal cord lesions in MS patients as compared to normal spinal cord. Myelin breakdown was associated with increased radial diffusivity, whereas axonal damage was shown to decrease fractional anisotropy. Axial diffusivity is increased or decreased according to the stage of the insult and the architecture of the underlying fibers.

UHb-rDWI has the advantage of reflecting changes in the EA and IA spaces at lower values and only the IA space at higher b values. In the normal CSC, the signal from the EA space decayed while that from the IA space was constant, despite the b values. The results also show that UHb-rDWI is consistent over time for imaging of major white matter tracts in the normal CSC in vivo. In the RRMS patients, the regions affected by active lesions revealed marked decrease in signal intensities in the UHb zone. The results show that the applied radial diffusion gradient does not create noticeable phase dispersion for the spins in restricted water molecules in the IA space whose motion along radial direction is limited by axonal diameter while it does for the spins in mobile water molecules in EA space. Demyelinating lesions enable the exchange of water molecules between IA and EA spaces, which results in the marked signal decay in the IA space (FIGS. 16A-16F). In RRMS patients, UHb-rDWI revealed the extent of lesions in the CSC during acute relapse and over the course of the recovery period. The MCS data suggests that this rapid decay in the MS lesions and eventual increase towards the $D_H$ of the normal control indicates demyelination with axonal sparing and remyelination. Additionally, the UHb-rDWI color mapping of the decay pattern demonstrated the extent and intensity of CSC involvement and evolution of the lesions over time.

The UHb-rDWI technique also permits interrogation of the CSC microstructure in normal and disease states in correlation with clinical status. Abnormalities in diffusivity in the corticospinal tracts and in the posterior columns were shown to be associated with locomotor disability and sensory impairment. This is similar to the MS1 patient that had a right lateral corticospinal tract lesion and presented with right lower extremity paresthesias and weakness. The MS2 patient had posterior column lesions and presented with impaired balance and sensory complaints. Gray matter DTI abnormalities are associated with more severe clinical impairment and the presence of the secondary progressive phenotype. Lower radial diffusivity at baseline of a spinal cord relapse, with improvement in the subsequent six months, has been associated with better clinical outcome, which reflects resolution of inflammation and remyelination. In the present Example, the UHb-rDWI signal-b plots in the lesions of both patients MS1 and MS2 at three time points demonstrated increase of the curves toward normal, which was concordant with the recovery of the MS patients. The plateau of the signal-b curve may represent axonal density, which decreases with inflammation, and the exponential decay of the signal-b may reflect demyelination with exchange of water between the EA and IA space. These results illustrate the ability of UHb-rDWI to detect the evolution of MS lesions from acute demyelination with axonal sparing to the axonal preservation with remyelination.

Although gadolinium enhancement with increased diffusivity is typically interpreted to reflect an acute lesion, a portion of demyelinating lesions can be characterized by an early restricted diffusivity that may not be associated with enhancement. This can reflect cytotoxic edema and increased cellularity with varying degrees of blood-brain/cord barrier breakdown. In acute lesions, which may be subtle on conventional imaging and may not enhance, the UHb-rDWI can be helpful in understanding the microstructural changes as they evolve by reflecting changes in the EA and IA spaces.

UHb measurements can be useful for monitoring lesion evolution, recovery, and response to therapy. While spinal cord inflammation can resolve and demyelination can be partly reparable secondary to remyelination, axonal loss is irreparable and the principal cause of disability in MS and related neurological diseases. Thus, as disclosed herein, a clear marker can be established to distinguish demyelination from axonal loss. The height of the plateau can be useful in distinguishing the inflammation from demyelination. Based on MCS results, the height of the plateau decreases with inflammation as the axonal density decreases with inflammation, while demyelination causes the signal-b curve to decay exponentially, much like EA water. The height of the plateau is also useful for evaluating the degree of remyelination in a lesion with axonal sparing.

Improved imaging results can be obtained in the upper CSC where the spinal alignment is straight. With normal cervical lordosis in the mid and lower cervical spine, there can be field inhomogeneity with distortion. Therefore, adjustments can be made to accommodate for the cervical spine curvature below C4.

The results showed that signal at higher b values are from the IA space. UHb-rDWI revealed the extent of CSC lesions during acute relapse and recovery, and the concordance of the UHb-rDWI patterns with clinical recovery raises speculations of the histological correlations of remyelination and axonal preservation. Axonal damage can be assessed by applying the UHb diffusion gradients along axial direction.

E. Conclusion

The consistency of UHb-rDWI in the normal control CSC on two successive scans demonstrates the reproducibility of the disclosed technique or method. The reliability of UHb-rDWI to show demyelination is illustrated by the abnormal quantitative diffusion values in the MS patients relative to the normal subjects. The concordance of the clinical findings in correlation with serial UHB-rDWI signal-b plots of the lesions indicates the ability of UHb-rDWI to detect the evolution of demyelination with axonal sparing to axonal preservation with remyelination in MS lesions.

Example 4: Ultra-High-b Radial Diffusion Weighted Imaging (UHb-rDWI) of the Human Cervical Spinal Cord A. Introduction Injury in the spinal cord can include local demyelination and/or axonal damage and lead to varying degrees of neurologic deficit, which can cause the persistent disability in the patient. Despite the contrast and spatial resolution provided by magnetic resonance imaging (MRI), conventional MRI sequences such as $T_1$- and $T_2$ weighted imaging are limited in their ability to detect early stages of spinal cord disease when clinical symptoms can be vague. Therefore, the disclosed method for identifying a non-invasive imaging biomarker can be used for earlier disease detection, monitoring disease evolution, and treatment of patients with injuries of the spinal cord.

Diffusion tensor imaging (DTI) is considered as a promising method to evaluate white matter integrity and pathology. Quantitative DTI metrics, such as radial and axial diffusivities, and fractional anisotropy (FA) (5), may serve as biomarkers for the demyelination and axonal loss in the spinal cord diseases. Unlike the brain where overlapping of crossing fibers in multiple orientations require DW signal measurement along many different directions to compute DTI metrics, for the spinal cord, in which nerve fibers are one-dimensional and the principal direction of local symmetry is along the cord direction, DW signal measurements along the directions perpendicular and parallel to the nerve fiber are sufficient. These measurements using the conventional DTI are limited with respect to the specific details of neuropathology and microstructural architecture and are not always consistent in detecting the axonal dysfunction (6-9). For instance, the decreased FA assessed with DTI for the spinal cord lesion cannot distinguish whether it is caused by increased water content in the extra axonal (EA) space (edema) or by increased water exchange between intra-axonal (IA) and EA spaces due to demyelination or by both. Also, the measured radial diffusivity is not objective, but dependent on b-values because of different signal contributions from IA and EA spaces at different b-values.

Unlike the brain, MR imaging of the cervical spinal cord (CSC) is technically challenging because of a small cross-sectional area, susceptibility artifact due to cord-vertebral bone interface, chemical-shift artifact arising from the fat in the vertebral bones and other nearby structures, and motion induced artifact resulting from cerebrospinal fluid (CSF) pulsation, breathing, swallowing during the measurement. The variant magnetic susceptibility artifact particularly limits the capability of diffusion-MRI (DWI, DTI) of CSC using 2D single-shot diffusion-weighted EPI (2D ss-DWEPI), which is commonly used for brain.

While the conventional DTI measures and evaluates the DWI at low-b region, where the extra-axonal water dominates the signal behavior, ultra-high-b DWI provides better contrast between white matter (WM) and gray matter (GM) with greater diffusion weighted and less $T_2$ weighted effect. A pair of strong diffusion gradients, separated by a long diffusion time, can sensitize the water exchange effect, which is predicted by a Monte-Carlo simulation of water diffusion MRI in an one-dimensional white-matter. This technique can produce DW images with greatly reduced: (a) geometric distortion, which is caused by susceptibility difference at/near the interface between bone/tissue and common in EPI-type acquisition, by implementing reduced field of view (FOV) in the phase encoding direction, (b) the motion induced artifact using single shot acquisition, and (c) acquisition time by acquiring multiple slices within a single repetition time (TR) thereby making the sequence amenable for clinical purposes.

The radial diffusivity, i.e., diffusivity perpendicular to the cord, depends on b-value and relative concertation of intra axonal (IA) and extra axonal (EA) spaces. Because of long echotime TE in clinical MRI system due to the limited gradient strength, say larger than 50 ms for b>500 s/mm², the signal from the myelin water, of which $T_2$ is short (<10 ms), is mostly suppressed to noise-level. Therefore, no matter how heterogeneous the physical environment is inside the CSC white-matter, for the "radial DWI", the WM can be compartmentalized into: (1) water molecule "restricted" in IA space by myelin sheath where water cannot move more than an inner-diameter of the axon (~4.5 µm) (18), and (2) "mobile" water in EA space where water can move over the hindered boundaries including the membranes. As demonstrated herein, the rDWI signal from the EA space of healthy CSC can decay with increasing b-values and drop to background noise level in ultrahigh-b (UHb) region (b>~4,000 s/mm² at clinical MRI system) while that from the IA space remains constant in UHb region. Thus, at UHb region and for healthy cord, if there is no exchange of water molecules between IA and EA spaces, the signal intensity measured is solely from IA space. Once the EA signal is filtered out with UHb diffusion gradient, the intra-axonal fraction (IAF) and high-b decay constant ($D_H$) of water molecules in the cord can be quantified by fitting UHb-rDWI signal to an exponential decay function, which may be used to characterize many white matter diseases. The measured rDWI signal intensity, which is the contribution from IA and EA spaces, can be expressed as $$S_r(b)=S_{EA}^0 e^{-bD_L}+S_{IA}^0 e^{-bD_H}, \quad [7]$$

where $D_L$ and $D_H$ are, respectively low- and high-b decay constants and $S_{EA}^0$ and $S_{IA}^0$ are EA and IA signal intensities without diffusion decay, respectively.

As further described herein, during applications of UHb-DWI to a small number of healthy subjects, different signal-b behaviors were observed, particularly with different high-b decay constant, at different white-matter tracts and vertebral levels. This can be due to different means of axonal diameters and/or different fractions of nodes-Ranvier at different tracts. The signal behavior of the UHb-rDWI signal were studied at different tracts and levels of the in vivo cervical spinal cord and the reproducibility of the technique was validated by scanning each subject twice.

B. Methods

MRI experiments: Four healthy volunteers (HC1, HC2, HC3, and HC4) underwent UHB-rDWI experiment twice in the interval of 2 months on a Siemens 3T MRI system (Trio, Siemens Medical Solutions, Erlangen, Germany). Each subject was positioned with the cervical segment of the spinal cord as straight as possible from the anterior/posterior view. At first, T2-weighted images of the cervical spinal cord (CSC) were acquired in axial plane (TR/TE-4 s/95 ms and acquisition resolution 0.68×0.55×4.0 mm³) and sagittal plane (TR/TE-4 s/112 ms and acquisition resolution 0.92×0.69×3.0 mm³) using a turbo spin-echo (TSE) for planning the UHb-rDWI experiment. Then, axial (diffusion gradient perpendicular to the spinal cord) high-b diffusion weighted images were acquired using the disclosed 2D singleshot Diffusion-Weighted Stimulated EPI with Reduced FOV (2D ss-DWSTEPI-rFOV) technique and a 8 channel CSC dedicated phased array RF receive-only coil. The imaging parameters were TR/TE=3 s/64 ms, FOV read/phase=128× 44 mm², acquisition time=6 min 19 sec, number of averages=6, number of slices=21, and voxel dimension=1.0× 1.0×4.0 mm³. Diffusion-weighting was applied in left-right direction with 7 b-values: 573, 1702, 2832, 3691, 5090, 6219, and 7348 s/m² using fixed amplitude (38 mT/m) and duration (12 ms) of the diffusion gradient while varying mixing times TMs (time interval between $2^{nd}$ and $3^{rd}$ 90° RF pulses) with 9, 85, 161, 237, 313, 389, 465 ms, respectively. Spatial saturation bands were applied anterior and posterior of the CSC to suppress the signal contamination from outside of the FOV. An additional $1)_0$ image without diffusion weighting gradient (b~0 s/mm²) was obtained corresponding to each TM for correcting $T_1$ decay during TM.

$T_1$ correction: In 2D ss-DWSTEPI imaging, diffusion-weighted longitudinal magnetization undergoes $T_1$ decay during the mixing-time. The signal equation for b-value images ($S_b$) and $b_0$ images ($S_{b_0}$) incorporating the diffusion and $T_1$ decay effects are:

$$S_b = (S_{EA}^0 e^{-bD_L} + S_{IA}^0 e^{-bD_H})e^{-TM/T_1} \quad [8]$$

$$S_{b_0} = S_0 e^{-TM/T_1} \quad [9]$$

where $S_0$ is the signal measured without $T_1$ and diffusion decay, and D is an apparent diffusion coefficient (ADC). The b-value signal undergoes both diffusion and $T_1$ decay, while $b_0$ signal undergoes only $T_1$ decay. The pure diffusion signal can be obtained by dividing equation [8] by equation [9].

Curve fitting: All DICOM images were post processed using home-built processing software written in python language. The signals from each pixel of $b_0$ image were fitted with bi-exponential function while that from b-value images were fitted with either bi-exponential or mono-exponential plus constant function, depending on a signal that best fits to either of these functions, and the curves were normalized to the $S_0$. In particular, for demyelination pixel such as in multiple sclerosis (MS) lesion, where $S_{IA}^0/(S_{IA}^0+S_{EA}^0)<0.1$, the processing software was instructed to fit the signal-b curve to a mono-exponential plus constant function. The diffusion only curve can be obtained by dividing the normalized fitted curve of each pixel of b-value images that has both $T_1$ and diffusion decay by corresponding normalized fitted curve of $b_0$ images that has only $T_1$ decay.

C. Results

The series of b-value images at C3-C4 level of four volunteers (top series: volunteer HC1, middle series: volunteers HC2 and HC3, and bottom series: volunteer HC4) corresponding to the seven b-values are shown in FIGS. 17A-17D. Greater contrast between white matter and gray matter is seen at higher-b rDWI. At $b_{max}$=7348 s/mm², GM signal drops to noise level while enough WM signal is preserved.

FIGS. 18A-18L show the rDWI signal-b curves of four volunteers at different levels of the CSC: upper curves at C2-C3 level, middle at C4 level, and bottom at C5 level. The curves at the $1^{st}$, $2^{nd}$, $3^{rd}$, and $4^{th}$ columns are volunteers HC1, HC2, HC3, and HC4, respectively. Four one point pixel (1×1×4 mm³) ROIs: two on the corticospinal tracts (points 1 and 2) and two on the posterior columns (points 3 and 4) were taken for plotting signal-b curves. These points were chosen, ensuring minimal signal contamination from boundary and GM due to partial volume effects. The data show that the signal-b curves decay at initial-b values and reach plateau at high-b values. The plateau height of the curve varies slightly between different tracts within the same spinal cord section and on different vertebral levels while it is similar on left and right tracts within the same section. Moreover, the plateau heights in the corticospinal tracts and posterior columns of one volunteer, a younger female, are consistently higher than those of the other healthy subjects most prominently at C3-4 level and to a lesser extents at the middle C4 as well as C5 levels. This inter subject variability on the plateau of the signal-b curve can be due to various factors including as age, gender, and/or cord morphology.

Figures 19A, 19B, 19C:
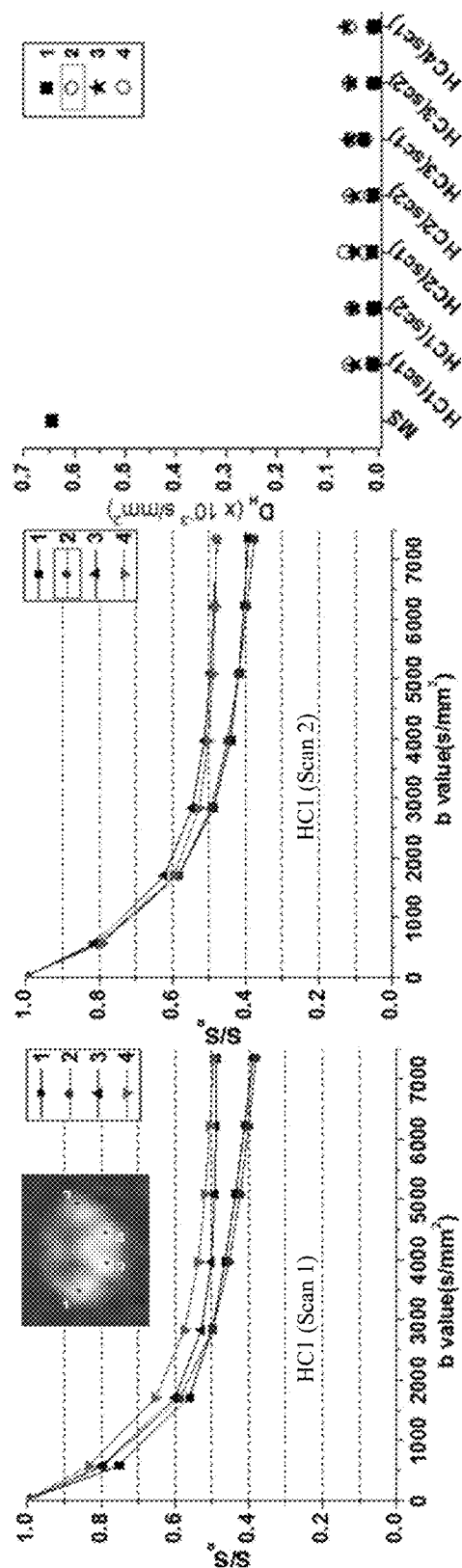
FIGS. 19A-19C show a rDWI signal-b plot comparison between two scans: (A) scan 1 and (B) scan 2 at C3-C4 level in HC1. The plots are consistent in two successive scans, indicating high reproducibility of the measurement. Similar behavior of the curve was seen on all levels of the spinal cord and on other volunteers HC2, HC3, and HC4. (C) $D_H$ values measured at two regions of the corticospinal tracts (1, 2) and at two points of the posterior columns (3, 4). Five-pixel ROIs (diamond shaped) at corticospinal tract and 3-pixel ROIs (on vertical line) at posterior column are used to measure $D_H$.
Figures 20A, 20B, 20C:
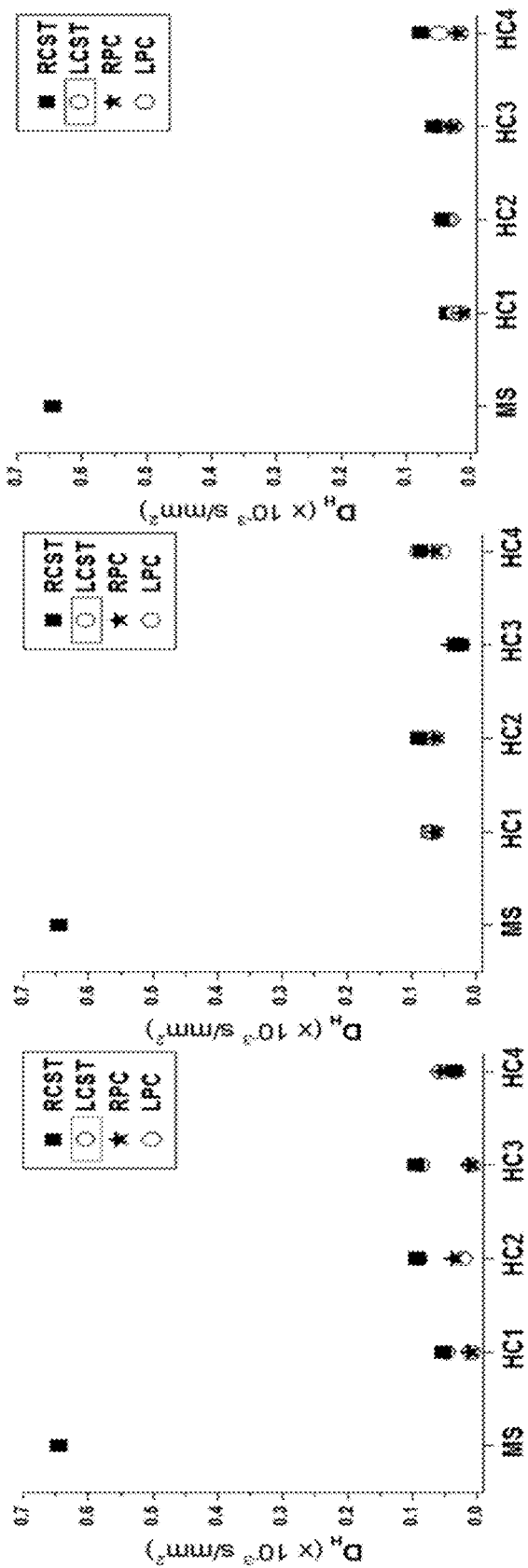
FIGS. 20A-20C show scatter plots of $D_H$ values of Table 3, as disclosed herein, of 4 healthy volunteers at (A) C2-C3, (B) C4 level, and (C) C5 levels. The DH values of the control volunteers at different levels are compared with that obtained from multiple sclerosis (MS) patient with lesion on right corticospinal tract at C3-C4 level.

FIGS. 19A-19C show the comparison of signal-b curve at two successive scans of volunteer HC1 at C3-C4 level. As shown, the plots are consistent in two time points. The consistency over time was also observed at other vertebral levels. This reproducibility of signal-b curves behavior between two time points was observed in all vertebral levels of other volunteers. FIGS. 19A-B are the representative of all curves at different levels of all volunteers under study. FIG. 19C shows the scatter plot of $D_H$ values measured at four regions: two on the corticospinal tracts with diamond shaped 5 pixel ROIs centered at point 1 and 2 (shown in rDW image in FIG. 19A) and two on posterior column with three pixel ROIs on vertical line centered at points 3 and 4. Both curves and $D_H$ values are nearly identical on left and right tracts and in two scans. The $D_H$ values measured on these 4 regions in C2-C3, C4, and C5 levels of all volunteers are listed in Table 3 and plotted in FIG. 21. The $D_H$ values of the healthy volunteers at C3-C4 are compared with the $D_H$ value from a lesion right corticospinal tract of MS patient at C3-4 FIGS. 20A-20C. This example demonstrates that variability in the $D_H$ values of healthy controls is low compared to the $D_H$ value in the lesion from a multiple sclerosis (MS) patient.

TABLE 3

Regional $D_H$ Values In Cervical Spinal Cord Tracts In Healthy Controls.

| volunteers | Levels | RCT | LCT | RPC | LPC |
|---|---|---|---|---|---|
| HC1 | C2-C3 | 0.0533 | 0.0478 | 0.0100 | 0.0100 |
| HC2 | | 0.0939 | 0.0920 | 0.0353 | 0.0222 |

TABLE 3-continued

Regional $D_H$ Values In Cervical Spinal Cord Tracts In Healthy Controls.

| volunteers | Levels | RCT | LCT | RPC | LPC |
|---|---|---|---|---|---|
| HC3 | | 0.0951 | 0.0877 | 0.0100 | 0.0100 |
| HC4 | | 0.0363 | 0.0332 | 0.0541 | 0.0572 |
| HC1 | C4 | 0.0732 | 0.0705 | 0.0632 | 0.0664 |
| HC2 | | 0.0904 | 0.0828 | 0.0626 | 0.0658 |
| HC3 | | 0.0252 | 0.0243 | 0.0391 | 0.0291 |
| HC4 | | 0.0868 | 0.0887 | 0.0648 | 0.0544 |
| HC1 | C5 | 0.0375 | 0.0246 | 0.0127 | 0.0162 |
| HC2 | | 0.0451 | 0.0314 | 0.0436 | 0.0375 |
| HC3 | | 0.0571 | 0.0519 | 0.0286 | 0.0269 |
| HC4 | | 0.0786 | 0.0488 | 0.0194 | 0.0182 |

D. Discussion

The UHb-rDWI technique using a CSC dedicated coil permitted high resolution UHb-rDW images of CSC to be obtained in four healthy control volunteers, with clear distinction between WM and GM at high b diffusion MRI. The increased GM-WM contrast at high b can be due to the non mono-exponential signal decay in the WM. The MCS result predicts the constant signal intensity in UHb-rDW images of white matter. The decreasing signal intensity of WM observed in UHb-rDW images at higher b-value can also be caused by imperfect $T_1$ decay at high b-value images. The signal intensity of b-value images of volunteer HC1 is higher than that of others, which can be due to factors such as different tuning, coupling, loading of the RF coil, and depth of the spinal cord from the skin surface.

The signal-b curve plotted at various levels of spinal cord shows the bi-exponential decay behavior, i.e. fast exponential decay at lower b-values and much slower decay at high b region, say b>4,000 s/mm² in a clinical MRI system using a CSC dedicated RF coil. The diffusion signal from the EA space decays with increasing b-values while that from the IA space decays very slowly at high-b for the normal healthy spinal cord. Thus, the behavior of signal-b curve at low b-value is mainly predominated by fast decay of diffusion signal from EA space while at UHb-value the signal behavior is governed solely by the constant or slow-decaying signal from IA space. The axons in the healthy spinal cord are surrounded by the myelin layers which prohibit or greatly limit the exchange of water molecules between IA and EA spaces. The applied radial diffusion-weighting does not create a noticeable phase dispersion that is responsible for signal decay for the spins in restricted water molecules in the IA space whose motion along the radial direction is limited by axonal diameter (~4.5 μm), while it does create a phase dispersion for the spins in mobile water molecules in EA space where water can move over the hindered boundaries including the membranes. The myelin water does not contribute to the signal intensity of DW images because of relatively long TE used in the experiment compared to the short $T_2$ of myelin water.

The plateau of the signal-b curve can correspond to the axonal density, which is slightly different in different tracts within a spinal cord section. This can be due to the differences in axonal diameter, fiber packing density between different tracts of the section, different leakage effect due to variations in myelination of the myelinated segment, and fractions of node of Ranvier. The slightly decaying pattern of the UHb signal may be due to leakage of water molecule via nodes of Ranvier, application of imperfect rDW gradients, imperfect shielding of water by myelin, angular dispersion of axons within an imaging voxel, and technical problems such as asynchronous motion between the table and the subjects during DWI experiment. Note that each myelin segment is about 100 µm long for a 1 µm diameter axon, and a gap between two adjacent myelin sheaths, the node of Ranvier, is in the range of 0.8 to 1 µm.

As depicted in FIG. 19C, FIGS. 20A-20C, and Table 3, the $D_H$ values measured on the left and right side of the corticospinal tract and posterior column within the same section of cord are almost identical. The mean value of $D_H$ with inter/intra-subject standard deviation on corticospinal tract was $(0.0607\pm0.02531)$ $10-3$ s/mm$^2$ and that on posterior column was $(0.0357\pm0.02072)$ $10^{-3}$ s/mm$^2$, which is close to the ADC value $(0.068\pm0.021)$ $10^{-3}$ s/mm$^2$ reported on white matter. The mean $D_H$ is smaller in posterior column than that in corticospinal tract. The UHb-rDWI signal curve of the normal controls was consistent in all vertebral levels on two successive scans. The curves are very similar on the left and right sides of every tract in the spinal cord. These results demonstrate high reproducibility and reliability of the technique. In $D_H$ plots of healthy controls, their values are compared with the $D_H$ value from a 5 pixel ROI in a lesion at C3-C4 level from a representative MS patient to show that the inter/intra subject variability of healthy controls is insignificant compared to the $D_H$ at lesion. This indicates also that these imaging techniques can be used for clinical imaging of the spinal cord in demyelinating disease and other disease states.

E. Conclusion

UHb-rDWI is effective, quantitative, qualitative, and reproducible in normal healthy volunteers and provides much deeper insight about the microscopic environment in the WM in addition to the DTI matrices, which can be used for establishing an imaging biomarker to distinguish inflammation, demyelination and axonal loss in the spinal cord.

Exemplary Software and/or Hardware Configurations

As will be appreciated by one skilled in the art, the previously disclosed devices, methods, and systems may take the form of an entirely hardware embodiment, an entirely software embodiment, or an embodiment combining software and hardware aspects.

Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 21:
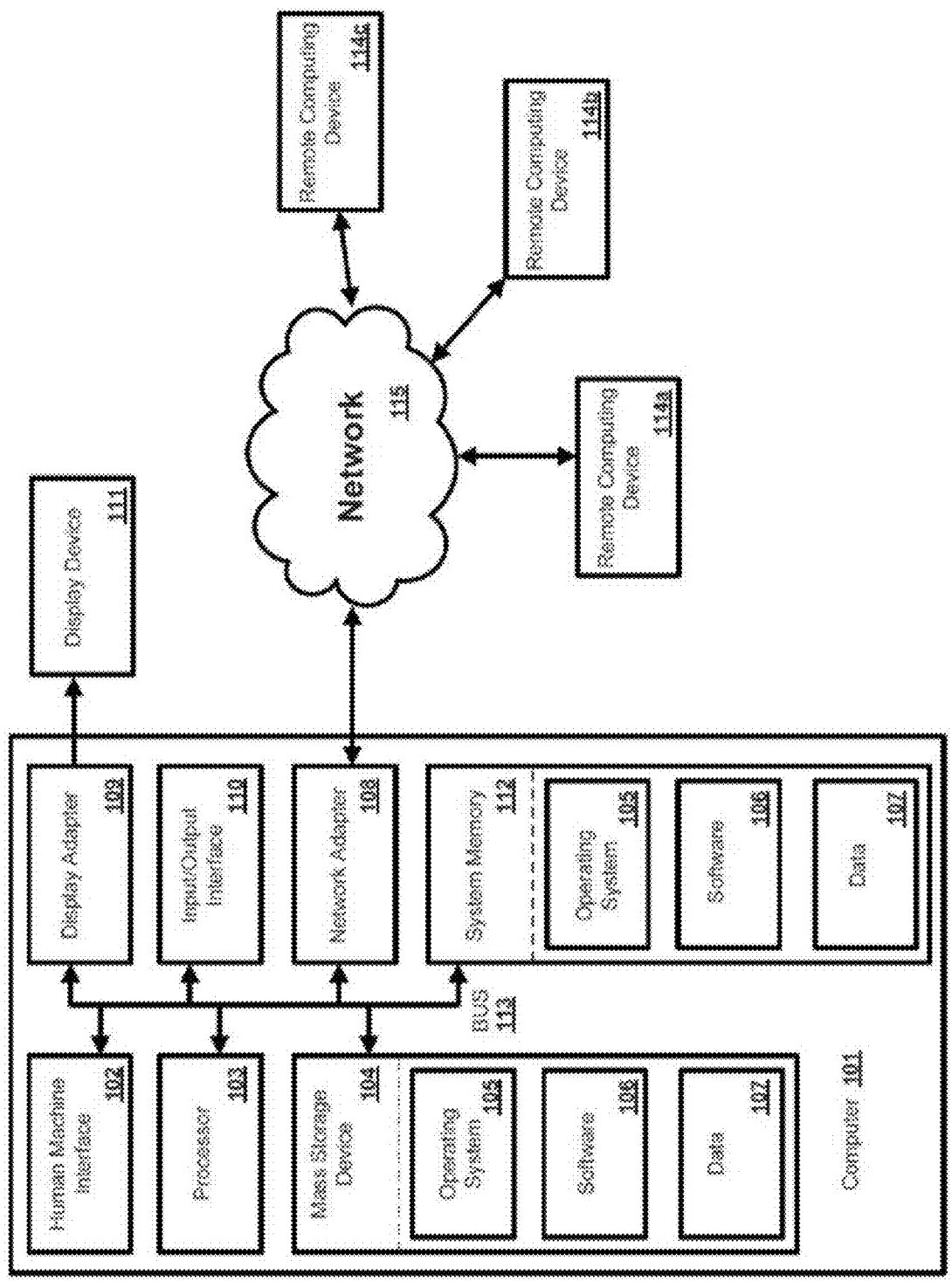
FIG. 21 is a schematic diagram depicting an exemplary computing device that can serve as a system controller or portion of a system controller as disclosed herein.

One skilled in the art will appreciate that provided herein is a functional description and that the respective functions can be performed by software, hardware, or a combination of software and hardware. In an exemplary aspect, the methods and systems can be implemented, at least in part, on a computing device 101 as illustrated in FIG. 21 and described below. By way of example, the computing device 101 can be provided as a component of a conventional MRI system as is known in the art. Alternatively, it is contemplated that the computing device 101 can be provided separately or remotely from the MRI system. In further aspects, the methods and systems disclosed can utilize one or more computing devices (e.g., computers, smartphones, or tablets) to perform one or more functions in one or more locations. Optionally, it is contemplated that the one or more computing devices can comprise at least two computing devices having respective processing units.

FIG. 21 is a block diagram illustrating an exemplary operating environment for performing at least a portion of the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices.

Generally, program modules comprise computer code, routines, programs, objects, components, data structures, etc., that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computing device 101. The components of the computing device 101 can comprise, but are not limited to, one or more processors or processing units 103, a system memory 112, and a system bus 113 that couples various system components including the processor 103 to the system memory 112. In the case of multiple processing units 103, the system can utilize parallel computing.

The system bus 113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 113, and all buses specified in this description can also be implemented over a wired or wireless network connection and each of the subsystems, including the processor 103, a mass storage device 104, an operating system 105, control processing software 106, control processing data 107, a network adapter 108, system memory 112, an Input/Output Interface 110, a display adapter 109, a display device 111, and a human machine interface 102, can be contained within one or more remote computing devices 114a,b,c at physically separate locations, connected through buses of this form, in effect implementing a fully distributed system.

The computing device 101 typically comprises a variety of computer readable media. Exemplary readable media can be any available media that is accessible by the computing device 101 and comprises, for example and not meant to be limiting, both volatile and non-volatile media, removable and non-removable media. The system memory 112 comprises computer readable media in the form of volatile memory, such as random access memory (RAM), and/or non-volatile memory, such as read only memory (ROM). The system memory 112 typically contains data such as control processing data 107 and/or program modules such as operating system 105 and control processing software 106 that are immediately accessible to and/or are presently operated on by the processing unit 103.

In another aspect, the computing device 101 can also comprise other removable/non-removable, volatile/non-volatile computer storage media. By way of example, a mass storage device 104 can provide non-volatile storage of computer code, computer readable instructions, data structures, program modules, and other data for the computing device 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 104, including by way of example, an operating system 105 and control processing software 106. Each of the operating system 105 and control processing software 106 (or some combination thereof) can comprise elements of the programming and the control processing software 106. Control processing data 107 can also be stored on the mass storage device 104. Control processing data 107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computing device 101 via an input device, such as, without limitation, a keyboard, pointing device (e.g., a "mouse"), a microphone, a joystick, a scanner, tactile input devices such as gloves, and other body coverings, and the like. These and other input devices can be connected to the processing unit 103 via a human machine interface that is coupled to the system bus 113, but can be connected by other interface and bus structures, such as a parallel port, game port, an IEEE 1394 Port (also known as a Firewire port), a serial port, a universal serial bus (USB), or an Intel® Thunderbolt.

Optionally, in exemplary aspects, the processor 103 of the controller 50 disclosed herein can receive manual inputs from a user or other individual supervising the quantitative evaluation of spinal cord injury in a subject. Such manual inputs can correspond to a desired b-value diffusion-weighting and other conventional MRI parameters, a selected threshold value for purposes of evaluating axonal condition, and subject and patient information (physical condition, age, weight, and the like). It is further contemplated that the processor 103 can be communicatively coupled to other components, such as a heart rate monitor or other monitoring device that provides physiological feedback (e.g. heart rate) or other parameter measurements to the processor 103. It is still further contemplated that the processor 52, 103 can be communicatively coupled to a memory as further disclosed herein that stores a pre-set profile corresponding to the user or subject/patient. In operation, the processor 52, 103 can make use of these instructions to provide a customized profile for the user or subject/patient and ensure that any adjustments to the application of b-value diffusion-weighting or other parameters are consistent with the instructions.

In yet another aspect, the display device 111 can also be connected to the system bus 113 via an interface, such as a display adapter 109. It is contemplated that the computing device 101 can have more than one display adapter 109 and the computing device 101 can have more than one display device 111. For example, a display device can be a monitor, an LCD (Liquid Crystal Display), an OLED (Organic Light Emitting Diode), or a projector. In addition to the display device 111, other output peripheral devices can comprise components such as speakers (not shown) and a printer (not shown) which can be connected to the computing device 101 via Input/Output Interface 110. Any step and/or result of the methods can be output in any form to an output device. Such output can be any form of visual representation, including, but not limited to, textual, graphical, animation, audio, tactile, and the like. The display 111 and computing device 101 can be part of one device, or separate devices.

The computing device 101 can operate in a networked environment using logical connections to one or more remote computing devices 114a,b,c. By way of example, a remote computing device can be a personal computer, portable computer, smartphone, a tablet, a server, a router, a network computer, a peer device or other common network node, and so on. In exemplary aspects, a remote computing device can be operated by a therapist as disclosed herein. Logical connections between the computing device 101 and a remote computing device 114a,b,c can be made via a network 115, such as a local area network (LAN) and/or a general wide area network (WAN). Such network connections can be through a network adapter 108. A network adapter 108 can be implemented in both wired and wireless environments. Such networking environments are conventional and commonplace in dwellings, offices, enterprise-wide computer networks, intranets, and the Internet.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of control processing software 106 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, solid state, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The above-described system components may be local to one of the devices (e.g., a computing device, such as a tablet or smartphone) or remote (e.g. servers in a remote data center, or "the cloud"). In exemplary aspects, it is contemplated that many of the system components can be provided in a "cloud" configuration.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method comprising:
   (a) using at least one processing unit of an MRI system to apply a high b-value diffusion-weighting gradient during acquisition of high b radial diffusion-weighted imaging signals from a selected portion of a nervous system of a subject, wherein the high b-value diffusion-weighting gradient is between 4,000 s/mm$^2$ and 31,550 s/mm$^2$, the selected portion of the nervous system comprising a bundle of axons and having:
      (i) a restricted region comprising an intra-axonal space positioned within myelinated axons of the bundle of axons, wherein the restricted region is depicted within an imaging pixel obtained by an MRI system; and
      (ii) a hindered region comprising an extra-axonal space positioned outside the myelinated axons of the bundle of axons,
   wherein the high b-value diffusion-weighting gradient is applied via the MRI system perpendicularly to an axonal fiber direction of the bundle of axons;
   (b) using the at least one processing unit to receive the high b radial diffusion-weighted imaging signals from the selected portion of the nervous system of the subject, wherein the high b value diffusion-weighting gradient is sufficient to suppress signals from the hindered region, wherein the received radial diffusion-weighted imaging signals are indicative of a signal from the restricted region, wherein the high b-value diffusion-weighting gradient is sufficient to suppress water signals from the extra-axonal space of the hindered region;
   (c) for each radial diffusion-weighted imaging signal of the high b radial diffusion-weighted imaging signals, using the at least one processing unit to determine an intensity of the radial diffusion-weighted imaging signal; and
   (d) using the at least one processing unit to calculate a high-b decay radial diffusion-weighted imaging signals of at least two high b radial diffusion-weighted imaging signals by fitting the determined intensities of the radial diffusion-weighted imaging signals to an exponential function, $$S_r(b) = S_{EA}^0 e^{-bD_L} + S_{IA}^0 e^{-bD_H},$$

wherein b is a given high b-value, $S_r(b)$ is the determined intensity for the given high b-value, $S_{EA}^0$ is an extra axonal intensity without diffusion decay, $S_{IA}^0$ is an intra axonal intensity without diffusion decay, $D_L$ is a low-b decay constant, and $D_H$ is the high-b decay constant, wherein the high-b decay constant is indicative of a degree of demyelination of the bundle of axons within the selected portion of the nervous system of the subject.

2. The method of claim 1, wherein the high b-value diffusion-weighting gradient is between 10,000 s/mm$^2$ and 31,550 s/mm$^2$.

3. The method of claim 1, wherein the selected portion of the nervous system of the subject comprises a selected portion of a spinal cord of the subject.

4. The method of claim 1, wherein the selected portion of the nervous system of the subject comprises a selected portion of a brain of the subject.

5. The method of claim 1, wherein the selected portion of the nervous system of the subject comprises an optic nerve of the subject.

6. The method of claim 1, wherein the subject is a patient having multiple sclerosis.

7. The method of claim 3, wherein the subject is a patient having a condition selected from a group consisting of: cervical spondylotic myelopathy (CSM), motor-neuron diseases including amyotrophic lateral sclerosis (ALS), metabolic vitamin B12 deficiency affecting spinal cord, transverse myelitis, transverse myelopathy, neuro myelitis optica, and combinations thereof.

8. The method of claim 1, wherein using the at least one processing unit to compare the at least two ultra-high b radial diffusion-weighted imaging signals comprises:
   (a) for each radial diffusion-weighted imaging signal, determining a fraction of restricted water within the restricted region; and
   (b) comparing the determined fractions of restricted water for the at least two radial diffusion-weighted imaging signals.

9. The method of claim 8, wherein the determined fraction of restricted water decreases between a first radial diffusion-weighted imaging signal and a second, subsequent diffusion-weighted imaging signal, and wherein a decrease in the determined fraction of restricted water is indicative of an exchange of water between the restricted region and the hindered region of the selected portion of the nervous system.

10. The method of claim 1, wherein using the at least one processing unit to compare the at least two ultra-high b radial diffusion-weighted imaging signals comprises:
    (a) comparing the determined intensities for the at least two radial diffusion-weighted imaging signals; and
    (b) calculating a signal decay rate based upon the determined intensities of the at least two high b radial diffusion-weighted imaging signals.

11. The method of claim 10, wherein the determined intensities of the at least two ultra-high b radial diffusion-weighted imaging signals decreases between a first radial diffusion-weighted imaging signal and a second, subsequent diffusion-weighted imaging signal, and wherein the decrease in the determined signal intensities is indicative of an exchange of water between the restricted region and the hindered region of the selected portion of the nervous system.

12. The method of claim 10, wherein using the at least one processing unit to compare the at least two ultra-high b radial diffusion-weighted imaging signals further comprises calculating a signal decay rate based upon the determined intensities of the at least two radial diffusion-weighted imaging signals.

13. The method of claim 12, further comprising: using the at least one processing unit to determine whether the signal decay rate exceeds a threshold value, wherein the signal decay rate being above the threshold value is indicative of an exchange of water between the restricted region and the hindered region of the selected portion of the nervous system.

14. The method of claim 1, further comprising using the at least one processing unit to:
    before obtaining the ultra-high b radial diffusion-weighted imaging signals from the selected portion of the nervous system of the subject, perform a Monte Carlo simulation of water diffusion within the selected portion of the nervous system;
    generating a model of the simulated water diffusion;
    determining one or more diffusion parameters of the model of the simulated water diffusion; and
    using the one or more diffusion parameters of the model of the simulated water diffusion to determine the ultra-high b value diffusion-weighting gradient that is applied to the bundle of axons of the selected portion of the nervous system.

15. A system comprising at least one processing unit, wherein the at least one processing unit is configured to:
    (a) apply a high b-value diffusion-weighting gradient during acquisition of high b radial diffusion-weighted imaging signals from a selected portion of a nervous system of a subject, wherein the high b-value diffusion-weighting gradient is between 4,000 s/mm$^2$ and 31,550 s/mm$^2$, the selected portion of the nervous system comprising a bundle of axons and having:
        (i) a restricted region comprising an intra-axonal space positioned within myelinated axons of the bundle of axons, wherein the restricted region is depicted within an imaging pixel obtained by an MRI system; and
        (ii) a hindered region comprising an extra-axonal space positioned outside the myelinated axons of the bundle of axons,
        wherein the high b-value diffusion-weighting gradient is applied via the MRI system perpendicularly to an axonal fiber direction of the bundle of axons;
    (b) receive the high b radial diffusion-weighted imaging signals from the selected portion of the nervous system of the subject, wherein the high b-value diffusion-weighting gradient is sufficient to suppress signals from the hindered region, wherein the received radial diffusion-weighting imaging signals are indicative of a signal from the restricted region, wherein the high b-value diffusion-weighting gradient is sufficient to suppress water signals from the extra-axonal space of the hindered region;
    (c) for each radial diffusion-weighted imaging signal, determine an intensity of the radial diffusion-weighted imaging signal; and
    (d) calculate a high-b decay constant based upon the determined intensities of the high b radial diffusion-weighted imaging signals of at least two high b radial diffusion-weighted imaging signals by fitting the determined intensities of the radial diffusion-weighted imaging signals to an exponential function, $$S_r(b)=S_{EA}^0 e^{-bD_L}+S_{IA}^0 e^{-bD_H},$$

wherein b is a given high b-value, $S_r(b)$ is the determined intensity for the given high b-value, $S_{EA}^0$ is an extra axonal intensity without diffusion decay, $S_{IA}^0$ is an intra axonal intensity without diffusion decay, $D_L$ is a low-b decay constant, and $D_H$ is the high-b decay constant,
    wherein the high-b decay constant is indicative of a degree of demyelination of the bundle of axons within the selected portion of the nervous system of the subject.

16. The system of claim 15, wherein the high b-value diffusion-weighting gradient is greater than 10,000 s/mm$^2$.

17. The system of claim 15, wherein the at least one processing unit is configured to:
    (a) for each radial diffusion-weighted imaging signal, determine a fraction of restricted water within the restricted region; and (b) compare the determined fractions of restricted water for the at least two high b radial diffusion-weighted imaging signals.

18. The system of claim 15, wherein the at least one processing unit is configured to:
 (a) compare the determined intensities for the at least two high b radial diffusion-weighted imaging signals; and
 (b) calculate a signal decay rate based upon the determined intensities of the at least two high b radial diffusion-weighted imaging signals.

19. The system of claim 18, wherein the at least one processing unit is further configured to determine whether the signal decay rate exceeds a threshold value, wherein the signal decay rate being above the threshold value is indicative of an exchange of water between the restricted region and the hindered region of the selected portion of the nervous system.

20. The system of claim 15, wherein the at least one processing unit is configured to compare the high-b decay constant to a high-b decay constant of a healthy subject.

\* \* \* \* \*